US008349262B2

(12) United States Patent
Hyde et al.

(10) Patent No.: US 8,349,262 B2
(45) Date of Patent: Jan. 8, 2013

(54) NITRIC OXIDE PERMEABLE HOUSINGS

(75) Inventors: Roderick A. Hyde, Redmond, WA (US); Muriel Y. Ishikawa, Livermore, CA (US); Lowell L. Wood, Jr., Bellevue, WA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 1354 days.

(21) Appl. No.: 12/008,694

(22) Filed: Jan. 11, 2008

(65) Prior Publication Data

US 2009/0110612 A1   Apr. 30, 2009

Related U.S. Application Data

(63) Continuation-in-part of application No. 11/981,743, filed on Oct. 30, 2007, and a continuation-in-part of application No. 11/998,864, filed on Nov. 30, 2007, now Pat. No. 8,221,690, and a continuation-in-part of application No. 12/005,045, filed on Dec. 21, 2007, and a continuation-in-part of application No. 12/005,065, filed on Dec. 21, 2007, now Pat. No. 7,862,598, and a continuation-in-part of application No. 12/005,132, filed on Dec. 21, 2007, and a continuation-in-part of application No. 12/005,136, filed on Dec. 21, 2007, and a continuation-in-part of application No. 12/005,170, filed on Dec. 21, 2007, and a continuation-in-part of application No. 12/006,090, filed on Dec. 28, 2007, and a continuation-in-part of application No. 12/006,049, filed on Dec. 28, 2007, now abandoned, and a continuation-in-part of application No. 12/006,069, filed on Dec. 28, 2007, now abandoned, and a continuation-in-part of application No. 12/008,708, filed on Jan. 11, 2008.

(51) Int. Cl.
*C12M 1/00* (2006.01)
*B01J 8/00* (2006.01)

(52) U.S. Cl. .................................... 422/129; 435/286.1
(58) Field of Classification Search .................. 422/129; 435/286.1
See application file for complete search history.

(56) References Cited

U.S. PATENT DOCUMENTS

| 4,162,536 | A |   | 7/1979 | Morley |
|---|---|---|---|---|
| 4,210,697 | A |   | 7/1980 | Adiletta |
| 4,248,214 | A |   | 2/1981 | Hannah et al. |
| 4,561,429 | A |   | 12/1985 | Sato et al. |
| 4,611,594 | A |   | 9/1986 | Grayhack et al. |
| 4,919,149 | A |   | 4/1990 | Stang |
| 5,109,871 | A |   | 5/1992 | Thornton |
| 5,279,294 | A |   | 1/1994 | Anderson et al. |
| 5,351,698 | A |   | 10/1994 | Wheeler et al. |
| 5,366,997 | A |   | 11/1994 | Keefer et al. |
| 5,374,710 | A | * | 12/1994 | Tsien et al. ................... 534/552 |
| 5,405,919 | A |   | 4/1995 | Keefer et al. |
| 5,495,961 | A |   | 3/1996 | Maestre |
| 5,530,263 | A |   | 6/1996 | DiVincenzo |
| 5,571,152 | A |   | 11/1996 | Chen et al. |
| 5,580,433 | A |   | 12/1996 | Baker et al. |
| 5,665,077 | A |   | 9/1997 | Rosen et al. |
| 5,676,963 | A |   | 10/1997 | Keefer et al. |
| 5,683,668 | A |   | 11/1997 | Hrabie et al. |
| 5,690,777 | A |   | 11/1997 | Kuethe et al. |
| 5,736,152 | A |   | 4/1998 | Dunn |
| 5,765,558 | A |   | 6/1998 | Psaros et al. |
| 5,814,666 | A |   | 9/1998 | Green et al. |
| 5,858,799 | A |   | 1/1999 | Yee et al. |
| 5,900,433 | A |   | 5/1999 | Igo et al. |
| 5,910,316 | A |   | 6/1999 | Keefer et al. |
| 5,943,160 | A |   | 8/1999 | Downing |
| 5,956,172 | A |   | 9/1999 | Downing |
| 5,980,705 | A |   | 11/1999 | Allen et al. |
| 5,994,444 | A |   | 11/1999 | Trescony et al. |
| 6,000,398 | A |   | 12/1999 | Alla et al. |
| 6,037,346 | A |   | 3/2000 | Doherty, Jr. et al. |
| 6,080,110 | A |   | 6/2000 | Thorgersen |
| 6,100,096 | A |   | 8/2000 | Bollinger et al. |
| 6,103,765 | A |   | 8/2000 | Neal |
| 6,127,363 | A |   | 10/2000 | Doherty, Jr. et al. |
| 6,143,314 | A |   | 11/2000 | Chandrashekar et al. |
| 6,149,606 | A |   | 11/2000 | Alving et al. |
| 6,156,753 | A |   | 12/2000 | Doherty, Jr. et al. |
| 6,182,661 | B1 |   | 2/2001 | Solanki et al. |
| 6,190,704 | B1 |   | 2/2001 | Murrell |
| 6,223,747 | B1 |   | 5/2001 | Rudge et al. |
| 6,265,420 | B1 |   | 7/2001 | Lai |
| 6,280,604 | B1 |   | 8/2001 | Allen et al. |
| 6,287,601 | B1 |   | 9/2001 | Russell |
| 6,306,609 | B1 |   | 10/2001 | Lai |
| 6,308,708 | B2 |   | 10/2001 | Strauss et al. |
| 6,321,751 | B1 |   | 11/2001 | Strauss et al. |
| 6,327,074 | B1 |   | 12/2001 | Bass et al. |
| 6,341,607 | B1 |   | 1/2002 | Couvreur |
| 6,369,071 | B1 |   | 4/2002 | Haj-Yehia |
| 6,432,077 | B1 |   | 8/2002 | Stenzler |
| 6,436,470 | B1 |   | 8/2002 | Iacocca et al. |
| 6,440,498 | B2 |   | 8/2002 | Schaller |
| 6,451,337 | B1 |   | 9/2002 | Smith et al. |
| 6,469,051 | B2 |   | 10/2002 | Nagano et al. |
| 6,559,184 | B2 |   | 5/2003 | Neal |

(Continued)

FOREIGN PATENT DOCUMENTS

DE            20115123 U1      6/2001

(Continued)

OTHER PUBLICATIONS

Jamal, Sophie A. et al.; "Effect of Nitroglycerin Ointment on Bone Density and Strength in Postmenopausal Women"; JAMA; bearing a date of Feb. 23, 2011; pp. 800-807; vol. 305, No. 8; American Medical Association.

(Continued)

*Primary Examiner* — Rebecca Anderson
*Assistant Examiner* — Samantha Shterengarts

(57) ABSTRACT

The present disclosure relates to an apparatus that includes one or more nitric oxide permeable housings.

24 Claims, 20 Drawing Sheets

U.S. PATENT DOCUMENTS

| | | |
|---|---|---|
| 6,621,687 B2 | 9/2003 | Lewis, Jr. et al. |
| 6,635,273 B1 | 10/2003 | Loscalzo et al. |
| 6,635,415 B1 | 10/2003 | Bollinger et al. |
| 6,636,652 B1 | 10/2003 | Kopelman et al. |
| 6,639,007 B2 | 10/2003 | Plamthottam |
| 6,651,667 B2 | 11/2003 | Osterberg |
| 6,673,338 B1 | 1/2004 | Arnold et al. |
| 6,673,871 B2 | 1/2004 | Warneke et al. |
| 6,696,072 B1 | 2/2004 | Podolski |
| 6,706,274 B2 | 3/2004 | Herrmann et al. |
| 6,743,249 B1 | 6/2004 | Alden |
| 6,747,062 B2 | 6/2004 | Murrell |
| 6,773,714 B2 | 8/2004 | Dunn et al. |
| 6,812,500 B2 | 11/2004 | Reeh et al. |
| 6,818,356 B1 | 11/2004 | Bates |
| 6,840,244 B2 | 1/2005 | Kemp |
| 6,841,166 B1 | 1/2005 | Zhang et al. |
| 6,900,891 B2 | 5/2005 | Kopelman et al. |
| 6,943,166 B1 | 9/2005 | Pullman et al. |
| 6,969,507 B2 | 11/2005 | Weisskoff et al. |
| 6,983,751 B2 | 1/2006 | Osterberg |
| 6,994,934 B2 | 2/2006 | Stanish et al. |
| 7,052,711 B2 | 5/2006 | West et al. |
| 7,088,040 B1 | 8/2006 | Ducharme et al. |
| 7,105,502 B2 | 9/2006 | Arnold et al. |
| 7,105,607 B2 | 9/2006 | Chen |
| 7,122,046 B2 | 10/2006 | Augustine et al. |
| 7,122,529 B2 | 10/2006 | Ruane et al. |
| 7,144,655 B2 | 12/2006 | Jenson et al. |
| 7,181,174 B2 | 2/2007 | Fitzgibbon et al. |
| 7,181,261 B2 | 2/2007 | Silver et al. |
| 7,183,001 B1 | 2/2007 | Ederle et al. |
| 7,189,471 B2 | 3/2007 | Jankowksi et al. |
| 7,194,801 B2 | 3/2007 | Jenson et al. |
| 7,206,605 B2 | 4/2007 | Hattori |
| 7,210,817 B2 | 5/2007 | Lee et al. |
| 7,215,687 B2 | 5/2007 | Kawai et al. |
| 7,215,887 B2 | 5/2007 | Ternullo et al. |
| 7,217,882 B2 | 5/2007 | Walukiewicz et al. |
| 7,218,900 B2 | 5/2007 | Suzuki |
| 7,220,258 B2 | 5/2007 | Myhr |
| 7,227,956 B1 | 6/2007 | Onishi |
| 7,235,189 B2 | 6/2007 | Höhn et al. |
| 7,235,361 B2 | 6/2007 | Bawendi et al. |
| 7,235,505 B2 | 6/2007 | Gromelski et al. |
| 7,236,595 B1 | 6/2007 | Bean et al. |
| 7,238,628 B2 | 7/2007 | Demaray et al. |
| 7,245,894 B2 | 7/2007 | Sekiguchi et al. |
| RE39,785 E | 8/2007 | Fuse |
| 7,253,953 B2 | 8/2007 | Browning |
| 7,254,160 B2 | 8/2007 | Kawamoto et al. |
| 7,256,923 B2 | 8/2007 | Liu et al. |
| 7,257,327 B2 | 8/2007 | Small |
| 7,260,155 B2 | 8/2007 | Stonick et al. |
| 7,260,402 B1 | 8/2007 | Ahmed |
| 7,260,764 B2 | 8/2007 | Chen |
| 7,260,768 B1 | 8/2007 | Matsumoto et al. |
| 7,261,693 B2 | 8/2007 | Wilcox et al. |
| 7,264,602 B1 | 9/2007 | Longsworth |
| 7,273,567 B1 * | 9/2007 | Wellinghoff et al. .... 252/187.23 |
| 7,280,811 B2 | 10/2007 | Sugiyama et al. |
| 7,283,710 B2 | 10/2007 | Sano et al. |
| 7,294,678 B2 | 11/2007 | McGlothlin et al. |
| 7,294,779 B2 | 11/2007 | Watabe et al. |
| 7,295,737 B2 | 11/2007 | Moorjani et al. |
| 7,295,741 B2 | 11/2007 | Sako et al. |
| 7,298,605 B2 | 11/2007 | Itoh et al. |
| 7,298,977 B2 | 11/2007 | Ohsawa et al. |
| 7,301,751 B2 | 11/2007 | Lee et al. |
| 7,301,754 B1 | 11/2007 | Knowles |
| 7,303,333 B2 | 12/2007 | Yu |
| 7,418,399 B2 | 8/2008 | Schaeffer et al. |
| 7,449,595 B2 | 11/2008 | Garvey et al. |
| 7,582,623 B2 | 9/2009 | Mascharak |
| 7,603,166 B2 | 10/2009 | Casscells, III et al. |
| 7,829,553 B2 * | 11/2010 | Arnold et al. ................ 514/149 |
| 7,899,539 B2 | 3/2011 | Whitehurst et al. |
| 2002/0022046 A1 | 2/2002 | Tedeschi et al. |
| 2002/0026937 A1* | 3/2002 | Mault ..................... 128/200.24 |
| 2002/0055702 A1 | 5/2002 | Atala et al. |
| 2002/0068365 A1 | 6/2002 | Kuhrts |
| 2002/0138051 A1 | 9/2002 | Hole et al. |
| 2002/0165179 A1 | 11/2002 | Baker, Jr. |
| 2002/0188323 A1 | 12/2002 | Penner et al. |
| 2003/0009127 A1 | 1/2003 | Trescony et al. |
| 2003/0039697 A1 | 2/2003 | Zhao et al. |
| 2003/0073133 A1 | 4/2003 | Leyland-Jones |
| 2003/0077243 A1 | 4/2003 | Fitzhugh et al. |
| 2003/0088191 A1 | 5/2003 | Freeman et al. |
| 2003/0093143 A1 | 5/2003 | Zhao et al. |
| 2003/0165578 A1 | 9/2003 | Murrell |
| 2003/0203915 A1 | 10/2003 | Fang et al. |
| 2004/0009238 A1 | 1/2004 | Miller et al. |
| 2004/0013747 A1 | 1/2004 | Tucker et al. |
| 2004/0072360 A1 | 4/2004 | Naaman et al. |
| 2004/0081580 A1 | 4/2004 | Hole et al. |
| 2004/0087831 A1 | 5/2004 | Michels et al. |
| 2004/0193218 A1 | 9/2004 | Butler |
| 2004/0247640 A1 | 12/2004 | Zhao et al. |
| 2005/0053106 A1 | 3/2005 | Herron et al. |
| 2005/0079148 A1 | 4/2005 | Fitzhugh et al. |
| 2005/0136483 A1* | 6/2005 | Carlson ........................ 435/7.1 |
| 2005/0181026 A1 | 8/2005 | Davis et al. |
| 2005/0197682 A1 | 9/2005 | Fox et al. |
| 2005/0203069 A1 | 9/2005 | Arnold et al. |
| 2005/0220838 A1 | 10/2005 | Zhao et al. |
| 2005/0249667 A1 | 11/2005 | Tuszynski et al. |
| 2005/0267090 A1 | 12/2005 | Mascharak |
| 2006/0074282 A1 | 4/2006 | Ward et al. |
| 2006/0134728 A1 | 6/2006 | MacDonald et al. |
| 2006/0206171 A1 | 9/2006 | Gertner et al. |
| 2006/0206173 A1 | 9/2006 | Gertner et al. |
| 2006/0275350 A1 | 12/2006 | Davis et al. |
| 2006/0280307 A1 | 12/2006 | Ikushima et al. |
| 2007/0021382 A1 | 1/2007 | Assaf et al. |
| 2007/0053996 A1 | 3/2007 | Boyden et al. |
| 2007/0065473 A1 | 3/2007 | Miller |
| 2007/0088316 A1 | 4/2007 | Stenzler et al. |
| 2007/0148117 A1 | 6/2007 | Davis et al. |
| 2007/0166357 A1 | 7/2007 | Shaffer et al. |
| 2007/0181444 A1 | 8/2007 | Bernstein et al. |
| 2007/0190122 A1 | 8/2007 | Davis et al. |
| 2007/0208395 A1 | 9/2007 | Leclerc et al. |
| 2007/0274874 A1 | 11/2007 | Miller et al. |
| 2007/0298354 A1 | 12/2007 | Ding et al. |
| 2008/0069863 A1 | 3/2008 | Peters |
| 2008/0097282 A1 | 4/2008 | Hole et al. |
| 2008/0220048 A1 | 9/2008 | Chen et al. |
| 2008/0281383 A1 | 11/2008 | Butler |
| 2008/0286321 A1 | 11/2008 | Reneker et al. |
| 2008/0311163 A1 | 12/2008 | Peters |
| 2009/0081279 A1 | 3/2009 | Jezek et al. |
| 2009/0202617 A1 | 8/2009 | Ward et al. |
| 2009/0204057 A1 | 8/2009 | Woo et al. |
| 2009/0214618 A1 | 8/2009 | Schoenfisch et al. |
| 2009/0214624 A1 | 8/2009 | Smith et al. |
| 2010/0081144 A1 | 4/2010 | Holmes et al. |
| 2010/0152683 A1 | 6/2010 | Lindgren et al. |
| 2010/0197802 A1 | 8/2010 | Jezek et al. |
| 2011/0008815 A1 | 1/2011 | Stamler et al. |

FOREIGN PATENT DOCUMENTS

| | | |
|---|---|---|
| EP | 1 704 877 A1 | 9/2006 |
| WO | WO 92/09962 | 6/1992 |
| WO | WO 96/08966 A1 | 3/1996 |
| WO | WO 00/53193 | 9/2000 |
| WO | WO 01/10344 A1 | 2/2001 |
| WO | WO 02/17898 A2 | 3/2002 |
| WO | WO 02/057738 A2 | 7/2002 |
| WO | WO 03/006427 A1 | 1/2003 |
| WO | WO 03/086282 A2 | 10/2003 |
| WO | WO 2005/070008 A2 | 8/2005 |
| WO | WO 2005/112954 A1 | 12/2005 |
| WO | WO 2006/084912 A1 | 8/2006 |
| WO | WO 2006/095193 A2 | 9/2006 |
| WO | WO 2006/100155 A1 | 9/2006 |
| WO | WO 2006/107122 A1 | 10/2006 |

| | | | |
|---|---|---|---|
| WO | WO 2006/108420 A1 | 10/2006 |
| WO | WO 2007/130702 A2 | 11/2007 |
| WO | WO 2008/046211 A1 | 4/2008 |
| WO | WO 2009/131931 A1 | 10/2009 |

OTHER PUBLICATIONS

Khosla, Sundeep; "Is Nitroglycerin a Novel and Inexpensive Treatment for Osteoporosis?"; JAMA; bearing a date of Feb. 23, 2011; pp. 826-827; vol. 305, No. 8; American Medical Association.

Mims, Christopher; "Erectile Dysfunction Treatment to Save Soldiers' Lives"; Technology Review; bearing a date of Feb. 22, 2011; 2 pages; MIT; located at http://www.technologyreview.com/blog/mimssbits/26427/?pl=A5.

U.S. Appl. No. 12/930,351, Hyde et al.

Butler, P. et al.; "Cell Transplantation from Limb Allografts"; Plastic and Reconstructive Surgery; Bearing a date of Jul. 1998; pp. 161-168 (11 total pages); vol. 102, No. 1; American Society of Plastic Surgeons; located at: http://www.plasreconsurg.com; printed on Apr. 25, 2008.

Butler, A.R.; Nicholson, R.; *Life, Death and Nitric Oxide*; Bearing a date of Oct. 17, 2003; 1$^{st}$ edition; Royal Society of Chemistry; ISBN 978-0854046867 (Not Provided).

U.S. Appl. No. 12/148,284, Hyde et al.

U.S. Appl. No. 12/148,283, Hyde et al.

De Lima, R.G. et al.; "Controlled Nitric Oxide Photo-Release From Nitro Ruthenium Complexes: The Vasodilator Response Produced by UV Light Irradiation"; Inorganica Chimica Acta; Bearing a date of 2005; pp. 2643-2650; vol. 358; Elsevier B.V.; located at: http://www.sciencedirect.com.

Frank, S. et al.; "Nitric Oxide Triggers Enhanced Induction of Vascular Endothelial Growth Factor Expression in Cultured Keratinocytes (HaCaT) and During Cutaneous Wound Repair"; The FASEB Journal; Bearing a date of 1999; pp. 2002-2014; vol. 13.

Ghaffari, A. et al.; "A Direct Nitric Oxide Gas Delivery System for Bacterial and Mammalian Cell Cultures"; Nitric Oxide; Bearing a date of 2005; pp. 129-140; vol. 12; Elsevier Inc.; located at: http://www.sciencedirect.com.

Ghaffari, A. et al.; "Efficacy of Gaseous Nitric Oxide in the Treatment of Skin and Soft Tissue Infections"; Wound Repair and Regeneration; Bearing a date of 2007; pp. 368-377; vol. 15; Wound Healing Society.

Ghaffari, A. et al.; "Potential Application of Gaseous Nitric Oxide as a Topical Antimicrobial Agent"; Nitric Oxide; Bearing a date of 2006; pp. 21-29; vol. 14; Elsevier Inc.; located at: http://www.sciencedirect.com.

Goldsmith, P.C. et al.; "Inhibitors of Nitric Oxide Synthase in Human Skin"; The Journal of Investigative Dermatology; Bearing a date of Jan. 1996; pp. 113-118; vol. 106, No. 1; The Society for Investigative Dermatology, Inc.

Govers, R.; Rabelink, T.J.; "Cellular Regulation of Endothelial Nitric Oxide Synthase"; Am. J. Physiol. Renal. Physiol.; Bearing a date of 2001; pp. F193-F206; vol. 280; The American Physiological Society; located at: http://www.ajprenal.org.

Guo, H.; "Two-and Three-Photon Upconversion of LaOBr:Er3$_{3+}$"; Optical Materials; Bearing a date of 2007; pp. 1840-1843; vol. 29; Elsevier B.V.; located at: http://www.sciencedirect.com.

Hassett, D.J.; Imlay, J.A.; "Bactericidal Antibiotics and Oxidative Stress: A Radical Proposal"; ACS Chemical Biology; Bearing a date of 2007; pp. 708-710; vol. 2, No. 11; located at: http://www.acschemicalbiology.org.

Miller, C.C. et al.; "Treatment of Chronic Nonhealing Leg Ulceration with Gaseous Nitric Oxide: A Case Study"; Journal of Cutaneous Medicine and Surgery; Bearing a date of Aug. 2004; pp. 233-238; vol. 8, No. 4.

Pacher, P. et al.; "Nitric Oxide and Peroxynitrite in Health and Disease"; Physiol. Rev.; Bearing a date of Jan. 2007; pp. 315-424; vol. 87; The American Physiological Society; located at: http://www.prv.org.

Patel, D.N. et al.; "Spectroscopic and Two-Photon Upconversion Studies of Ho$^{3+}$-Doped Lu$_3$Al$_5$O$_{12}$"; Optical Materials; Bearing a date of Jul. 1998; pp. 225-234; vol. 10; Elsevier Science B.V.

Rapaport, A. et al.; "Review of the Properties of Up-Conversion Phosphors for New Emissive Displays"; Journal of Display Technology; Bearing a date of Mar. 2006; pp. 68-78; vol. 2, No. 1; IEEE.

Romero-Graillet, C. et al.; "Nitric Oxide Produced by Ultraviolet-Irradiated Keratinocytes Stimulates Melanogenesis"; J. Clin. Invest.; Bearing a date of Feb. 1997; pp. 635-642; vol. 99, No. 4; The American Society of Clinical Investigation, Inc.

Seabra, A.B. et al.; "S-Nitrosoglutathione Incorporated in Poly(Ethylene Glycol) Matrix: Potential Use for Topical Nitric Oxide Delivery"; Nitric Oxide; Bearing a date of 2004; pp. 263-272; vol. 11; Elsevier Inc.; located at: http://www.sciencedirect.com.

Shabani, M. et al.; "Enhancement of Wound Repair with a Topically Applied Nitric Oxide-Releasing Polymer"; Wound Repair and Regeneration; Bearing dates of Jul.-Sep. 1996; pp. 353-362; vol. 4, No. 3; The Wound Healing Society.

Sussman, C.; *Wound Care: A Collaborative Practice Manual*; Bearing a date of Jan. 2007; ISBN 0781774446 (Not Provided).

Suzuki, H.; Hewitt, C.W.; "Cell Transplantation from Limb Allografts: Discussion"; Plastic and Reconstructive Surgery; Bearing a date of Jul. 1998; pp. 169-170 (2 total pages); vol. 102, No. 1; American Society of Plastic Surgeons; located at: http://www.plasreconsurg.com; printed on May 2, 2008.

Tamir, S.; Tannenbaum, S.R.; "The Role of Nitric Oxide (NO) in the Carcinogenic Process"; Biochimica et Biophysica Acta; Bearing a date of 1996; pp. F31-F36; vol. 1288; Elsevier Science B.V.

Tu, H. et al.; "A Novel Electrochemical Microsensor for Nitric Oxide Based on Electropolymerized Film of *o*-Aminobenzaldehyde-Ethylene-Diamine Nickel"; Electroanalysis; Bearing a date of 1999; pp. 70-74; vol. 11, No. 1; Wiley-VCH.

Van Faasen, E.; Vanin, A. (Eds); *Radicals for Life: The Various Forms of Nitric Oxide*; Bearing a date of Mar. 2007; 442 pages; ISBN 978-0-444-52236-8; Elsevier (Not Provided).

Weller, R. et al.; "Antimicrobial Effect of Acidified Nitrite on Dermatophyte Fungi, *Candida* and Bacterial Skin Pathogens"; Journal of Applied Microbiology; Bearing a date of 2001; pp. 648-652; vol. 90; The Society for Applied Microbiology.

Weller, R. et al.; "Nitric Oxide Is Generated on the Skin Surface by Reduction of Sweat Nitrate"; The Journal of Investigative Dermatology; Bearing a date of Sep. 1996; pp. 327-331; vol. 107, No. 3; The Society of Investigative Dermatology, Inc.

Yamasaki, K. et al.; "Reversal of Impaired Wound Repair in iNOS-Deficient Mice by Topical Adenoviral-Mediated iNOS Gene Transfer"; J. Clin. Invest.; Bearing a date of Mar. 1998; pp. 967-971; vol. 101, No. 5; The American Society for Clinical Investigation, Inc.; located at: http://www.jci.org.

Zhelyaskov, V.R.; Godwin, D.W.; "Photolytic Generation of Nitric Oxide Through a Porous Glass Partitioning Membrane"; Nitric Oxide: Biology and Chemistry; Bearing a date of 1998; pp. 454-459; vol. 2, No. 6; Article No. NO980195; Academic Press.

"A Method of Nitric Oxide Delivery for Healing and Organ Preservation"; University of Texas at Dallas; bearing a date of May 18, 2009; p. 1; located at http://utdallas.technologypublisher.com/TechnologyProject.aspx?id=2302.

"Nanotechnology bandage speeds up healing"; Nanowerk News; Source: Akron Beacon Journal (Paula Schleis); bearing a date of Dec. 15, 2006; pp. 1-2; printed on Jul. 14, 2009; located at http://www.nanowerk.com/news/newsid=1156.php.

Birkeland et al.; "On the Oxidation of Atmospheric Nitrogen in Electric Arcs"; Nature; bearing a date of 1898; pp. 98-116; No. 1,506, vol. 58.

Levine et al.; "A New, Highly Efficient Red-Emitting Cathodoluminescent Phosphor (YVO$_4$:Eu) for Color Television"; Applied Physics Letters; bearing a date of Sep. 15, 1964; pp. 1-3; vol. 5, No. 6.

Mellor, J. W.; "Modern Inorganic Chemistry"; excerpt from Modern Inorganic Chemistry; bearing a date of 1912; pp. 1-19; Longmans, Greene, and Co.

"The Shadow Mask and Aperture Grill"; The PC Guide; bearing a date of Apr. 17, 2001; pp. 1-3; © Copyright 1997-2004 Charles M. Kozierok; printed Oct. 6, 2009; located at http://www.pcguide.com/ref/crt/crtMask-c.html.

"Nanotechnology—The new Viagra?"; Nanowerk News; bearing a date of Apr. 26, 2009; p. 1; located at http://www.nanowerk.com/news/newsid=10273.php.

Stubbington, Tommy; "New Condom Nears Approval"; The Wall Street Journal Online; bearing at date of Apr. 20, 2011; pp. 1-2; 13:18; Dow Jones & Company, Inc.

Liu et al.; "Novel Delivery System for the Bioregulatory Agent Nitric Oxide"; Chemistry of Materials; bearing a date of 2009; pp. 5032-5041; vol. 21, No. 21; © 2009 American Chemical Society.

"Nitric oxide-releasing wrap for donor organs and cloth for therapeutic socks"; e! Science News; bearing a date of Jan. 6, 2010; pp. 1-2; located at http://esciencenews.com/articles/2010/01/06/nitric.oxide.releasing.wrap.donor.organs.and.cloth.therapeutic.socks; printed on Jan. 19, 2010.

Andrews, Karen L. et al.; "A Photosensitive Vascular Smooth Muscle Store of Nitric Oxide in Mouse Aorta: No Dependence on Expression of Endothelial Nitric Oxide Synthase"; British Journal of Pharmacology; 2003; pp. 932-940; vol. 138; Nature Publishing Group.

Bonaventura, Daniella et al.; "A Macrocyclic Nitrosyl Ruthenium Complex is a NO Donor that Induces Rat Aorta Relaxation"; Nitric Oxide; Mar. 2004; pp. 83-91 (p. 1); vol. 10, Issue 2; located at: http://www.sciencedirect.com; printed on Oct. 26, 2007 (Abstract Only).

Burrell, María A. et al.; "Detection of Nitric Oxide Synthase (NOS) in Somatostatin-Producing Cells of Human and Murine Stomach and Pancreas"; The Journal of Histochemistry and Cytochemistry; 1996; pp. 339-346; vol. 44, No. 4; The Histochemical Society, Inc.

Chmura, Antonina et al.; "The Role of Photoinduced Electron Transfer Processes in Photodegradation of the $[Fe_4(\mu_3-S)_3(NO)_7]^-$ Cluster"; Nitric Oxide; Dec. 2006; pp. 370-379 (p. 1); vol. 15, Issue 4; located at: http://www.sciencedirect.com; printed on Oct. 26, 2007 (Abstract Only).

Chen, X; Gillis, CN; "Methylene Blue Enhanced Photorelaxation in Aorta, Pulmonary Artery and Corpus Cavernosum"; Biochem. Biophys. Res. Commun.; Jan. 29, 1993; pp. 559-563 (pp. 1-2); vol. 190, No. 2; located at: http://www.pubmed.gov; printed on Oct. 26, 2007 (Abstract Only).

Dujić, Željko et al; "Aerobic Exercise Before Diving Reduces Venous Gas Bubble Formation in Humans"; J. Physiol.; 2004; pp. 637-642; vol. 555.3; The Physiological Society.

"Easy Life II"; Photon Technology International; pp. 1-3; located at: http://www.pti-nj.com/EasyLife/easylife.html; printed on Oct. 6, 2007.

Ferezin, Camila Z. et al; "The Complex Trans-$[RuCl([15]aneN_4)NO]^{2+}$ Induces Rat Aorta Relaxation by Ultraviolet Light Irradiation"; Nitric Oxide; Nov. 2005; pp. 170-175 (p. 1); vol. 13, Issue 3; located at: http://www.sciencedirect.com; printed on Oct. 26, 2007 (Abstract Only).

Flitney, FW et al.; "Iron-Sulphur Cluster Nitrosyls, a Novel Class of Nitric Oxide Generator: Mechanism of Vasodilator Action on Rat Isolated Tail Artery"; Br. J. Pharmacol.; Nov. 1992; pp. 842-848 (pp. 1-2); vol. 107, No. 3; located at: http://www.pubmed.gov; printed on Oct. 26, 2007 (Abstract Only).

Flitney, Frederick Werner; Megson, Ian L.; "Nitric Oxide and the Mechanism of Rat Vascular Smooth Muscle Photorelaxation"; J. Physiol.; 2003; pp. 819-828; vol. 550.3; The Physiological Society.

Flitney, FW et al.; "Vasodilator Responses of Rat Isolated Tail Artery Enhanced by Oxygen-Dependent, Photochemical Release of Nitric Oxide from Iron-Sulphur-Nitrosyls"; Br. J. Pharmacol.; Apr. 1996; pp. 1549-1557 (pp. 1-2); vol. 117, No. 7; located at: http://www.pubmed.gov; printed on Oct. 26, 2007 (Abstract Only).

Fukuhara, Kiyoshi et al.; "Photochemical Generation of Nitric Oxide from 6-Nitrobenzo[a]pyrene"; J. Am. Chem. Soc.; 2001; pp. 8662-8666 (p. 1); vol. 123, No. 36; located at: http://pubs.acs.org/cgi-bin/abstract.cgi/jacsat/2001/123/i36/abs/ja0109038.html; printed on Oct. 26, 2007 (Abstract Only).

Gaston, Benjamin; "Summary: Systemic Effects of Inhaled Nitric Oxide"; Proceedings of the American Thoracic Society; 2006; pp. 170-172; vol. 3.

Gau, Jen-JR et al.; "A MEMS Based Amperometric Detector for E. coli Bacteria Using Self-Assembled Monolayers"; Biosensors & Bioelectronics; 2001; pp. 745-755; vol. 16; Elsevier Science B.V.

Graham-Rowe, Duncan; "Photonic Fabrics Take Shape"; Nature Photonics; Jan. 2007; pp. 6-7; vol. 1; Nature Publishing Group.

Hardwick, J.B.J. et al.; "A Novel Method for the Delivery of Nitric Oxide Therapy to the Skin of Human Subjects Using a Semi-Permeable Membrane"; Clinical Science; 2001; pp. 395-400; vol. 100; The Biochemical Society and the Medical Research Society.

Hattenbach, Lars-Olof et al.; "Detection of Inducible Nitric Oxide Synthase and Vascular Endothelial Growth Factor in Choroidal Neovascular Membranes"; Ophthalmologica; 2002; pp. 209-214; vol. 216; S. Karger AG, Basel.

Hou, Yongchun et al.; "Nanomolar Scale Nitric Oxide Generation from Self-Assembled Monolayer Modified Gold Electrodes"; Chem. Commun.; 2000; pp. 1831-1832; The Royal Society of Chemistry.

Hrabie, Joseph A.; Keefer, Larry K.; "Chemistry of the Nitric Oxide-Releasing Diazeniumdiolate ("Nitrosohydroxylamine") Functional Group and Its Oxygen-Substituted Derivatives"; Chem. Rev.; 2002; pp. 1135-1154; vol. 102; American Chemical Society.

Ikeda, Osamu et al.; "Nitric Oxide Detection with Glassy Carbon Electrodes Coated with Charge-Different Polymer Films"; Sensors; Apr. 26, 2005; pp. 161-170; vol. 5; ISSN 1424-8220; MDPI.

"InNo-T Nitric Oxide Measurement System"; Warner Instruments; Bearing dates of 1998-2007; pp. 1-2; located at: http://www.warneronline.com/product_info.cfm?ID=220; printed on Oct. 24, 2007.

Keefer, Larry K.; "Nitric Oxide-Releasing Compounds: From Basic Research to Promising Drugs"; Chemtech; Aug. 1998; pp. 30-35 (pp. 1-8); vol. 28, No. 8; located at: http://pubs.acs.org/hotartcl/chemtech/98/aug/nitric.html; printed on Oct. 2, 2007; The American Chemical Society.

Khan, MA et al.; "The Effect of Superoxide Dismutase on Nitric Oxide-Mediated and Electrical Field-Stimulated Diabetic Rabbit Cavernosal Smooth Muscle Relaxation"; BJU Int.; Jan. 2001; pp. 98-103 (p. 1); vol. 87, No. 1; located at: http://www.pubmed.gov; printed on Sep. 27, 2007 (Abstract Only).

Kim, SC et al.; "Effects of Ultraviolet Light on the Tension of Isolated Human Cavernosal Smooth Muscle from Non-Diabetic and Diabetic Impotent Men"; Urol. Res.; 1997; pp. 149-152 (p. 1); vol. 25, No. 2; located at: http://www.pubmed.gov; printed on Sep. 27, 2007 (Abstract Only).

Kim, JH et al; "Mechanism of UV Light-Induced Photorelaxation in Isolated Rat Aorta"; J. Vet. Sci.; Dec. 2000; pp. 81-86 (p. 1); vol. 1, No. 2; located at: http://www.pubmed.gov; printed on Oct. 26, 2007 (Abstract Only).

Li, Chang Ming et al.; "Electrochemical Detection of Nitric Oxide on a SWCNT/RTIL Composite Gel Microelectrode"; Electroanalysis; 2006; pp. 713-718; vol. 18, No. 7; WILEY-VCH Verlag GmbH & Co. KGaA, Weinheim.

"Light-Emitting Diode (LED)"; Fiber Optics; Bearing a date of 2005; pp. 1-10; located at: http://www.fiber-optics.info/articles/LEDs.htm; printed on Oct. 6, 2007.

Lin, Hong-Yu et al.; "Side-Polished Multimode Fiber Biosensor Based on Surface Plasmon Resonance with Halogen Light"; Applied Optics; Feb. 10, 2007; pp. 800-806; vol. 46, No. 5; Optical Society of America.

Matthews, EK et al.; "Photon Pharmacology of an Iron-Sulphur Cluster Nitrosyl Compound Acting on Smooth Muscle"; Br. J. Pharmacol.; Sep. 1994; pp. 87-94 (p. 1); vol. 113, No. 1; located at: http://www.pubmed.gov; printed on Oct. 26, 2007 (Abstract Only).

Mendioroz, A. et al.; "Infrared to Visible and Ultraviolet Upconversion Processes in $Nd^{3+}$-Doped Potassium Lead Chloride Crystal"; Optical Materials; Sep. 2004; pp. 351-357 (p. 1); vol. 26, Issue 4; located at: http://www.sciencedirect.com; printed on Oct. 29, 2007 (Abstract Only).

Nablo, Brian J. et al.; "Inhibition of Implant-Associated Infections Via Nitric Oxide Release"; Biomaterials; Dec. 2005; pp. 6984-6990 (p. 1); vol. 26, Issue 34; located at: http://www.sciencedirect.com; printed on Oct. 26, 2007 (Abstract Only).

"NO Electrodes"; WPI-Europe-Biosensing-NO Electrodes; Bearing a date of Nov. 29, 2007; pp. 1-5; World Precision Instruments; located at: http://www.wpi-europe.com/products/biosensing/noelectrodes.htm; printed on Nov. 29, 2007.

"OL 770-LED: High-Speed LED Measurement System"; Bearing a date of 2001; pp. 1-6; located at: http://www.optroniclabs.com; Optronic Laboratories, Inc.

"Particulate Effects on Immunologic Function"; OST 1997AR; Bearing a date of 1997; pp. 1-2; located at: http://www.fda.gov/cdrh/ost/rpt97/OST1997AR9.HTML; printed on Oct. 16, 2007.

Peng, H. et al.; "Ultraviolet Light-Emitting Diodes Operating in the 340 nm Wavelength Range and Application to Time-Resolved Fluorescence Spectroscopy"; Applied Physics Letters; Aug. 23, 2004; pp. 1436-1438 (p. 1); vol. 85, Issue 8; located at: http://scitation.aip.org; printed on Oct. 26, 2007 (Abstract Only).

Pou, SJ et al.; "Biological Studies of a Nitroso Compound that Releases Nitric Oxide Upon Illumination"; Molecular Pharmacology; Oct. 1, 1994; pp. 709-715 (p. 1); vol. 46, Issue 4; located at: http://molpharm.aspetjournals.org/cgi/content/abstract/46/4/709; printed on Oct. 26, 2007 (Abstract Only).

"Probes for Nitric Oxide (NO) Research"; EMD-Calbiochem: Nitric Oxide Probes; Bearing a date of 2007; pp. 1-2; Calbiochem, Novabiochem, & Novagen; located at: http://www.emdbiosciences.com/html/cbc/nitric_oxide_probes.htm; printed on Nov. 29, 2007.

Räthel, Thomas R. et al.; "Application of 4,5-Diaminofluorescein to Reliably Measure Nitric Oxide Released from Endothelial Cells in Vitro"; Biological Procedures Online; Jun. 2, 2003; pp. 136-142; vol. 5, No. 1.

Rotta, J.C.G. et al.; "Nitric Oxide Release from the S-Nitrosothiol Zinc Phthalocyanine Complex by Flash Photolysis"; Brazilian Journal of Medical and Biological Research; 2003; pp. 587-594; vol. 36, No. 5; located at: http://www.scielo.br/pdf/bjmbr/v36n5/4604.pdf.

Seo, K.K. et al.; "Synergistic Effects of Sildenafil on Relaxation of Rabbit and Rat Cavernosal Smooth Muscles when Combined with Various Vasoactive Agents"; BJU International; 2001; pp. 596-601; vol. 88.

Singh, Ravinder Jit et al.; "Photosensitized Decomposition of S-Nitrosothiols and 2-Methyl-2-Nitrosopropane Possible Use for Site-Directed Nitric Oxide Production"; FEBS Letters; 1995; pp. 47-51; vol. 360; Federation of European Biochemical Societies.

Smith, DJ et al.; "Nitric Oxide-Releasing Polymers Containing the [N(O)NO]-Group"; J. Med. Chem.; Mar. 1, 1996; pp. 1148-1156 (p. 1); vol. 39, No. 5; located at: http://www.pubmed.gov; printed on Oct. 26, 2007 (Abstract Only).

Sonoki, T. et al.; "Detection of Inducible Nitric Oxide Synthase (iNOS) mRNA by RT-PCR in ATL Patients and HTLV-1 Infected Cell Lines: Clinical Features and Apoptosis by NOS Inhibitor"; Leukemia; 1999; pp. 713-718; vol. 13; Stockton Press.

Wadsworth, Roger et al.; "Physiologically Relevant Measurements of Nitric Oxide in Cardiovascular Research Using Electrochemical Microsensors"; Journal of Vascular Research; 2006; pp. 70-85; vol. 43; S. Karger AG, Basel.

Wang, Peng George et al.; "Nitric Oxide Donors: Chemical Activities and Biological Applications"; Chem. Rev.; 2002;pp. 1091-1134 (pp. 1-53); vol. 102, No. 4; American Chemical Society; located at: http://pubs.acs.org/cgi-bin/abstract.cgi/chreay/2002/102/i04/abs/cr0000401.html; printed on Oct. 26, 2007.

Wang, Tianlong et al.; "Inhaled Nitric Oxide in 2003: A Review of its Mechanisms of Action"; Canadian Journal of Anesthesia; 2003; pp. 839-846; vol. 50, No. 8.

Williamson, David; "Study: Nitric Oxide-Releasing Materials Might Reduce Medical Implant Infections"; UNC News Services; Sep. 7, 2001; pp. 1-2; No. 416; located at: http://www.unc.edu/news/archives/sep01/schoen090701.htm; printed on Oct. 4, 2007.

Xie, Rong-Jun; "Highly Efficient White-Light-Emitting Diodes Fabricated with Short-Wavelength Yellow Oxynitride Phosphors"; Applied Physics Letters; Mar. 6, 2006; pp. 101104.1-101104.3 (pp. 1-2); vol. 88; located at: http://scitation.aip.org/; printed on Oct. 26, 2007 (Abstract Only).

U.S. Appl. No. 12/928,029, Hyde et al.
U.S. Appl. No. 12/928,028, Hyde et al.
U.S. Appl. No. 12/927,610, Hyde et al.
Dictionary.com; "Patch"; printed on Jul. 20, 2012; pp. 1-8; located at http://dictionary.reference.com/browse/patch.
U.S. Appl. No. 13/452,502, Hyde et al.
Walt et al.; "Biological Warfare"; Analytical Chemistry; Dec. 1, 2000; pp. 738 A-47 A.

* cited by examiner

210 — one or more nitric oxide permeable housings that are configured to facilitate release of nitric oxide following photolysis of one or more photolyzable nitric oxide donors within the one or more nitric oxide permeable housings

| 302 one or more ports that facilitate release of nitric oxide from the one or more nitric oxide permeable housings | 304 one or more control units that control one or more ports that facilitate release of nitric oxide from the one or more nitric oxide permeable housings | 306 one or more electrical connectors that are configured for connection to one or more light sources | 308 one or more nitric oxide permeable membranes | 310 one or more windows that allow light to pass | 312 one or more quartz windows |

FIGS. 16A-16C
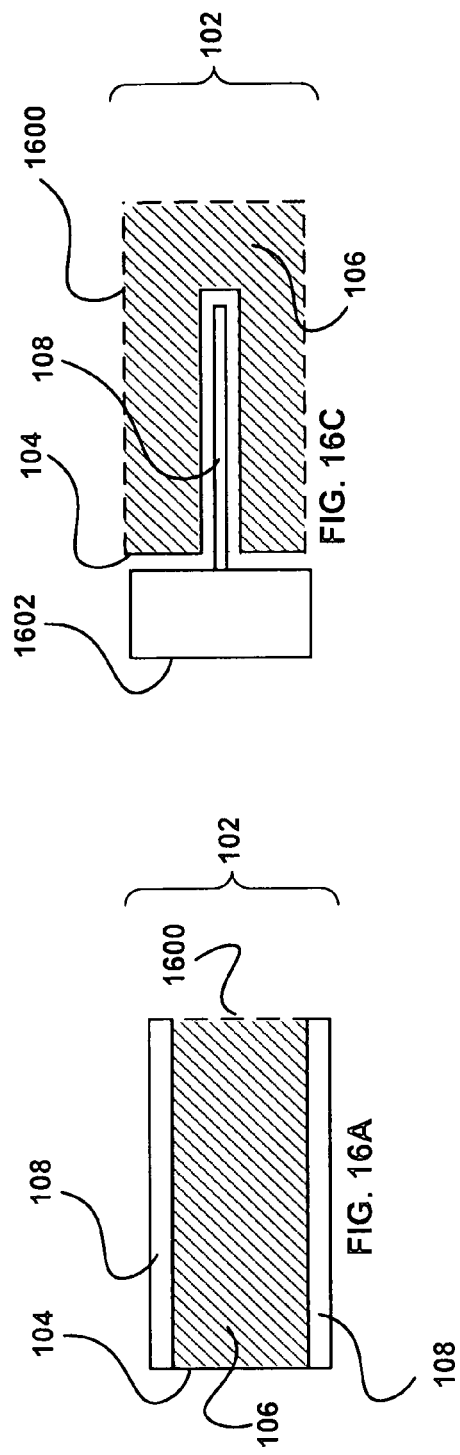
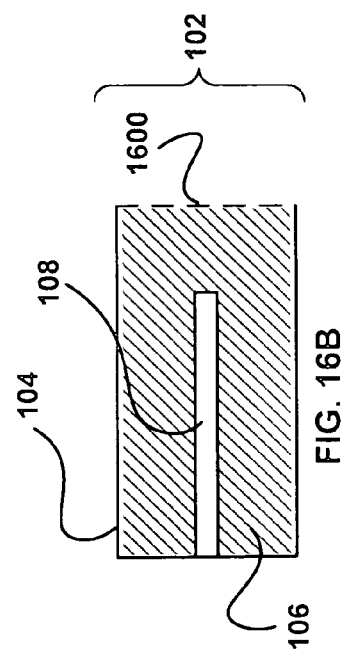

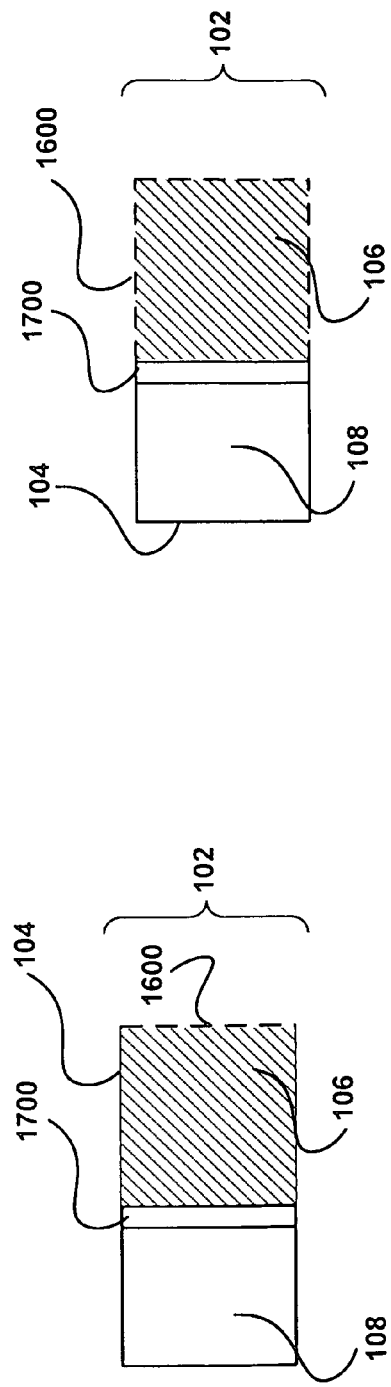
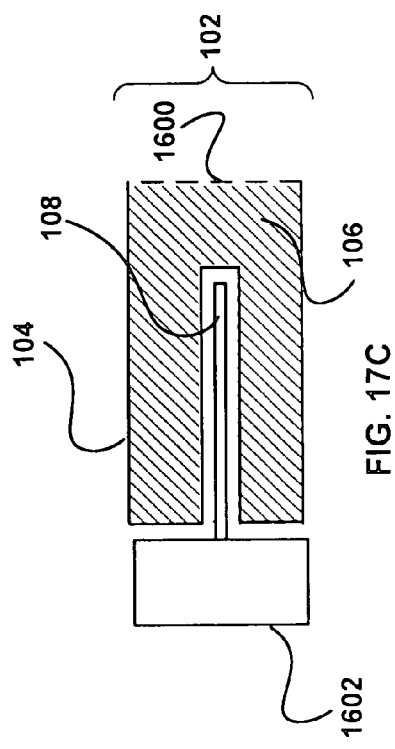
FIGS. 17A-17C

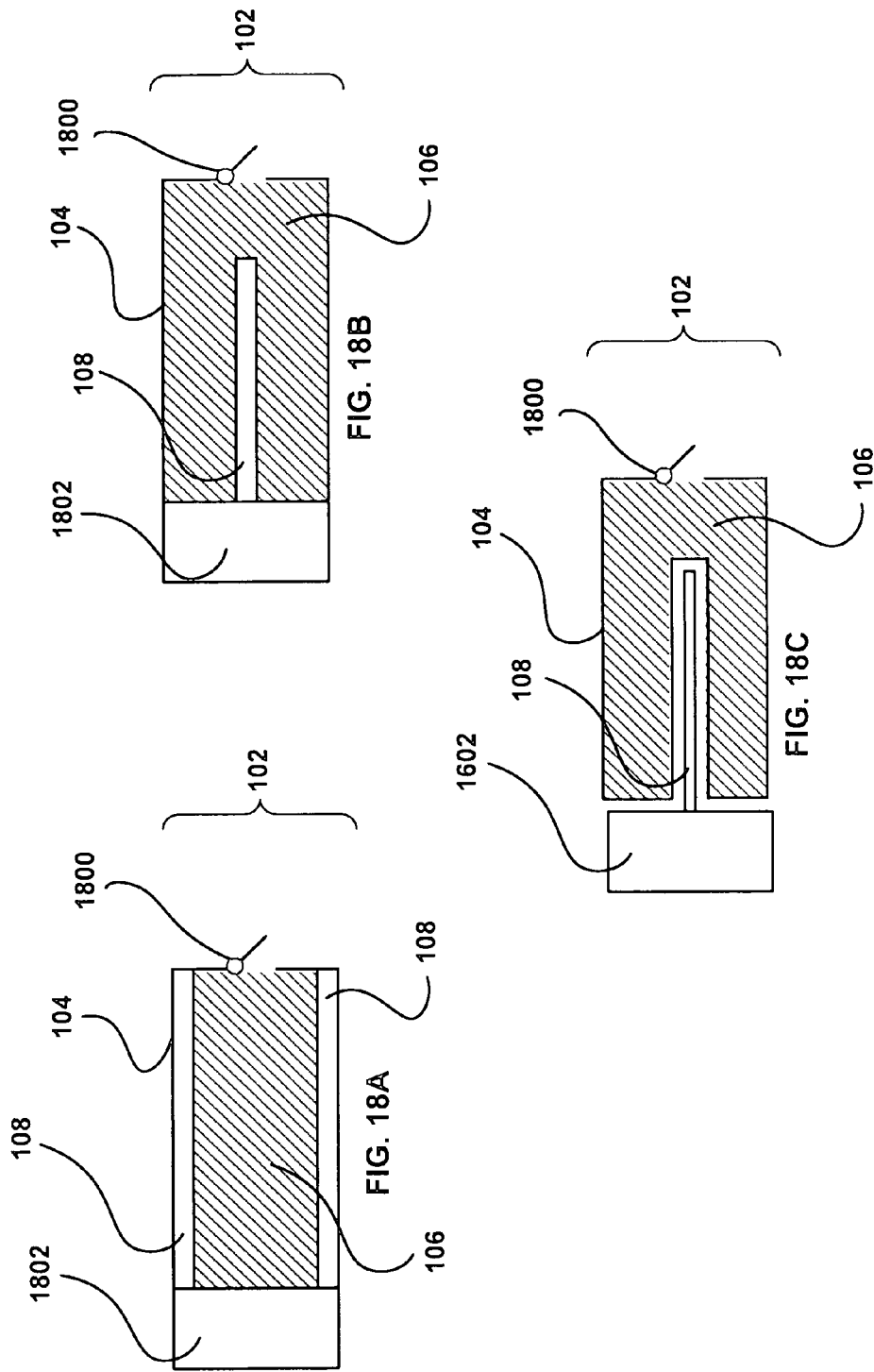

FIGS. 19A-19D
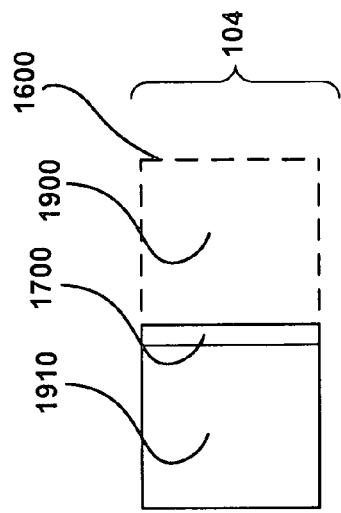
FIG. 19B
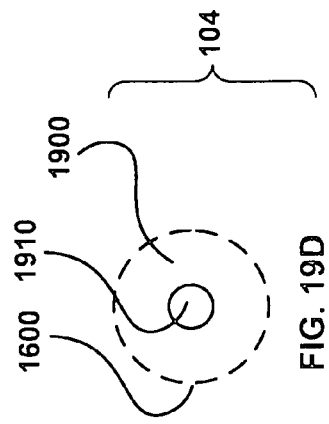
FIG. 19D
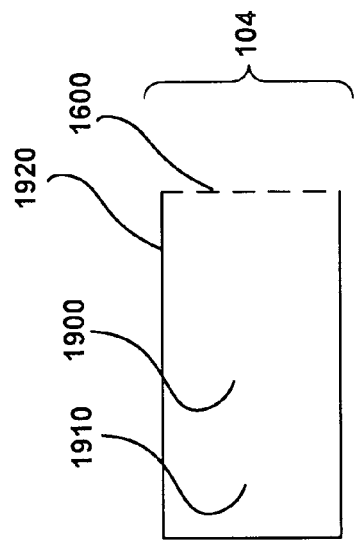
FIG. 19A
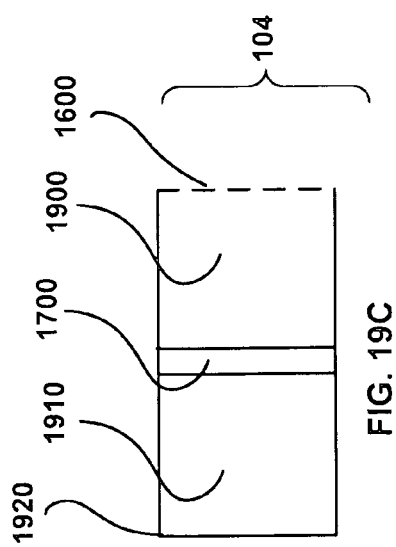
FIG. 19C

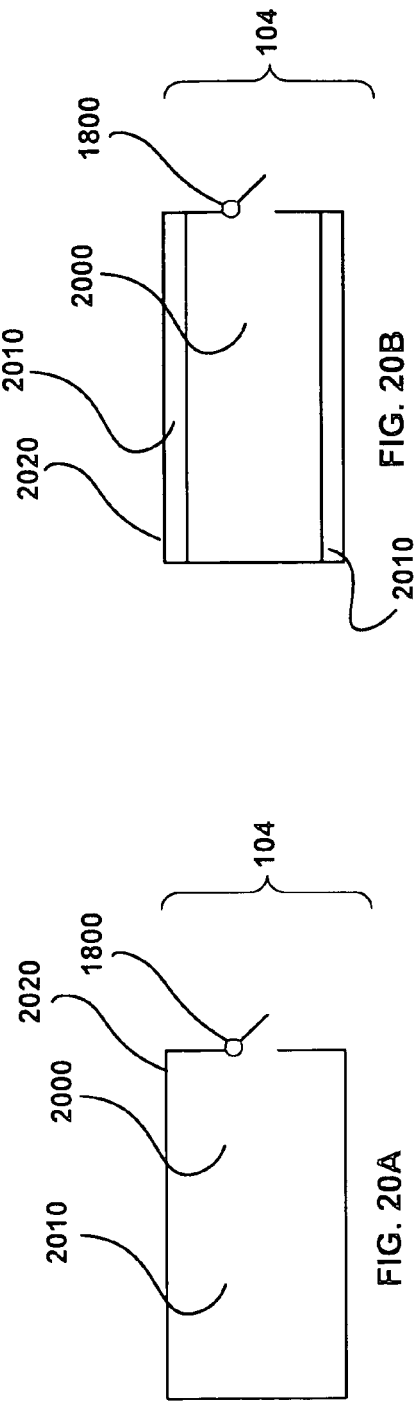
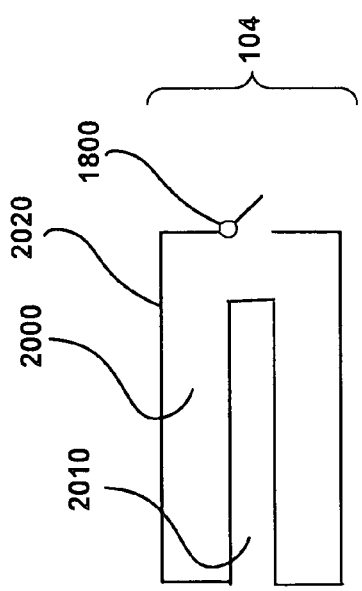
FIGS. 20A-20C

NITRIC OXIDE PERMEABLE HOUSINGS

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

For purposes of the USPTO extra-statutory requirements, the present application constitutes a continuation-in-part of U.S. patent application Ser. No. 11/981,743, entitled Methods and Systems for Use of Photolyzable Nitric Oxide Donors, naming Roderick A. Hyde, Muriel Y. Ishikawa and Lowell L. Wood, Jr. as inventors, filed 30 Oct. 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/998,864, entitled Systems and Devices that Utilize Photolyzable Nitric Oxide Donors, naming Roderick A. Hyde, Muriel Y. Ishikawa and Lowell L. Wood, Jr. as inventors, filed 30 Nov. 2007, now U.S. Pat. No. 8,221,690 which is currently, or is an application of which a currently co-pending application is entitled to the benefit of the filing date.

For purposes of the USPTO extra-statutory requirements, the present application constitutes a continuation-in-part of U.S. patent application Ser. No. 12/005,045, entitled Systems and Devices Related to Nitric Oxide Releasing Materials, naming Roderick A. Hyde, Muriel Y. Ishikawa, Leif T. Stordal and Lowell L. Wood, Jr. as inventors, filed 21 Dec. 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/005,065, entitled Devices and Systems that Deliver Nitric Oxide, naming Roderick A. Hyde, Muriel Y. Ishikawa, Leif T. Stordal and Lowell L. Wood, Jr. as inventors, filed 21 Dec. 2007, now U.S. Pat. No. 7,862,598 which is currently, or is an application of which a currently co-pending application is entitled to the benefit of the filing date.

For purposes of the USPTO extra-statutory requirements, the present application constitutes a continuation-in-part of U.S. patent application Ser. No. 12/005,132, entitled Nitric Oxide Sensors and Systems, naming Roderick A. Hyde, Muriel Y. Ishikawa, Leif T. Stordal and Lowell L. Wood, Jr. as inventors, filed 21 Dec. 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/005,136, entitled Devices Configured to Facilitate Release of Nitric Oxide, naming Roderick A. Hyde, Muriel Y. Ishikawa and Lowell L. Wood, Jr. as inventors, filed 21 Dec. 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/005,170, entitled Condoms Configured to Facilitate Release of Nitric Oxide, naming Roderick A. Hyde, Muriel Y. Ishikawa and Lowell L. Wood, Jr. as inventors, filed 21 Dec. 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/006,090, entitled Sleeves Configured to Facilitate Release of Nitric Oxide, naming Roderick A. Hyde, Muriel Y. Ishikawa and Lowell L. Wood, Jr. as inventors, filed 28 Dec. 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/006,049, entitled Substrates for Nitric Oxide Releasing Devices, naming Roderick A. Hyde, Muriel Y. Ishikawa, Leif T. Stordal and Lowell L. Wood, Jr. as inventors, filed 28 Dec. 2007, now abandoned which is currently, or is an application of which a currently co-pending application is entitled to the benefit of the filing date.

For purposes of the USPTO extra-statutory requirements, the present application constitutes a continuation-in-part of U.S. patent application Ser. No. 12/006,069, entitled Nitric Oxide Permeable Housings, naming Roderick A. Hyde, Muriel Y. Ishikawa and Lowell L. Wood, Jr. as inventors, filed 28 Dec. 2007, now abandoned which is currently, or is an application of which a currently co-pending application is entitled to the benefit of the filing date.

For purposes of the USPTO extra-statutory requirements, the present application constitutes a continuation-in-part of U.S. patent application Ser. No. 12/008,708, entitled Substrates for Nitric Oxide Releasing Devices, naming Roderick A. Hyde, Muriel Y. Ishikawa, Leif T. Stordal and Lowell L. Wood, Jr. as inventors, filed 11 Jan. 2008, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, Benefit of Prior-Filed Application, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

TECHNICAL FIELD

The present disclosure relates to an apparatus that includes one or more nitric oxide permeable housings.

SUMMARY

In some embodiments an apparatus is provided that includes one or more nitric oxide permeable housings that are configured to facilitate release of nitric oxide following photolysis of one or more photolyzable nitric oxide donors within the one or more nitric oxide permeable housings. The apparatus may optionally include one or more photolyzable nitric oxide donors. The apparatus may optionally include one or more light sources that are configured to emit light that facilitates release of nitric oxide from the one or more photolyzable nitric oxide donors. In addition to the foregoing, other aspects are described in the claims, drawings, and text forming a part of the present disclosure.

In some embodiments a system is provided that includes circuitry for operating one or more nitric oxide permeable housings that are configured to facilitate release of nitric oxide following photolysis of one or more photolyzable nitric oxide donors within the one or more nitric oxide permeable housings. The system may optionally include circuitry for operating one or more light sources that are configured to emit light that facilitates release of nitric oxide from the one or more photolyzable nitric oxide donors. In addition to the foregoing, other aspects are described in the claims, drawings, and text forming a part of the present disclosure.

In some embodiments a system is provided that includes means for operating one or more nitric oxide permeable housings that are configured to facilitate release of nitric oxide following photolysis of one or more photolyzable nitric oxide donors within the one or more nitric oxide permeable housings. The system may optionally include means for operating one or more light sources that are configured to emit light that facilitates release of nitric oxide from one or more photolyzable nitric oxide donors. In addition to the foregoing, other aspects are described in the claims, drawings, and text forming a part of the present disclosure.

In some embodiments a system is provided that includes a signal-bearing medium bearing one or more instructions for operating one or more nitric oxide permeable housings that are configured to facilitate release of nitric oxide following photolysis of one or more photolyzable nitric oxide donors within the one or more nitric oxide permeable housings. The system may optionally include one or more instructions for operating one or more light sources that are configured to emit light that facilitates release of nitric oxide from the one or more photolyzable nitric oxide donors. In addition to the foregoing, other aspects are described in the claims, drawings, and text forming a part of the present disclosure.

In some embodiments, means include but are not limited to circuitry and/or programming for effecting the herein referenced functional aspects; the circuitry and/or programming can be virtually any combination of hardware, software, and/or firmware configured to effect the herein referenced functional aspects depending upon the design choices of the system designer. In addition to the foregoing, other system aspects means are described in the claims, drawings, and/or text forming a part of the present disclosure.

In some embodiments, related systems include but are not limited to circuitry and/or programming for effecting the herein referenced method aspects; the circuitry and/or programming can be virtually any combination of hardware, software, and/or firmware configured to effect the herein referenced method aspects depending upon the design choices of the system designer. In addition to the foregoing, other system aspects are described in the claims, drawings, and/or text forming a part of the present application.

The foregoing summary is illustrative only and is not intended to be in any way limiting. In addition to the illustrative aspects, embodiments, and features described above, further aspects, embodiments, and features will become apparent by reference to the drawings, claims, and the following detailed description.

BRIEF DESCRIPTION OF THE FIGURES

FIG. 3 illustrates alternate embodiments of module 210 of embodiment 200 of apparatus 102 within system 100.

FIGS. 16A-16C illustrate embodiments of a nitric oxide permeable housing 104 within system 100.

FIGS. 17A-17C illustrate embodiments of a nitric oxide permeable housing 104 within system 100.

FIGS. 18A-18C illustrate embodiments of a nitric oxide permeable housing 104 within system 100.

FIGS. 19A-19D illustrate embodiments of a nitric oxide permeable housing 104 within system 100.

FIGS. 20A-20C illustrate embodiments of a nitric oxide permeable housing 104 within system 100.

DETAILED DESCRIPTION

Figure 1:
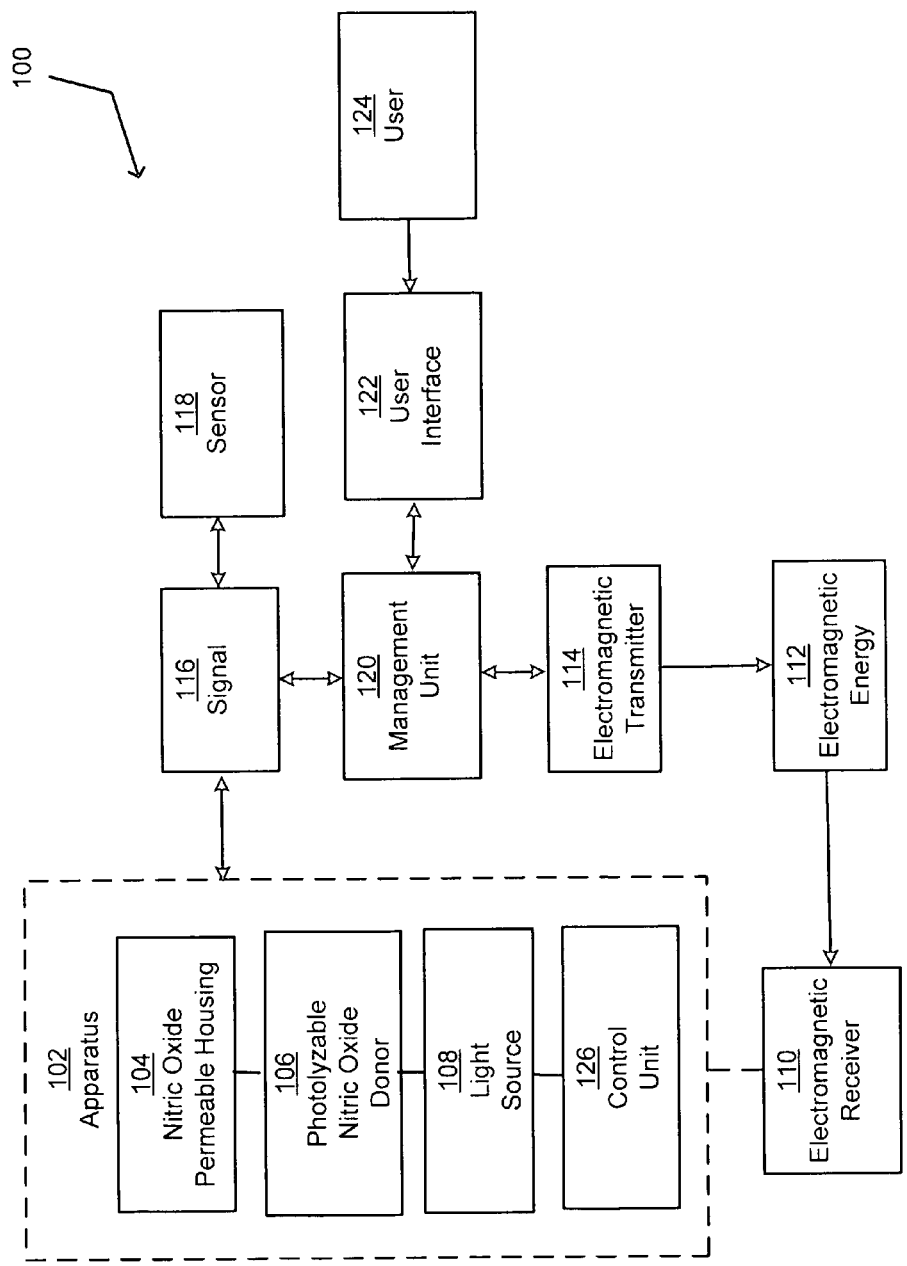
FIG. 1 illustrates an example system 100 in which embodiments may be implemented.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

FIG. 1 illustrates a system 100 in which embodiments may be implemented. System 100 may include an apparatus 102 that includes a nitric oxide permeable housing 104. In some embodiments, an apparatus 102 may be associated with one or more photolyzable nitric oxide donors 106. In some embodiments, an apparatus 102 may be associated with one or more light sources 108. In some embodiments, an apparatus 102 may be associated with one or more sensors 118. In some embodiments, an apparatus 102 may be configured to receive one or more signals 116. In some embodiments, one or more signals 116 may include instructions for operating one or more light sources 108 associated with the apparatus 102. In some embodiments, an apparatus 102 may be configured to transmit one or more signals 116. In some embodiments, system 100 may include one or more management units 120 that are configured to transmit and/or receive one or more signals 116. In some embodiments, system 100 may include one or more management units 120 that are operably associated with one or more user interfaces 122. In some embodiments, system 100 may include one or more management units 120 that are operably associated with one or more electromagnetic transmitters 114. In some embodiments, system 100 may include one or more electromagnetic transmitters 114 that transmit electromagnetic energy 112 that may be received by one or more light sources 108.

Apparatus

System 100 includes one or more apparatuses 102. An apparatus 102 may be configured in numerous ways. In some embodiments, an apparatus 102 may be configured for implantation into a user 124. For example, in some embodiments, an apparatus 102 may be configured for implantation into the genital region of a user 124. In some embodiments, an apparatus 102 may be configured for application to an inside surface of a user 124. For example, in some embodiments, an apparatus 102 may be configured for insertion into the urethra of a user 124. In some embodiments, an apparatus 102 may be configured for vaginal insertion into a user 124. In some embodiments, an apparatus 102 may be configured for application to an outside surface of a user 124. For example, in some embodiments, an apparatus 102 may be configured for application to the skin of a user 124. Accordingly, an apparatus 102 may be configured in numerous ways to deliver nitric oxide to a surface or region of a user 124. In some embodiments, an apparatus 102 may be configured to deliver nitric oxide as a therapeutic agent. In some embodiments, an apparatus 102 may be configured to deliver nitric oxide as a sanitizing agent. For example, in some embodiments, an apparatus 102 may be configured to deliver nitric oxide to the surface of a table, a chair, to surgical instruments, and the like. In some embodiments, an apparatus 102 may be incorporated into clothing. For example, in some embodiments, one or more devices 102 may be incorporated into a glove, a mitten, a hood, a mask, a sock, a shirt, a sheet, a bandage, tape, and the like.

Photolyzable Nitric Oxide Donor

Numerous photolyzable nitric oxide donors 106 may be used within system 100. Examples of such photolyzable nitric oxide donors 106 include, but are not limited to, diazeniumdiolates (e.g., U.S. Pat. Nos. 7,105,502; 7,122,529; 6,673,338; herein incorporated by reference), trans-[RuCl([15]aneN4)NO]+2 (Ferezin et al., Nitric Oxide, 13:170-175 (2005), Bonaventura et al., Nitric Oxide, 10:83-91 (2004)), nitrosyl ligands (e.g., U.S. Pat. No. 5,665,077; herein incorporated by reference, Chmura et al., Nitric Oxide, 15:370-379 (2005), Flitney et al., Br. J. Pharmacol., 107:842-848 (1992), Flitney et al., Br. J. Pharmacol., 117:1549-1557 (1996), Matthews et al., Br. J. Pharmacol., 113:87-94 (1994)), 6-Nitrobenzo[a]pyrene (e.g., Fukuhara et al., J. Am. Chem. Soc., 123:8662-8666 (2001)), S-nitroso-glutathione (e.g., Rotta et al., Braz. J. Med. Res., 36:587-594 (2003), Flitney and Megson, J. Physiol., 550:819-828 (2003)), S-nitrosothiols (e.g., Andrews et al., British Journal of Pharmacology, 138:932-940 (2003), Singh et al., FEBS Lett., 360:47-51 (1995)), 2-Methyl-2-nitrosopropane (e.g., Pou et al., Mol. Pharm., 46:709-715 (1994), Wang et al., Chem. Rev., 102:1091-1134 (2002)), imidazolyl derivatives (e.g., U.S. Pat. No. 5,374,710; herein incorporated by reference). In some embodiments, one or more photolyzable nitric oxide donors 106 may be used in association with additional nitric oxide donors that are not photolyzable. In some embodiments, one or more photolyzable nitric oxide donors 106 may be used in association with additional agents. Examples of such additional agents include, but are not limited to, enzyme inhibitors (e.g., U.S. Pat. No. 6,943,166; herein incorporated by reference), agents that increase the effects and/or concentration of nitric oxide (e.g., methylene blue and N(w)-nitro-L-arginine (L-NOARG) (see Chen and Gillis, Biochem. Biophys. Res. Commun., 190, 559-563 (1993) and Kim et al., J. Vet. Sci., 1:81-86 (2000)), L-arginine (e.g., U.S. Published Patent Application No. 20020068365 and U.S. Pat. No. 6,635,273; herein incorporated by reference), agents that stabilize nitric oxide donors (e.g., dimethyl sulfoxide and ethanol), agents that increase the half life of nitric oxide (e.g., U.S. Published Patent Application No. 20030039697; herein incorporated by reference), and the like.

Nitric Oxide Permeable Layer

System 100 may include one or more nitric oxide permeable layers. In some embodiments, one or more nitric oxide permeable layers may be associated with a nitric oxide permeable housing 104. In some embodiments, a nitric oxide permeable housing 104 may include one or more portions that include one or more nitric oxide permeable layers and one or more portions that include one or more nitric oxide impermeable layers.

A nitric oxide permeable layer may be constructed of numerous types of materials and combinations of materials. Examples of such materials include, but are not limited to, ceramics, polymeric materials, metals, plastics, and the like. In some embodiments, a nitric oxide permeable layer may include numerous combinations of materials. For example, in some embodiments, a nitric oxide permeable layer may include a nitric oxide impermeable material that is coupled to a nitric oxide permeable material. In some embodiments, a nitric oxide permeable layer may include one or more nitric oxide permeable membranes (e.g., U.S. Patent Application No. 20020026937). In some embodiments, a nitric oxide permeable layer may include a selectively permeable membrane. For example, in some embodiments, a nitric oxide permeable layer may include a selectively permeable membrane that is a hydrophilic polyester co-polymer membrane system that includes a copolymer with 70% polyester and 30% polyether (e.g., Sympatex™ 10 µm membrane, see Hardwick et al., Clinical Science, 100:395-400 (2001)). In some embodiments, a nitric oxide permeable layer may include one or more woven materials that are permeable to nitric oxide. Accordingly, in some embodiments, a nitric oxide permeable layer may include numerous types of woven glasses and/or ceramics that are permeable to nitric oxide. In some embodiments, a nitric oxide permeable layer may include a porous metal portion that is permeable to nitric oxide. In some embodiments, a nitric oxide permeable layer may include a nitric oxide permeable coating (e.g., U.S. Patent Application Nos. 20050220838 and 20030093143).

Light Source

Numerous light sources 108 may be used within system 100. In some embodiments, one or more light sources 108 may be used to facilitate release of nitric oxide from one or more photolyzable nitric oxide donors 106. In some embodiments, one or more light sources 108 may be configured to emit light of multiple wavelengths. In some embodiments, one or more light sources 108 may be configured to emit light that is selected to facilitate release of nitric oxide from one or more photolyzable nitric oxide donors 106. For example, in some embodiments, one or more light sources 108 may be configured to emit one or more wavelengths of light that are selected to facilitate release of nitric oxide from one or more identified photolyzable nitric oxide donors 106. In some embodiments, one or more light sources 108 may emit one or more wavelengths of light that are selected based on the absorption spectrum of one or more photolyzable nitric oxide donors 106. In some embodiments, one or more light sources 108 may emit one or more wavelengths of light that are selected based on decomposition of one or more photolyzable nitric oxide donors 106. For example, in some embodiments, one or more light sources 108 may be configured to emit one or more wavelengths of light that cause decomposition of one or more photolyzable nitric oxide donors 106 without causing injury to adjacent structures and/or tissues. In some embodiments, a first light source 108 may be configured to emit one or more wavelengths of light that cause a first photolyzable nitric oxide donor 106 to release nitric oxide and a second light source 108 may be configured to emit one or more wavelengths of light that cause a second photolyzable nitric oxide donor 106 to release nitric oxide. Accordingly, numerous light sources 108 may be associated with a nitric oxide permeable housing 104.

In some embodiments, one or more light sources 108 may include one or more quantum dots (e.g., U.S. Pat. No. 7,235,361). For example, in some embodiments, one or more light sources 108 may be configured to emit one or more wavelengths of light that are absorbed by one or more quantum dots. In some embodiments, one or more quantum dots may be configured to absorb light and then emit one or more wavelengths of light that cause release of nitric oxide from one or more photolyzable nitric oxide donors 106. Accordingly, in some embodiments, emission from one or more first quantum dots may be tuned to facilitate release of nitric oxide from one or more first photolyzable nitric oxide donors 106 and emission from one or more second quantum dots may be tuned to facilitate release of nitric oxide from one or more second photolyzable nitric oxide donors 106.

In some embodiments, one or more light sources 108 may be remotely controlled. For example, in some embodiments, one or more light sources 108 may be configured to receive one or more signals 116 that include instructions for operation of the one or more light sources 108. Such instructions may be associated with emission of light, non-emission of light, time when light is emitted, length of light emission, intensity of light emission, wavelengths of emitted light, and the like.

In some embodiments, light sources 108 may be configured to include one or more control units. In some embodiments, one or more light sources 108 may be configured to include a switch that may be used to turn the light source 108 on and off. For example, in some embodiments, a light source 108 may be configured to include a push button switch to turn the light source 108 on and off.

In some embodiments, one or more light sources 108 may include one or more light emitters that are coupled to one or more electromagnetic receivers 110. The one or more electromagnetic receivers 110 may be configured to couple with one or more electromagnetic transmitters 114 that produce one or more electromagnetic fields that induce an electrical current to flow in the one or more electromagnetic receivers 110 to energize the light emitters (e.g., U.S. Pat. No. 5,571,152; herein incorporated by reference). Accordingly, in some embodiments, one or more light sources 108 may be configured such that they are not directly coupled to an energy source.

A light source 108 may be configured to emit numerous types of light. In some embodiments, emitted light may be visible light. In some embodiments, emitted light may be infrared light. In some embodiments, emitted light may be ultraviolet light. In some embodiments, emitted light may be substantially any combination of visible light, infrared light, and/or ultraviolet light. In some embodiments, one or more light sources 108 may emit fluorescent light. In some embodiments, one or more light sources 108 may emit phosphorescent light.

In some embodiments, one or more light sources 108 may be configured to emit light continuously. In some embodiments, one or more light sources 108 may be configured to emit light as a pulse. In some embodiments, one or more light sources 108 may be configured to emit light as a flash. In some embodiments, one or more light sources 108 may be configured to emit light continuously, as a pulse, as a flash, or substantially any combination thereof.

In some embodiments, one or more light emitters and/or light sources 108 may be configured to provide for upconversion of energy. In some embodiments, infrared light may be upconverted to visible light (e.g., Mendioroz et al., Optical Materials, 26:351-357 (2004). In some embodiments, infrared light may be upconverted to ultraviolet light (e.g., Mendioroz et al., Optical Materials, 26:351-357 (2004). In some embodiments, one or more light sources 108 may include one or more rare-earth materials (e.g., ytterbium-erbium, ytterbium-thulium, or the like) that facilitate upconversion of energy (e.g., U.S. Pat. No. 7,088,040; herein incorporated by reference). For example, in some embodiments, one or more light sources 108 may be associated with $Nd^{3+}$ doped $KPb_2Cl_5$ crystals. In some embodiments, one or more light sources 108 may be associated with thiogallates doped with rare earths, such as $CaGa_2S_4:Ce^{3+}$ and $SrGa_2S_4:Ce^{3+}$. In some embodiments, one or more light sources 108 may be associated with aluminates that are doped with rare earths, such as $YAlO_3:Ce^{3+}$, $YGaO_3:Ce^{3+}$, $Y(Al,Ga)O_3:Ce^{3+}$, and orthosilicates $M_2SiO_5:Ce^{3+}$ (M:Sc, Y, Sc) doped with rare earths, such as, for example, $Y_2SiO_5:Ce^{3+}$. In some embodiments, yttrium may be replaced by scandium or lanthanum (e.g., U.S. Pat. Nos. 6,812,500 and 6,327,074; herein incorporated by reference). Numerous materials that may be used to upconvert energy have been described (e.g., U.S. Pat. Nos. 5,956,172; 5,943,160; 7,235,189; 7,215,687; herein incorporated by reference).

Electromagnetic Receiver

Numerous types of electromagnetic receivers 110 may be used within system 100. In some embodiments, one or more electromagnetic receivers 110 may be used to electromagnetically couple power to energize one or more light sources 108 from an external power supply. Methods to construct such electromagnetic receivers 110 have been described (e.g., U.S. Pat. No. 5,571,152). Briefly, in some embodiments, one or more electromagnetic receivers 110 may be associated with one or more rectifier chips. The one or more electromagnetic receivers 110 may include one or more cores about which are wrapped an electrical conductor. In some embodiments, cores may comprise a material, such as a ferrite material, due to its relatively high magnetic permeability and low magnetic hysteresis. However, other materials can be used for this purpose. In some embodiments, the electromagnetic receiver 110 may be operably coupled to a light emitting diode.

Electromagnetic Transmitter

Numerous types of electromagnetic transmitters 114 may be used within system 100. Methods to construct electromagnetic transmitters 114 have been described (e.g., U.S. Pat. No. 5,571,152). Briefly, in some embodiments, the electromagnetic transmitter 114 may include a ferrite core around which is wrapped an electrical conductor. Other types of material having high magnetic permeability and relatively low magnetic hysteresis may be used for the core. Insulating tape may be wrapped around the electrical conductor, or the electromagnetic transmitter 114 may be dipped in a resin to form a coating that stabilizes and fixes the electrical conductor on the core. A return lead from one end of the electrical conductor may include one of two leads that are coupled to an AC power supply.

Electromagnetic Energy

Electrical power may be electromagnetically coupled from one or more electromagnetic transmitters 114 with one or more electromagnetic receivers 110. Accordingly, electrical power that is transferred to the one or more electromagnetic receivers 110 may be used to power one or more light emitters. Methods and devices that may be used to transmit electrical power to a light emitter have been described (e.g., U.S. Pat. No. 5,571,152).

Transmitter

The system 100 may include one or more transmitters. In some embodiments, an apparatus 102 may include one or more transmitters that transmit one or more signals 116 that are received by one or more management units 120. In some embodiments, system 100 may include one or more transmitters that transmit one or more signals 116 that are received by one or more apparatuses 102. Numerous types of transmitters may be used in association with system 100. Examples of such transmitters include, but are not limited to, transmitters that transmit one or more optical signals 116, radio signals 116, wireless signals 116, hardwired signals 116, infrared signals 116, ultrasonic signals 116, acoustic signals 116, and the like (e.g., U.S. Pat. Nos. RE 39,785; 7,260,768; 7,260,764; 7,260,402; 7,257,327; 7,215,887; 7,218,900; herein incorporated by reference). In some embodiments, one or more transmitters may transmit one or more signals 116 that are encrypted. Numerous types of transmitters are known and have been described (e.g., U.S. Pat. Nos. and Published U.S. Pat. Nos. 7,236,595; 7,260,155; 7,227,956; US 2006/0280307; herein incorporated by reference).

Management Unit

System 100 may include one or more management units 120. In some embodiments, one or more management units 120 may be associated with one or more apparatuses 102. For example, in some embodiments, one or more management units 120 may be configured to regulate the operation of one or more light sources 108 that are associated with an apparatus 102. In some embodiments, one or more management units 120 may be configured to receive one or more signals 116 from one or more sensors 118. In some embodiments, one or more management units 120 may be configured to receive one or more signals 116 from one or more light sources 108 that are associated with an apparatus 102. Accordingly, in some embodiments, one or more management units 120 may be used to regulate the operation of one or more light sources 108 associated with an apparatus 102. In some embodiments, a management unit 120 may include memory. In some embodiments, a management unit 120 may include one or more programs that provide instructions for controlling an apparatus 102.

Receiver

System 100 may include one or more receivers. In some embodiments, one or more receivers may be associated with an apparatus 102. In some embodiments, one or more receivers may be associated with one or more light sources 108. In some embodiments, one or more receivers may be associated with one or more sensors 118. Numerous types of receivers may be used in association with system 100. Examples of such receivers include, but are not limited to, receivers that receive one or more optical signals 116, radio signals 116, wireless signals 116, hardwired signals 116, infrared signals 116, ultrasonic signals 116, acoustic signals 116, and the like. Such receivers are known and have been described (e.g., U.S. Pat. Nos. RE 39,785; 7,218,900; 7,254,160; 7,245,894; 7,206,605; herein incorporated by reference).

Signal

Numerous types of signals 116 may be used in association with system 100. Examples of such signals 116 include, but are not limited to, optical signals 116, radio signals 116, wireless signals 116, hardwired signals 116, infrared signals 116, ultrasonic signals 116, and the like. In some embodiments, one or more signals 116 may not be encrypted. In some embodiments, one or more signals 116 may be encrypted. In some embodiments, one or more signals 116 may be sent through use of a secure mode of transmission. In some embodiments, one or more signals 116 may be coded for receipt by a specific user 124. In some embodiments, such code may include anonymous code that is specific for a user 124. Accordingly, information included within one or more signals 116 may be protected against being accessed by others who are not the intended recipient.

User

An apparatus 102 may be used to deliver nitric oxide to a user 124. In some embodiments, a user 124 may be a human. In some embodiments, a user 124 may be a human male. In some embodiments, an apparatus 102 may be used to deliver nitric oxide to a user 124 to treat sexual dysfunction. In some embodiments, an apparatus 102 may be used to treat male erectile disorder. In some embodiments, sexual dysfunction may be due to a physical condition. For example, in some embodiments, sexual dysfunction may result from surgery, a physical injury, pharmaceutical use, age, or the like. In some embodiments, sexual dysfunction may be due to a mental condition. For example, in some embodiments, sexual dysfunction may be due to depression, lack of interest, insecurity, anxiety, or the like. In some embodiments, an apparatus 102 may deliver nitric oxide to increase sexual performance and/or pleasure. In some embodiments, an apparatus 102 may be configured to deliver nitric oxide to the skin of a user 124. In some embodiments, such delivery may be for cosmetic purposes. In some embodiments, such delivery may be for therapeutic purposes. For example, in some embodiments, an apparatus 102 may be used to deliver nitric oxide to a skin lesion, such as a skin ulcer, a burn, a cut, a puncture, a laceration, a blunt trauma, an acne lesion, a boil, and the like. In some embodiments, an apparatus 102 may be used to deliver nitric oxide to a skin surface to increase the expression of endogenous collagenase. In some embodiments, an apparatus 102 may be used to deliver nitric oxide to a skin surface to regulate the formation of collagen. In some embodiments, an apparatus 102 may be used to deliver nitric oxide to reduce inflammation (e.g., reduce exudate secretion) at the site of a lesion (e.g., U.S. Patent Application No. 2007/0088316). In some embodiments, an apparatus 102 may be used to deliver nitric oxide to reduce the microbial burden within a wound site. For example, in some embodiments, an apparatus 102 may be used to deliver nitric oxide as an antibacterial agent against methicillin-resistant *Staphylococcus aureus*. An apparatus 102 may deliver nitric oxide to a user 124 at numerous concentrations. For example, in some embodiments, nitric oxide may be delivered at a concentration ranging from about 160 ppm to about 400 ppm. Such concentrations may be used without inducing toxicity in the healthy cells around a wound site (e.g., U.S. Patent Application No. 2007/0088316).

User Interface/User

System 100 may include numerous types of user interfaces 122. For example, one or more users 124 may interact through use of numerous user interfaces 122 that utilize hardwired methods, such as through use of an on/off switch, a push button, a keyboard, and the like. In some embodiments, the user interface 122 may utilize wireless methods, such as methods that utilize a transmitter and receiver, utilize the internet, and the like.

Figure 2:
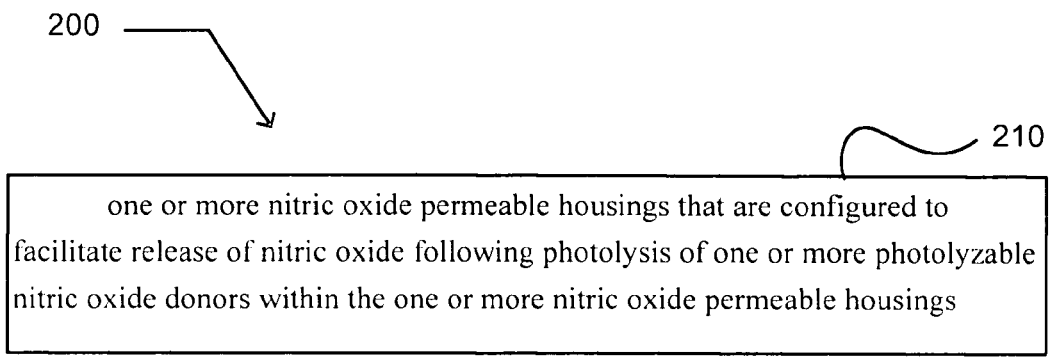
FIG. 2 illustrates embodiment 200 of apparatus 102 within system 100.

FIG. 2 illustrates embodiment 200 of an apparatus 102 within system 100. In FIG. 2, discussion and explanation may be provided with respect to the above-described example of FIG. 1, and/or with respect to other examples and contexts. However, it should be understood that the modules may execute operations in a number of other environments and contexts, and/or modified versions of FIG. 1. Also, although the various modules are presented in the sequence(s) illustrated, it should be understood that the various modules may be configured in numerous orientations.

The embodiment 200 may include module 210 that includes one or more nitric oxide permeable housings that are configured to facilitate release of nitric oxide following photolysis of one or more photolyzable nitric oxide donors within the one or more nitric oxide permeable housings. In some embodiments, a nitric oxide permeable housing 104 may include one or more nitric oxide permeable housings 104 that are configured to facilitate release of nitric oxide following photolysis of one or more photolyzable nitric oxide donors 106 within the one or more nitric oxide permeable housings. In some embodiments, a nitric oxide permeable housing 104 may include one or more light sources 108. In some embodiments, a nitric oxide permeable housing 104 may include one or more light sources 108 that are configured to emit light that facilitates release of nitric oxide from one or more photolyzable nitric oxide donors 106. In some embodiments, a nitric oxide permeable housing 104 may include one or more photolyzable nitric oxide donors 106. In some embodiments, a nitric oxide permeable housing 104 may be configured for implantation within a user 124. For example, in some embodiments, a nitric oxide permeable housing 104 may be configured to facilitate delivery of nitric oxide to the genital region of a user 124. In some embodiments, a nitric oxide permeable housing 104 may be configured to facilitate delivery of nitric oxide to the vasculature of a user 124. In some embodiments, a nitric oxide permeable housing 104 may be configured to facilitate delivery of nitric oxide to a surface. In some embodiments, a nitric oxide permeable housing 104 may be configured to be included within a bandage, a patch, tape, clothing, and the like. In some embodiments, a nitric oxide permeable housing 104 may include one or more nitric oxide permeable layers. In some embodiments, a nitric oxide permeable housing 104 may include one or more valves that are configured to provide for passage of nitric oxide from the nitric oxide permeable housing 104. In some embodiments, a nitric oxide permeable housing 104 may include one or more controllable valves that are configured to provide for passage of nitric oxide from the nitric oxide permeable housing 104. Accordingly, in some embodiments, a nitric oxide permeable housing 104 may include one or more control units. In some embodiments, one or more control units may be configured to control one or more valves. In some embodiments, one or more control units may be configured to control one or more light sources 108.

FIG. 3 illustrates alternative embodiments of embodiment 200 of an apparatus 102 within system 100 of FIG. 2. FIG. 3 illustrates example embodiments of module 210 of an apparatus 102. Additional embodiments may include an embodiment 302, an embodiment 304, an embodiment 306, an embodiment 308, an embodiment 310, and/or an embodiment 312.

At embodiment 302, module 210 may include one or more ports that facilitate release of nitric oxide from the one or more nitric oxide permeable housings. In some embodiments, a nitric oxide permeable housing 104 may include one or more ports that facilitate release of nitric oxide from the one or more nitric oxide permeable housings 104. Ports may be configured in numerous ways. For example, in some embodiments, one or more housings may be configured as a tube, a cylinder, a square box, a rectangular box, a disc, a triangle, a ball, and the like. A nitric oxide permeable housing 104 may include one or more ports that may have numerous configurations. In some embodiments, a port may be a simple passage (e.g., hole, slit, crack, etc.) through a nitric oxide permeable housing 104. For example, in some embodiments, a nitric oxide permeable housing 104 may be configured as a tube having a first closed end and a second end that includes a simple passage. In some embodiments, a nitric oxide permeable housing 104 may include a threaded port into which a plug may be screwed and/or unscrewed to open or close the port. In some embodiments, a nitric oxide permeable housing 104 may include a tube within a tube construction that includes a first perforated tube and a second perforated tube. Accordingly, the first tube may be rotated within the second tube such that one or more perforations in the first tube align with one or more perforations in the second tube to create a port through which nitric oxide may pass. In some embodiments, such tube within a tube configurations may be operably connected to an apparatus (e.g., electric motor) that is configured to rotate the first tube and/or the second tube to control opening and closing of one or more ports. In some embodiments, a nitric oxide permeable housing 104 may include one or more ports that are controlled with one or more electrical solenoids. In some embodiments, a nitric oxide permeable housing 104 may include one or more ports that are controlled with one or more electromagnets. Accordingly, in some embodiments, one or more ports may be opened or closed through regulation of current passing through one or more electromagnets associated with the ports.

At embodiment 304, module 210 may include one or more control units that control one or more ports that facilitate release of nitric oxide from the one or more nitric oxide permeable housings. In some embodiments, a nitric oxide permeable housing 104 may include one or more control units 126 that control one or more ports that facilitate release of nitric oxide from the one or more nitric oxide permeable housings 104. In some embodiments, one or more control units 126 may be responsive to one or more timers. For example, in some embodiments, one or more control units 126 may open one or more ports at one or more times (e.g., 9:00 AM, 9:00 PM, 12:00 AM) provided by a timer. In some embodiments, one or more control units 126 may close one or more ports at one or more times (e.g., 9:00 AM, 9:00 PM, 12:00 AM) provided by a timer. In some embodiments, one or more control units 126 may be responsive to one or more signals 116. In some embodiments, one or more control units 126 may respond to one or more signals 116 by opening one or more ports. In some embodiments, one or more control units 126 may respond to one or more signals 116 by closing one or more ports. Accordingly, in some embodiments, one or more control units 126 may include one or more receivers. A control unit 126 may include numerous types of receivers. Examples of such receivers include, but are not limited to, receivers that receive one or more optical signals 116, radio signals 116, wireless signals 116, hardwired signals 116, infrared signals 116, ultrasonic signals 116, and the like. Such receivers are known and have been described (e.g., U.S. Pat. Nos. RE 39,785; 7,218,900; 7,254,160; 7,245,894; 7,206,605; herein incorporated by reference). In some embodiments, one or more control units 126 may be responsive to one or more programs. In some embodiments, one or more control units 126 may open and/or close one or more ports in accordance with a time schedule provided by one or more programs. For example, in some embodiments, one or more control units 126 may open one or more ports at a selected time for a period of time and then close the one or more ports. In some embodiments, one or more control units 126 may open one or more ports at a selected time and then close one or more ports at a selected time in response to one or more programs. In some embodiments, one or more control units 126 may open and/or close one or more ports in response to instructions received from one or more programs. For example, in some embodiments, one or more programs may receive information associated with one or more sensors and then instruct one or more control units 126 to open and/or close one or more ports. Accordingly, in some embodiments, one or more programs may be used to control the opening and/or closing of one or more ports.

A control unit 126 may control the operation of one or more ports through numerous mechanisms. For example, in some embodiments, a control unit 126 may be operably coupled to an electric motor that serves to open and/or close one or more ports through rotation of a screw mechanism. Accordingly, in some embodiments, a control unit 126 may control operation of one or more electric motors to facilitate opening and/or closing of a port. In some embodiments, a control unit 126 may be operably coupled to an electromagnet that facilitates opening and/or closing of a port (e.g., fuel injectors, fluid valves, and the like). Accordingly, a control unit 126 may be configured in numerous ways.

At embodiment 306, module 210 may include one or more electrical connectors that are configured for connection to one or more light sources. In some embodiments, a nitric oxide permeable housing 104 may include one or more electrical connectors that are configured for connection to one or more light sources 108. Numerous configurations of electrical connectors may be used in association with a nitric oxide permeable housing 104. For example, in some embodiments, a nitric oxide permeable housing 104 may include a circuit board to which one or more light sources 108 may be attached. In some embodiments, a nitric oxide permeable housing 104 may include one or more terminals (e.g., crimp-on terminals) to which one or more light sources 108 may be attached. In some embodiments, a nitric oxide permeable housing 104 may include one or more plug and socket connectors. In some embodiments, a nitric oxide permeable housing 104 may include one or more universal serial bus connectors. Accordingly, numerous types of connectors may be associated with a nitric oxide permeable housing 104.

At embodiment 308, module 210 may include one or more nitric oxide permeable membranes. In some embodiments, a nitric oxide permeable housing 104 may include one or more nitric oxide permeable membranes. A nitric oxide permeable housing 104 may include one or more nitric oxide permeable layers that are fabricated from numerous types of material. Examples of such materials include, but are not limited to, ceramics, polymeric materials, metals, plastics, and the like. In some embodiments, one or more nitric oxide permeable layers may include numerous combinations of materials. For example, in some embodiments, a nitric oxide permeable layer may include a nitric oxide impermeable material that is coupled to a nitric oxide permeable material. In some embodiments, a nitric oxide permeable layer may include one or more nitric oxide permeable membranes (e.g., U.S. Patent Application No. 20020026937). In some embodiments, a nitric oxide permeable layer may include a selectively permeable membrane. For example, in some embodiments, a nitric oxide permeable layer may include a selectively permeable membrane that is a hydrophilic polyester co-polymer membrane system that includes a copolymer with 70% polyester and 30% polyether (e.g., Sympatex™ 10 μm membrane, see Hardwick et al., Clinical Science, 100:395-400 (2001)). In some embodiments, a nitric oxide permeable layer may include a nitric oxide permeable coating (e.g., U.S. Patent Application Nos. 20050220838 and 20030093143).

In some embodiments, one or more nitric oxide permeable layers may form the exterior surface of a nitric oxide permeable housing 104. In some embodiments, one or more nitric oxide permeable layers may be included in one or more portions of a nitric oxide permeable housing 104.

In some embodiments, one or more nitric oxide permeable layers may be configured to enclose at least a portion of one or more photolyzable nitric oxide donors 106. In some embodiments, one or more nitric oxide permeable layers may be configured to enclose at least a portion of one or more light sources 108, at least a portion of one or more sensors 118, at least a portion of one or more electromagnetic receivers 110, or substantially any combination thereof.

At embodiment 310, module 210 may include one or more windows that allow light to pass. In some embodiments, a nitric oxide permeable housing 104 may include one or more windows that allow light to pass. Numerous materials may be used to fabricate one or more windows that allow light to pass. Examples of such materials include, but are not limited to, glass, plastic, polymeric materials, fiber optic cables, and the like. In some embodiments, one or more windows may alter light that passes through the one or more windows. For example, in some embodiments, a window may include one or more quantum dots that absorb light and then transmit light of different wavelengths. In some embodiments, a window may include one or more materials that upconvert light. For example, in some embodiments, a window may include one or more rare-earth materials. In some embodiments, one or more windows may be configured to allow passage of light of certain wavelengths. In some embodiments, one or more windows may be configured to disallow passage of light of certain wavelengths. In some embodiments, one or more windows may be configured to allow passage of light of certain wavelengths and to disallow passage of light of certain wavelengths. For example, in some embodiments, a window may be configured to allow passage of visible light but to disallow passage of ultraviolet light. In some embodiments, one or more windows may be configured such that their light transmission characteristics may be regulated through application of electrical current to the one or more windows.

In some embodiments, a nitric oxide permeable housing 104 may include two or more compartments that are separated by a window through which light may pass. Accordingly, in some embodiments, a nitric oxide permeable housing 104 may include a first compartment that includes one or more light sources 108 and a second compartment that includes one or more photolyzable nitric oxide donors 106 that are separated by a window. Accordingly, passage of light emitted by the one or more light sources 108 through the window may facilitate release of nitric oxide from the one or more photolyzable nitric oxide donors 106. Accordingly, a window may be configured in numerous ways.

At embodiment 312, module 210 may include one or more quartz windows. In some embodiments, a nitric oxide permeable housing 104 may include one or more quartz windows. In some embodiments, one or more nitric oxide permeable housings 104 may be configured to allow passage of ultraviolet light through one or more windows.

In some embodiments, one or more quartz windows may alter light that passes through the one or more windows. For example, in some embodiments, a quartz window may include one or more quantum dots that absorb light and then transmit light of different wavelengths. In some embodiments, a quartz window may include one or more materials that upconvert light. For example, in some embodiments, a quartz window may include one or more rare-earth materials. In some embodiments, one or more quartz windows may be configured to allow passage of light of certain wavelengths. In some embodiments, one or more quartz windows may be configured to disallow passage of light of certain wavelengths. In some embodiments, one or more quartz windows may be configured to allow passage of light of certain wavelengths and to disallow passage of light of certain wavelengths.

In some embodiments, a nitric oxide permeable housing 104 may include two or more compartments that are separated by a quartz window through which light may pass. Accordingly, in some embodiments, a nitric oxide permeable housing 104 may include a first compartment that includes one or more light sources 108 and a second compartment that includes one or more photolyzable nitric oxide donors 106 that are separated by a quartz window. Accordingly, passage of light emitted by the one or more light sources 108 through the quartz window may facilitate release of nitric oxide from the one or more photolyzable nitric oxide donors 106. Accordingly, a quartz window may be configured in numerous ways.

Figure 4:
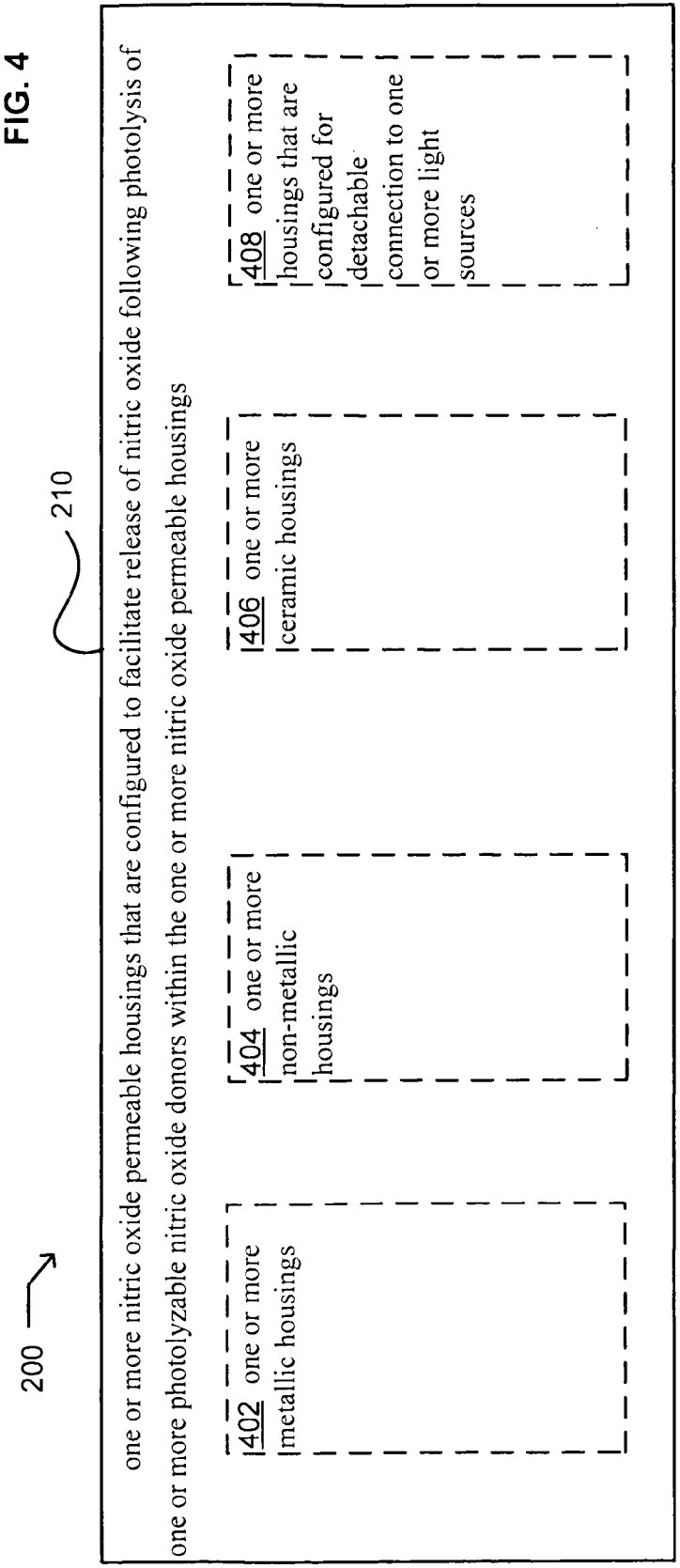
FIG. 4 illustrates alternate embodiments of module 210 of embodiment 200 of apparatus 102 within system 100.

FIG. 4 illustrates alternative embodiments of embodiment 200 of an apparatus 102 within system 100 of FIG. 2. FIG. 4 illustrates example embodiments of module 210 of an apparatus 102. Additional embodiments may include an embodiment 402, an embodiment 404, an embodiment 406, and/or an embodiment 408.

At embodiment 402, module 210 may include one or more metallic housings. In some embodiments, a nitric oxide permeable housing 104 may include one or more metallic housings. In some embodiments, a nitric oxide permeable housing 104 may include one or more housings that are entirely metallic. In some embodiments, a nitric oxide permeable housing 104 may include one or more housings that include one or more portions that are metallic. In some embodiments, a nitric oxide permeable housing 104 may include one or more housings that include one or more portions that are metallic and one or more portions that are non-metallic. Numerous metallic materials may be included within a nitric oxide permeable housing 104. Examples of such materials include, but are not limited to, stainless steel, titanium, copper, brass, aluminum, metallic alloys, and the like. In some embodiments, numerous types of metallic materials may be included within the same nitric oxide permeable housing 104. For example, in some embodiments, a nitric oxide permeable housing 104 may be configured as a stainless steel tube with a first closed end, a second end that includes a port, and copper connections configured for association with one or more light sources 108. Accordingly, numerous types of materials may be included within a nitric oxide permeable housing 104.

At embodiment 404, module 210 may include one or more non-metallic housings. In some embodiments, a nitric oxide permeable housing 104 may include one or more non-metallic housings. In some embodiments, a nitric oxide permeable housing 104 may include one or more housings that are entirely non-metallic. In some embodiments, a nitric oxide permeable housing 104 may include one or more housings that include one or more portions that are non-metallic. In some embodiments, a nitric oxide permeable housing 104 may include one or more housings that include one or more portions that are non-metallic and one or more portions that are metallic. Numerous non-metallic materials may be included within a nitric oxide permeable housing 104. Examples of such materials include, but are not limited to, ceramics, glass, plastic, polymeric materials, and the like. In some embodiments, numerous types of non-metallic materials may be included within the same nitric oxide permeable housing 104. For example, in some embodiments, a nitric oxide permeable housing 104 may be configured as a plastic tube having a first closed end, and a second open end that is associated with one or more nitric oxide permeable membranes. Accordingly, numerous types of materials may be included within a nitric oxide permeable housing 104.

At embodiment 406, module 210 may include one or more ceramic housings. In some embodiments, a nitric oxide permeable housing 104 may include one or more ceramic housings. In some embodiments, a nitric oxide permeable housing 104 may include one or more housings that are entirely ceramic. In some embodiments, a nitric oxide permeable housing 104 may include one or more housings that include one or more portions that are ceramic. In some embodiments, a nitric oxide permeable housing 104 may include one or more housings that include one or more portions that are ceramic and one or more portions that are non-ceramic. Numerous ceramic materials may be included within a nitric oxide permeable housing 104. Examples of such materials include, but are not limited to, cermets, clays, glasses, sintered glass, electrically conductive ceramics, semiconductive ceramics, piezoelectric ceramics, and the like. In some embodiments, numerous types of non-ceramic materials may be included within the same nitric oxide permeable housing 104. For example, in some embodiments, a nitric oxide permeable housing 104 may be configured as a ceramic tube having a first closed end, and a second open end that is associated with one or more nitric oxide permeable membranes. Accordingly, numerous types of materials may be included within a nitric oxide permeable housing 104.

At embodiment 408, module 210 may include one or more housings that are configured for detachable connection to one or more light sources. In some embodiments, a nitric oxide permeable housing 104 may include one or more housings that are configured for detachable connection to one or more light sources 108. For example, in some embodiments, a nitric oxide permeable housing 104 may include a cavity into which a light source 108 may be inserted. Accordingly, in some embodiments, a first light source 108 may be associated with a nitric oxide permeable housing 104 and then replaced with a second light source 108 that may be associated with the nitric oxide permeable housing 104. In some embodiments, a nitric oxide permeable housing 104 may be configured as a disposable unit that includes one or more photolyzable nitric oxide donors 106. Accordingly, such a nitric oxide permeable housing 104 may be associated with a light source 108 and then replaced with a second nitric oxide permeable housing 104.

Figure 5:
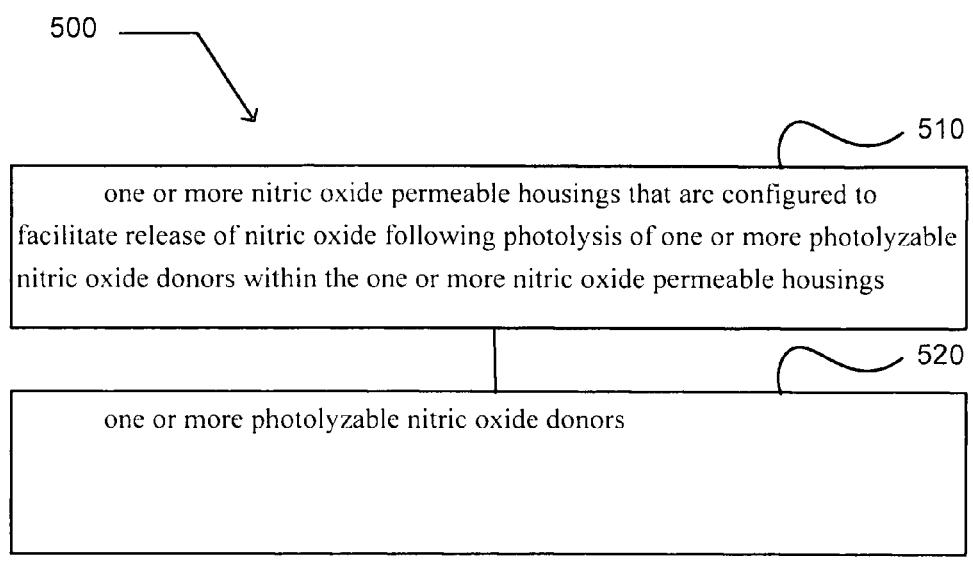
FIG. 5 illustrates embodiment 500 of apparatus 102 within system 100.

FIG. 5 illustrates embodiment 500 of an apparatus 102 within system 100. In FIG. 5, discussion and explanation may be provided with respect to the above-described example of FIG. 1, and/or with respect to other examples and contexts. In some embodiments, module 210 of FIG. 2 may correspond to module 510 as described with respect to embodiment 500 of an apparatus 102 within system 100. However, it should be understood that the modules may execute operations in a number of other environments and contexts, and/or modified versions of FIG. 1. Also, although the various modules are presented in the sequence(s) illustrated, it should be understood that the various modules may be configured in numerous orientations.

The embodiment 500 may include module 510 that includes one or more nitric oxide permeable housings that are configured to facilitate release of nitric oxide following photolysis of one or more photolyzable nitric oxide donors within the one or more nitric oxide permeable housings. In some embodiments, an apparatus 102 may include one or more nitric oxide permeable housings 104 that are configured to facilitate release of nitric oxide following photolysis of one or more photolyzable nitric oxide donors 106 within the one or more nitric oxide permeable housings. In some embodiments, a nitric oxide permeable housing 104 may include one or more light sources 108. In some embodiments, a nitric oxide permeable housing 104 may include one or more light sources 108 that are configured to emit light that facilitates release of nitric oxide from one or more photolyzable nitric oxide donors 106. In some embodiments, a nitric oxide permeable housing 104 may include one or more photolyzable nitric oxide donors 106. In some embodiments, a nitric oxide permeable housing 104 may be configured for implantation within a user 124. For example, in some embodiments, a nitric oxide permeable housing 104 may be configured to facilitate delivery of nitric oxide to the genital region of a user 124. In some embodiments, a nitric oxide permeable housing 104 may be configured to facilitate delivery of nitric oxide to the vasculature of a user 124. In some embodiments, a nitric oxide permeable housing 104 may be configured to facilitate delivery of nitric oxide to a surface. In some embodiments, a nitric oxide permeable housing 104 may be configured to be included within a bandage, a patch, tape, clothing, and the like. In some embodiments, a nitric oxide permeable housing 104 may include one or more nitric oxide permeable layers. In some embodiments, a nitric oxide permeable housing 104 may include one or more valves that are configured to provide for passage of nitric oxide from the nitric oxide permeable housing 104. In some embodiments, a nitric oxide permeable housing 104 may include one or more controllable valves that are configured to provide for passage of nitric oxide from the nitric oxide permeable housing 104. Accordingly, in some embodiments, a nitric oxide permeable housing 104 may include one or more control units 126. In some embodiments, one or more control units 126 may be configured to control one or more valves. In some embodiments, one or more control units 126 may be configured to control one or more light sources 108.

The embodiment 500 may include module 520 that includes one or more photolyzable nitric oxide donors. In some embodiments, an apparatus 102 may include one or more photolyzable nitric oxide donors 106. In some embodiments, an apparatus 102 may include one or more photolyzable nitric oxide donors 106 that release nitric oxide upon photolysis. Examples of such photolyzable nitric oxide donors 106 include, but are not limited to, diazeniumdiolates (e.g., U.S. Pat. Nos. 7,105,502; 7,122,529; 6,673,338; herein incorporated by reference), trans-[RuCl([15]aneN4)NO]+2 (Ferezin et al., Nitric Oxide, 13:170-175 (2005), Bonaventura et al., Nitric Oxide, 10:83-91 (2004)), nitrosyl ligands (e.g., U.S. Pat. No. 5,665,077; herein incorporated by reference, Chmura et al., Nitric Oxide, 15:370-379 (2005), Flitney et al., Br. J. Pharmacol., 107:842-848 (1992), Flitney et al., Br. J. Pharmacol., 117:1549-1557 (1996), Matthews et al., Br. J. Pharmacol., 113:87-94 (1994)), 6-Nitrobenzo[α]pyrene (e.g., Fukuhara et al., J. Am. Chem. Soc., 123:8662-8666 (2001)), S-nitroso-glutathione (e.g., Rotta et al., Braz. J. Med. Res., 36:587-594 (2003), Flitney and Megson, J. Physiol., 550:819-828 (2003)), S-nitrosothiols (e.g., Andrews et al., British Journal of Pharmacology, 138:932-940 (2003), Singh et al., FEBS Lett., 360:47-51 (1995)), 2-Methyl-2-nitrosopropane (e.g., Pou et al., Mol. Pharm., 46:709-715 (1994), Wang et al., Chem. Rev., 102:1091-1134 (2002)), imidazolyl derivatives (e.g., U.S. Pat. No. 5,374,710; herein incorporated by reference).

Figure 6:
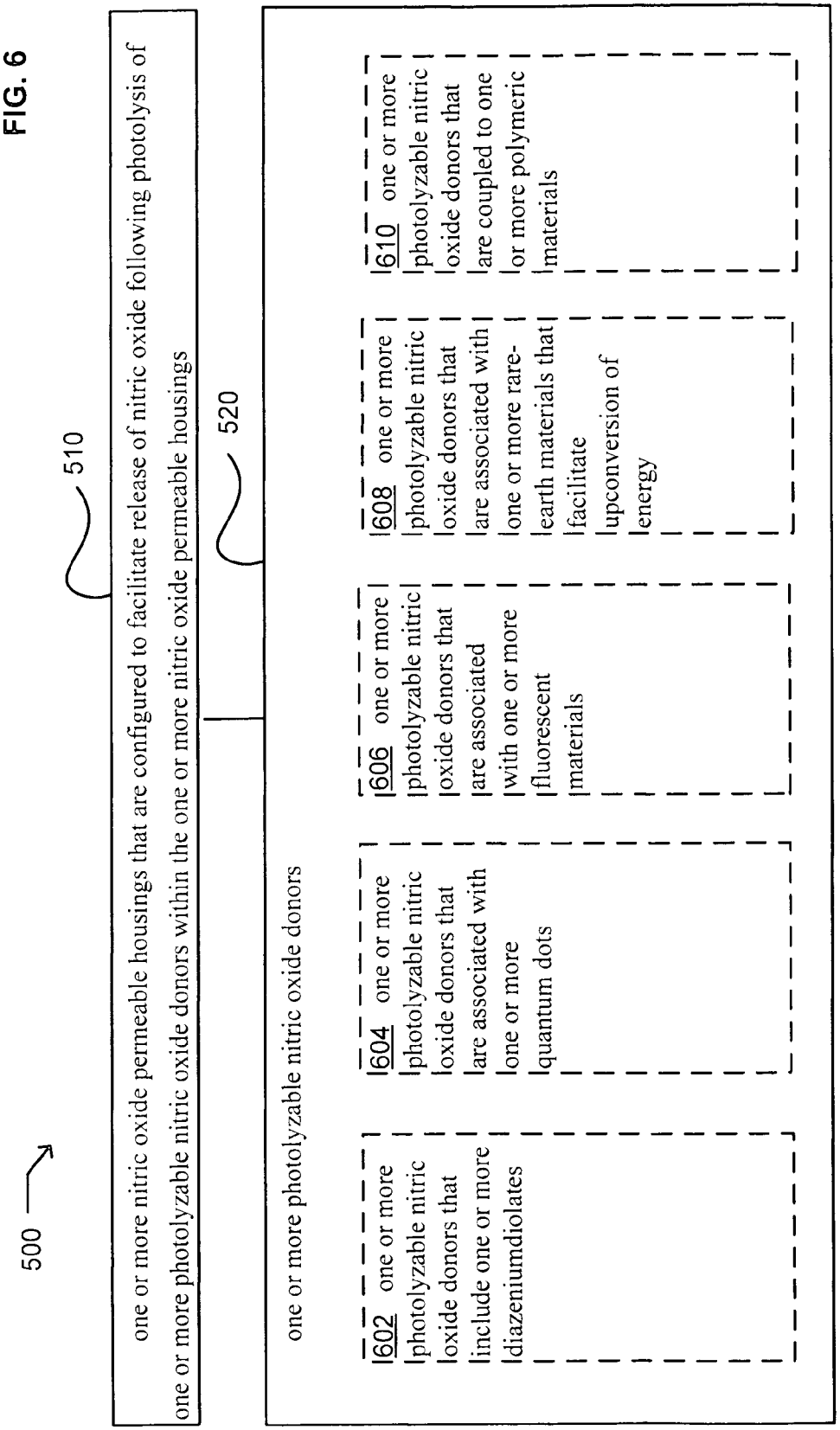
FIG. 6 illustrates alternate embodiments of module 520 of embodiment 500 of apparatus 102 within system 100.

FIG. 6 illustrates alternative embodiments of embodiment 500 of an apparatus 102 within system 100 of FIG. 5. FIG. 6 illustrates example embodiments of module 520 of an apparatus 102. Additional embodiments may include an embodiment 602, an embodiment 604, an embodiment 606, an embodiment 608, and/or an embodiment 610.

At embodiment 602, module 520 may include one or more photolyzable nitric oxide donors that include one or more diazeniumdiolates. In some embodiments, one or more photolyzable nitric oxide donors 106 may include one or more photolyzable nitric oxide donors 106 that include one or more diazeniumdiolates. Many photolyzable nitric oxide donors 106 that are diazeniumdiolates are known and have been described (e.g., U.S. Pat. No. 7,122,529). Examples of such diazeniumdiolates include, but are not limited to $O^2$-benzyl, $O^2$-naphthylmethyl substituted diazeniumdiolates and $O^2$-naphthylallyl substituted diazeniumdiolates.

At embodiment 604, module 520 may include one or more photolyzable nitric oxide donors that are associated with one or more quantum dots. In some embodiments, one or more photolyzable nitric oxide donors 106 may include one or more photolyzable nitric oxide donors 106 that are associated with one or more quantum dots. In some embodiments, one or more quantum dots may be tuned to emit light that facilitates photolysis of one or more nitric oxide donors. In some embodiments, a quantum dot may be tuned to emit light that specifically facilitates photolysis of one or more nitric oxide donors. For example, in some embodiments, one or more quantum dots may emit select wavelengths of light that correspond to wavelengths of light that cause photolysis of one or more nitric oxide donors. In some embodiments, one or more quantum dots may be selected that absorb light emitted by one or more light sources 108 and emit light that facilitates photolysis of one or more nitric oxide donors.

At embodiment 606, module 520 may include one or more photolyzable nitric oxide donors that are associated with one or more fluorescent materials. In some embodiments, one or more photolyzable nitric oxide donors 106 may include one or more photolyzable nitric oxide donors 106 that are associated with one or more fluorescent materials. Numerous fluorescent materials may be associated with one or more photolyzable nitric oxide donors 106. Examples of such materials include, but are not limited to, 1,4-diphenylbutadiene; 9,10-diphenylanthracene; benzene; biphenyl; ethyl-p-dimethylaminobenzoate; naphthalene; P-terphenyl; ethyl-p-dimethylaminobenzoate; stilbene; tryptophan; tyrosine; 1,2-diphenylacetylene; 7-methoxycoumarin-4-acetic acid; anthracene; indo-1; POPOP; P-quaterphenyl; pyrene; and the like.

At embodiment 608, module 520 may include one or more photolyzable nitric oxide donors that are associated with one or more rare-earth materials that facilitate upconversion of energy. In some embodiments, one or more photolyzable nitric oxide donors 106 may include one or more photolyzable nitric oxide donors 106 that are associated with one or more rare-earth materials that facilitate upconversion of energy. In some embodiments, infrared light may be upconverted to visible light (e.g., Mendioroz et al., Optical Materials, 26:351-357 (2004). In some embodiments, infrared light may be upconverted to ultraviolet light (e.g., Mendioroz et al., Optical Materials, 26:351-357 (2004). In some embodiments, one or more photolyzable nitric oxide donors 106 may be associated with one or more rare-earth materials (e.g., ytterbium-erbium, ytterbium-thulium, or the like) that facilitate upconversion of energy (e.g., U.S. Pat. No. 7,088,040; herein incorporated by reference). For example, in some embodiments, one or more photolyzable nitric oxide donors 106 may be associated with $Nd^{3+}$ doped $KPb_2Cl_5$ crystals. In some embodiments, one or more photolyzable nitric oxide donors 106 may be associated with thiogallates doped with rare earths, such as $CaGa_2S_4:Ce^{3+}$ and $SrGa_2S_4:Ce^{3+}$. In some embodiments, one or more photolyzable nitric oxide donors 106 may be associated with aluminates that are doped with rare earths, such as $YAlO_3:Ce^{3+}$, $YGaO_3:Ce^{3+}$, $Y(Al,Ga)O_3:Ce^{3+}$, and orthosilicates $M_2SiO_5:Ce^{3+}$ (M:Sc, Y, Sc) doped with rare earths, such as, for example, $Y_2SiO_5:Ce^{3+}$. In some embodiments, yttrium may be replaced by scandium or lanthanum (e.g., U.S. Pat. Nos. 6,812,500 and 6,327,074; herein incorporated by reference). Numerous materials that may be used to upconvert energy have been described (e.g., U.S. Pat. Nos. 5,956,172; 5,943,160; 7,235,189; 7,215,687; herein incorporated by reference).

At embodiment 610, module 520 may include one or more photolyzable nitric oxide donors that are coupled to one or more polymeric materials. In some embodiments, one or more photolyzable nitric oxide donors 106 may include one or more photolyzable nitric oxide donors 106 that are coupled to one or more polymeric materials. For example, in some embodiments, one or more polymer matrices may be impregnated with one or more photolyzable nitric oxide donors 106 (e.g., U.S. Pat. No. 5,994,444). In some embodiments, one or more photolyzable nitric oxide donors 106 may be bound to a polymer. Methods that can be used to couple nitric oxide donors to a polymeric matrix have been reported (e.g., U.S. Pat. No. 5,405,919). In some embodiments, one or more polymers to which one or more photolyzable nitric oxide donors 106 are coupled may be used to construct one or more housings.

Figure 7:
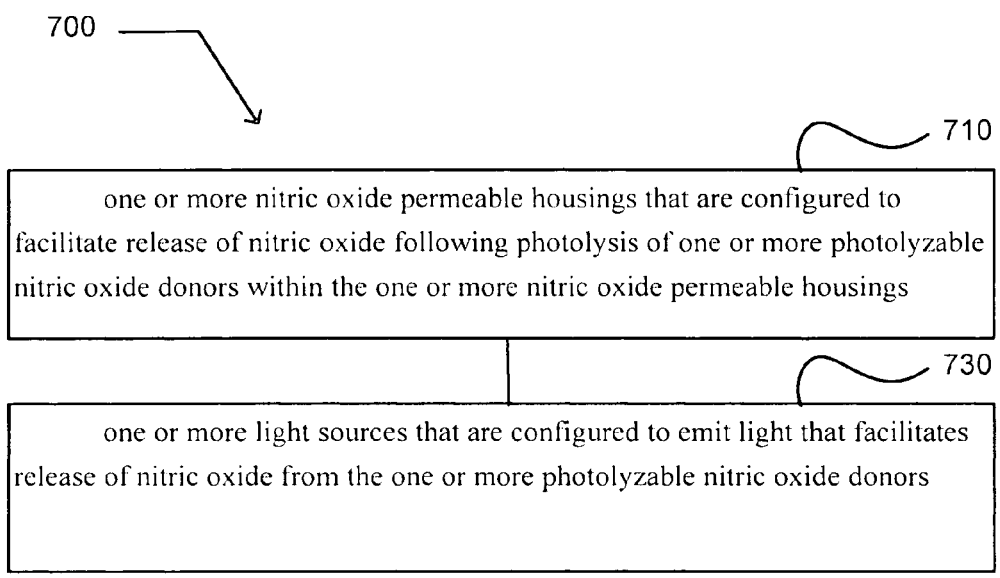
FIG. 7 illustrates embodiment 700 of apparatus 102 within system 100.

FIG. 7 illustrates embodiment 700 of an apparatus 102 within system 100. In FIG. 7, discussion and explanation may be provided with respect to the above-described example of FIG. 1, and/or with respect to other examples and contexts. In some embodiments, module 210 of FIG. 2 may correspond to module 710 as described with respect to embodiment 700 of an apparatus 102 within system 100. However, it should be understood that the modules may execute operations in a number of other environments and contexts, and/or modified versions of FIG. 1. Also, although the various modules are presented in the sequence(s) illustrated, it should be understood that the various modules may be configured in numerous orientations.

The embodiment 700 may include module 710 that includes one or more nitric oxide permeable housings that are configured to facilitate release of nitric oxide following photolysis of one or more photolyzable nitric oxide donors within the one or more nitric oxide permeable housings. In some embodiments, an apparatus 102 may include one or more nitric oxide permeable housings 104 that are configured to facilitate release of nitric oxide following photolysis of one or more photolyzable nitric oxide donors 106 within the one or more nitric oxide permeable housings. In some embodiments, a nitric oxide permeable housing 104 may include one or more light sources 108. In some embodiments, a nitric oxide permeable housing 104 may include one or more light sources 108 that are configured to emit light that facilitates release of nitric oxide from one or more photolyzable nitric oxide donors 106. In some embodiments, a nitric oxide permeable housing 104 may include one or more photolyzable nitric oxide donors 106. In some embodiments, a nitric oxide permeable housing 104 may be configured for implantation within a user 124. For example, in some embodiments, a nitric oxide permeable housing 104 may be configured to facilitate delivery of nitric oxide to the genital region of a user 124. In some embodiments, a nitric oxide permeable housing 104 may be configured to facilitate delivery of nitric oxide to the vasculature of a user 124. In some embodiments, a nitric oxide permeable housing 104 may be configured to facilitate delivery of nitric oxide to a surface. In some embodiments, a nitric oxide permeable housing 104 may be configured to be included within a bandage, a patch, tape, clothing, and the like. In some embodiments, a nitric oxide permeable housing 104 may include one or more nitric oxide permeable layers. In some embodiments, a nitric oxide permeable housing 104 may include one or more valves that are configured to provide for passage of nitric oxide from the nitric oxide permeable housing 104. In some embodiments, a nitric oxide permeable housing 104 may include one or more controllable valves that are configured to provide for passage of nitric oxide from the nitric oxide permeable housing 104. Accordingly, in some embodiments, a nitric oxide permeable housing 104 may include one or more control units 126. In some embodiments, one or more control units 126 may be configured to control one or more valves. In some embodiments, one or more control units 126 may be configured to control one or more light sources 108.

The embodiment 700 may include module 730 that includes one or more light sources that are configured to emit light that facilitates release of nitric oxide from the one or more photolyzable nitric oxide donors. In some embodiments, an apparatus 102 may include one or more light sources 108 that are configured to emit light that facilitates release of nitric oxide from the one or more photolyzable nitric oxide donors 106. A light source 108 may be configured in numerous ways. For example, in some embodiments, a light source 108 may include a chemiluminescent light source 108. In some embodiments, a light source 108 may include a phosphorescent light source 108. In some embodiments, a light source 108 may include a light emitter that is coupled to a power supply. For example, in some embodiments, a light source 108 may include one or more light emitting diodes that are coupled to one or more power supplies. Examples of power supplies include, but are not limited to, capacitors, batteries, electromagnetic receivers 110, and the like. In some embodiments, one or more light sources 108 may be configured to emit light that specifically facilitates release of nitric oxide from one or more photolyzable nitric oxide donors 106. For example, in some embodiments, one or more light sources 108 may be configured to emit one or more wavelengths of light that facilitate photodecomposition of one or more photolyzable nitric oxide donors 106. In some embodiments, one or more light sources 108 may be configured such they do not emit one or more wavelengths of light that do not facilitate photodecomposition of one or more photolyzable nitric oxide donors 106. Accordingly, in some embodiments, one or more light sources 108 may be configured to emit light that is matched to one or more photolyzable nitric oxide donors 106 and causes photodecomposition of the one or more photolyzable nitric oxide donors 106. In some embodiments, one or more light sources 108 may be configured such that they do not emit light that cross-links biological structures (e.g., proteins) or that causes the formation of DNA adducts. Accordingly, in some embodiments, one or more light sources 108 may be configured to emit light that photolyzes one or more photolyzable nitric oxide donors 106 with reduced damage to surrounding tissue. For example, in some embodiments, one or more light sources 108 may be configured to emit visible light ($\lambda=550$ nm) to facilitate homolytic decomposition of S-nitrosoglutathione to generate nitric oxide (e.g., Singh et al., FEBS Letters, 360:47-51 (1995)). In some embodiments, ultraviolet light may be used to facilitate release of nitric oxide from one or more photolyzable nitric oxide donors 106. For example, in some embodiments, one or more light sources 108 may be configured to emit ultraviolet light ($\lambda=355$ nm) to release nitric oxide from S-nitrosothiols (e.g., Rotta et al., Braz. J. Med. Biol. Res., 36:587-594 (2003)). In some embodiments, one or more light sources 108 may be configured to emit light over a broad range of wavelengths that will facilitate release of nitric oxide from one or more photolyzable nitric oxide donors 106. For example, in some embodiments, $O^2$-benzyl substituted diazeniumdiolates, $O^2$-napthylmethyl substituted diazeniumdiolates, and/or $O^2$-napththylallyl substituted diazeniumdiolates may be photolyzed by light over a broad range of wavelengths ($\lambda=254$ nm to $\lambda=700$ nm) (e.g., U.S. Pat. No. 7,122,529).

Figure 8:
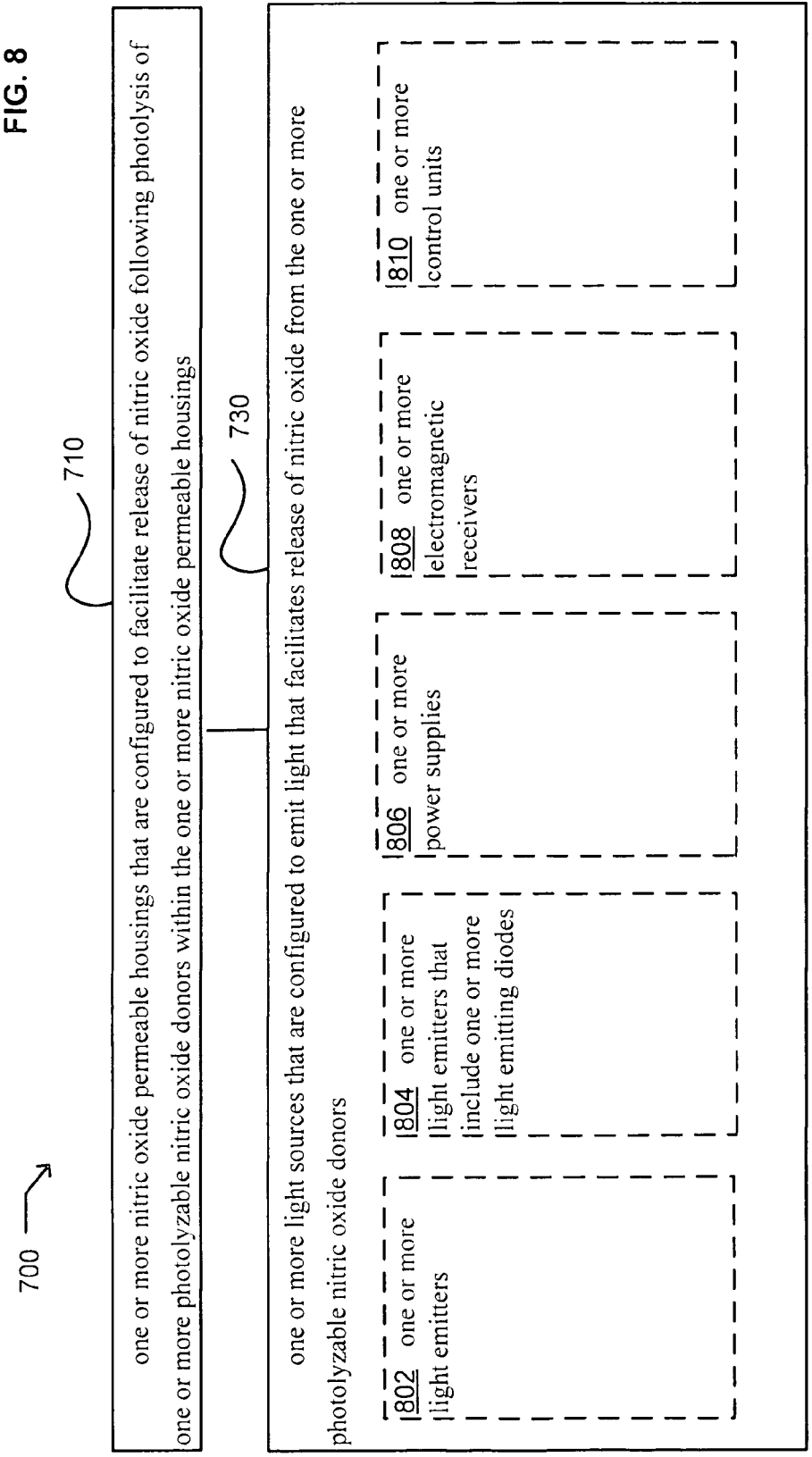
FIG. 8 illustrates alternate embodiments of module 730 of embodiment 700 of apparatus 102 within system 100.

FIG. 8 illustrates alternative embodiments of embodiment 700 of an apparatus 102 within system 100 of FIG. 7. FIG. 8 illustrates example embodiments of module 730 of an apparatus 102. Additional embodiments may include an embodiment 802, an embodiment 804, an embodiment 806, an embodiment 808, and/or an embodiment 810.

At embodiment 802, module 730 may include one or more light emitters. In some embodiments, one or more light sources 108 may include one or more light emitters. Numerous types of light emitters may be associated with one or more light sources 108. Examples of such light emitters include, but are not limited to, light emitting diodes, filaments, arc lamps, fluorescent light emitters, phosphorescent light emitters, chemiluminescent emitters, and the like. In some embodiments, one or more light emitters may be coupled with one or more quantum dots. In some embodiments, one or more light emitters may be coupled with one or more rare-earth materials.

At embodiment 804, module 730 may include one or more light emitters that include one or more light emitting diodes. In some embodiments, one or more light sources 108 may include one or more light emitting diodes. One or more light sources 108 may include one or more light emitting diodes that are configured to emit light of select wavelengths. For example, light emitting diodes may be configured to emit infrared light, visible light, near-ultraviolet light, or ultraviolet light. In some embodiments, a light source 108 may include a conventional light emitting diode that can include a variety of inorganic semiconductor materials. Examples of such materials and the emitting light include, but are not limited to, aluminium gallium arsenide (red and infrared), aluminium gallium phosphide (green), aluminium gallium indium phosphide (high-brightness orange-red, orange, yellow, and green), gallium arsenide phosphide (red, orange-red, orange, and yellow), gallium phosphide (red, yellow and green), gallium nitride (green, pure green, emerald green, blue, and white (if it has an AlGaN Quantum Barrier)), indium gallium nitride (near ultraviolet, bluish-green and blue), silicon carbide (blue), silicon (blue), sapphire (blue), zinc selenide (blue), diamond (ultraviolet), aluminium nitride (near to far ultraviolet), aluminium gallium nitride (near to far ultraviolet), aluminium gallium indium nitride (near to far ultraviolet).

At embodiment 806, module 730 may include one or more power supplies. In some embodiments, one or more light sources 108 may include one or more power supplies. Numerous types of power supplies may be associated with one or more light sources 108. Examples of such power supplies include, but are not limited to, batteries (e.g., thin film batteries), electromagnetic receivers 110, line power, and the like.

At embodiment 808, module 730 may include one or more electromagnetic receivers. In some embodiments, one or more light sources 108 may include one or more electromagnetic receivers 110. In some embodiments, one or more electromagnetic receivers 110 may be used to receive electromagnetic energy 112 for use in providing power to one or more light emitters. Methods to construct electromagnetic receivers 110 have been described (e.g., U.S. Pat. No. 5,571,152).

At embodiment 810, module 730 may include one or more control units. In some embodiments, one or more light sources 108 may include one or more control units 126. In some embodiments, the one or more control units 126 may be operably associated with one or more light sources 108 through use of a hardwired connection. In some embodiments, the one or more control units 126 may be operably associated with one or more light sources 108 through use of a wireless connection. In some embodiments, one or more control units 126 may include numerous types of receivers. Examples of such receivers include, but are not limited to, receivers that receive one or more optical signals 116, radio signals 116, wireless signals 116, hardwired signals 116, infrared signals 116, ultrasonic signals 116, and the like. Such receivers are known and have been described (e.g., U.S. Pat. Nos. RE 39,785; 7,218,900; 7,254,160; 7,245,894; 7,206,605; herein incorporated by reference).

Figure 9:
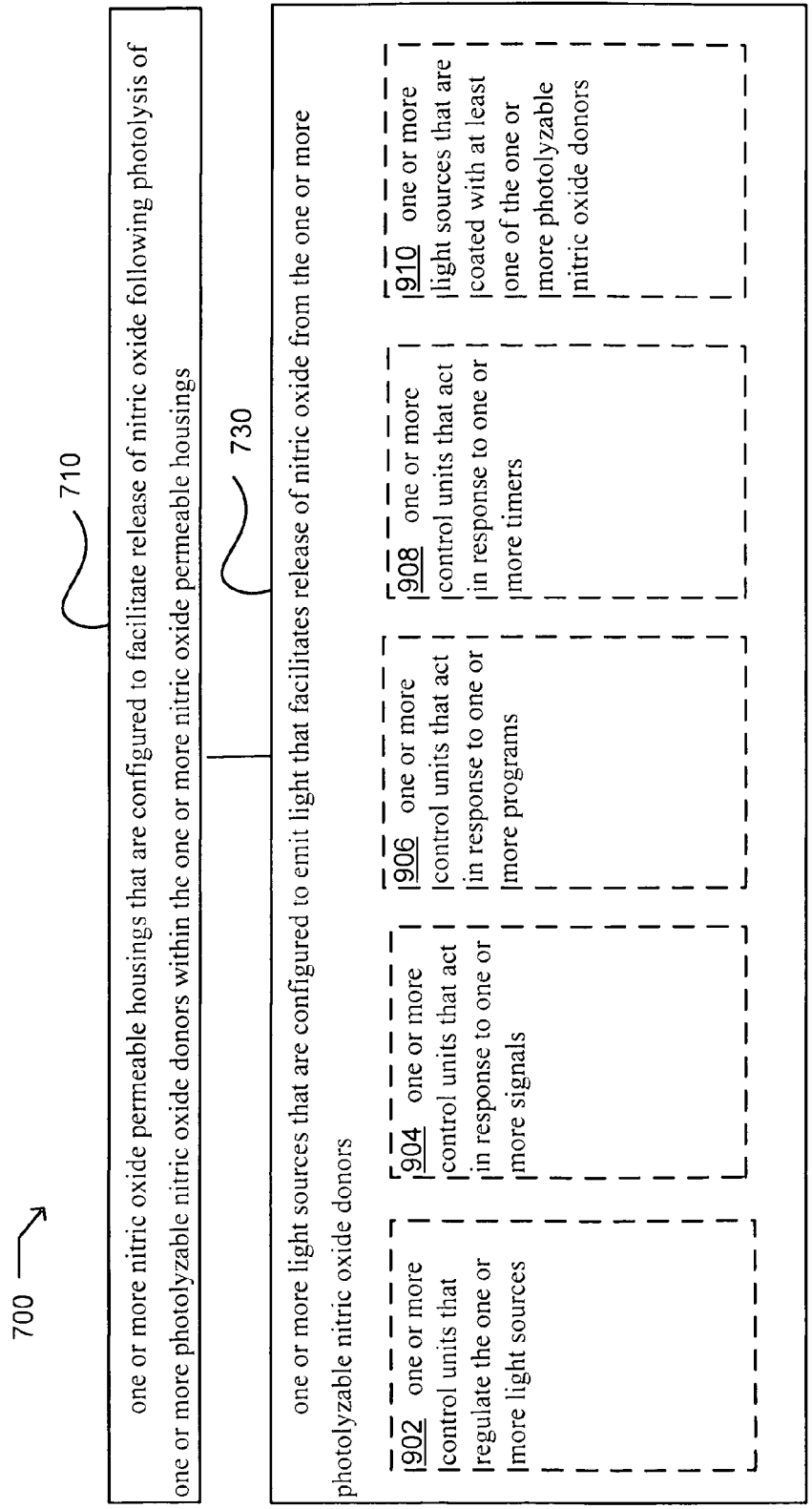
FIG. 9 illustrates alternate embodiments of module 730 of embodiment 700 of apparatus 102 within system 100.

FIG. 9 illustrates alternative embodiments of embodiment 700 of an apparatus 102 within system 100 of FIG. 7. FIG. 8 illustrates example embodiments of module 730 of an apparatus 102. Additional embodiments may include an embodiment 902, an embodiment 904, an embodiment 906, an embodiment 908, and/or an embodiment 910.

At embodiment 902, module 730 may include one or more control units that regulate the one or more light sources. In some embodiments, one or more light sources 108 may include one or more control units 126 that regulate the one or more light sources 108. One or more control units may regulate numerous aspects of one or more light sources 108. Examples of such aspects include, but are not limited to, intensity of emitted light, duration of emitted light, pulse frequency of emitted light, wavelengths of emitted light, and the like.

At embodiment 904, module 730 may include one or more control units that act in response to one or more signals. In some embodiments, one or more light sources 108 may include one or more control units 126 that act in response to one or more signals 116. In some embodiments, one or more control units 126 may include one or more receivers. Accordingly, in some embodiments, one or more control units 126 may be configured to receive one or more signals 116. In some embodiments, one or more control units 126 may receive one or more signals 116 that include commands for the one or more control units. For example, in some embodiments, one or more control units 126 may receive one or more signals 116 that command the one or more control units 126 to regulate operation of one or more light sources 108. Accordingly, in some embodiments, one or more control units 126 may regulate light emitted by one or more light sources 108. In some embodiments, one or more control units 126 may regulate one or more times when light is emitted by one or more light sources 108. In some embodiments, one or more control units 126 may regulate one or more times when light is not emitted by one or more light sources 108. In some embodiments, one or more control units 126 may regulate one or more wavelengths of light that are emitted by one or more light sources 108.

At embodiment 906, module 730 may include one or more control units that act in response to one or more programs. In some embodiments, one or more light sources 108 may include one or more control units 126 that act in response to one or more programs. For example, in some embodiments, one or more control units 126 may be responsive to a programmed set of instructions. In some embodiments, the one or more control units 126 may be directly programmed. For example, in some embodiments, one or more control units 126 may include a programmable memory that can include instructions. In some embodiments, the one or more control units 126 may receive instructions from a program that is associated with one or more management units 120.

At embodiment 908, module 730 may include one or more control units that act in response to one or more timers. In some embodiments, one or more light sources 108 may include one or more control units 126 that act in response to one or more timers. In some embodiments, one or more control units 126 may be configured to include one or more timers to which the one or more control units are responsive. In some embodiments, one or more control units 126 may be responsive to one or more timers that are remote from the one or more control units 126. For example, in some embodiments, one or more control units 126 may be responsive to one or more timers that are associated with one or more management units 120 that send instructions to the one or more control units 126.

At embodiment 910, module 730 may include one or more light sources that are coated with at least one of the one or more photolyzable nitric oxide donors. In some embodiments, one or more light sources 108 may include one or more light sources 108 that are coated with at least one of the one or more photolyzable nitric oxide donors 106. For example, in some embodiments, a light source 108 may be configured as a wand that emits light which can be coated with one or more photolyzable nitric oxide donors 106. In some embodiments, a light source 108 may be configured as a sheet that is coated with one or more photolyzable nitric oxide donors 106. In some embodiments, one or more light sources 108 may be partially coated with one or more photolyzable nitric oxide donors 106.

Figure 10:
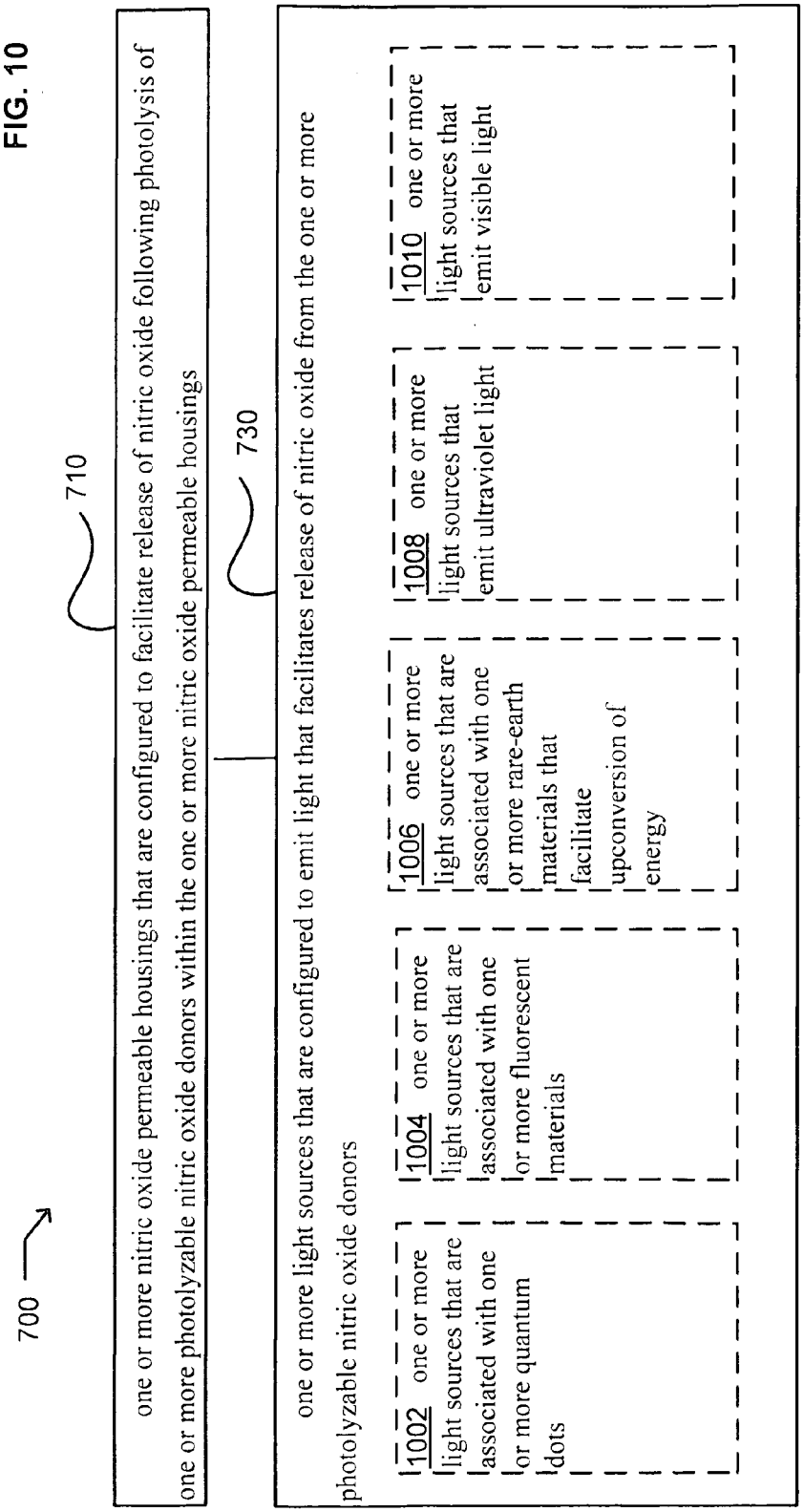
FIG. 10 illustrates alternate embodiments of module 730 of embodiment 700 of apparatus 102 within system 100.

FIG. 10 illustrates alternative embodiments of embodiment 700 of an apparatus 102 within system 100 of FIG. 7. FIG. 10 illustrates example embodiments of module 730 of an apparatus 102. Additional embodiments may include an embodiment 1002, an embodiment 1004, an embodiment 1006, an embodiment 1008, and/or an embodiment 1010.

At embodiment 1002, module 730 may include one or more light sources that are associated with one or more quantum dots. In some embodiments, one or more light sources 108 may include one or more light sources 108 that are associated with one or more quantum dots (e.g., U.S. Pat. No. 7,235,361; herein incorporated by reference). For example, in some embodiments, one or more light sources 108 may be configured to emit one or more wavelengths of light that are absorbed by one or more quantum dots. In some embodiments, one or more quantum dots may be configured to absorb light and then emit one or more wavelengths of light that cause release of nitric oxide from one or more nitric oxide donors. Accordingly, in some embodiments, emission from one or more first quantum dots may be tuned to facilitate release of nitric oxide from one or more first photolyzable nitric oxide donors 106 and emission from one or more second quantum dots may be tuned to facilitate release of nitric oxide from one or more second photolyzable nitric oxide donors 106.

At embodiment 1004, module 730 may include one or more light sources that are associated with one or more fluorescent materials. In some embodiments, one or more light sources 108 may include one or more light sources 108 that are associated with one or more fluorescent materials. Numerous fluorescent materials may be associated with one or more light sources 108. Examples of such materials include, but are not limited to, 1,4-diphenylbutadiene; 9,10-diphenylanthracene; benzene; biphenyl; ethyl-p-dimethylaminobenzoate; naphthalene; P-terphenyl; ethyl-p-dimethylaminobenzoate; stilbene; tryptophan; tyrosine; 1,2- diphenylacetylene; 7-methoxycoumarin-4-acetic acid; anthracene; indo-1; POPOP; P-quaterphenyl; pyrene; and the like.

At embodiment 1006, module 730 may include one or more light sources that are associated with one or more rare-earth materials that facilitate upconversion of energy. In some embodiments, one or more light sources 108 may include one or more light sources 108 that are associated with one or more rare-earth materials that facilitate upconversion of energy. In some embodiments, infrared light may be upconverted to visible light (e.g., Mendioroz et al., Optical Materials, 26:351-357 (2004). In some embodiments, infrared light may be upconverted to ultraviolet light (e.g., Mendioroz et al., Optical Materials, 26:351-357 (2004). In some embodiments, one or more light sources 108 may include one or more rare-earth materials (e.g., ytterbium-erbium, ytterbium-thulium, or the like) that facilitate upconversion of energy (e.g., U.S. Pat. No. 7,088,040; herein incorporated by reference). For example, in some embodiments, one or more light sources 108 may be associated with Nd3+ doped KPb2Cl5 crystals. In some embodiments, one or more light sources 108 may be associated with thiogallates doped with rare earths, such as CaGa2S4:Ce3+ and SrGa2S4:Ce3+. In some embodiments, one or more light sources 108 may be associated with aluminates that are doped with rare earths, such as YAlO3:Ce3+, YGaO3:Ce3+, Y(Al,Ga)O3:Ce3+, and orthosilicates M2SiO5:Ce3-(M:Sc, Y, Sc) doped with rare earths, such as, for example, Y2SiO5:Ce3+. In some embodiments, yttrium may be replaced by scandium or lanthanum (e.g., U.S. Pat. Nos. 6,812,500 and 6,327,074; herein incorporated by reference). Numerous materials that may be used to upconvert energy have been described (e.g., U.S. Pat. Nos. 5,956,172; 5,943,160; 7,235,189; 7,215,687; herein incorporated by reference).

At embodiment 1008, module 730 may include one or more light sources that emit ultraviolet light. In some embodiments, one or more light sources 108 may include one or more light sources 108 that emit ultraviolet light. In some embodiments, one or more light sources 108 may emit a broad spectrum of ultraviolet light. In some embodiments, one or more light sources 108 may emit a narrow spectrum of ultraviolet light. In some embodiments, one or more light sources 108 that emit one or more wavelengths of ultraviolet light that are specifically selected to release nitric oxide from one or more photolyzable nitric oxide donors 106. In some embodiments, one or more light sources 108 may emit ultraviolet light that does not include one or more wavelengths of light. In some embodiments, one or more light sources 108 may emit ultraviolet light that is selected to avoid and/or reduce damage to structures and/or tissues of a user 124. For example, in some embodiments, one or more light sources 108 may emit ultraviolet light that does not include wavelengths of light that are absorbed by nucleic acids. In some embodiments, one or more light sources 108 may emit ultraviolet light that does not include wavelengths of light that are absorbed by polypeptides. In some embodiments, one or more light sources 108 may emit light that does not include one or more wavelengths of ultraviolet light within the following range: 250-320 nm. For example, in some embodiments, one or more light sources 108 may not emit 260 nm light. In some embodiments, one or more light sources 108 may not emit 280 nm light. In some embodiments, one or more light sources 108 may not emit 260 nm light or 280 nm light. Accordingly, numerous combinations of wavelengths of light may be excluded from emission by one or more light sources 108. In some embodiments, light may be emitted continuously. In some embodiments, light may be emitted as a flash. In some embodiments, light may be emitted alternately as continuous light and a flash. In some embodiments, light may be emitted as a pulse. In some embodiments, light may be emitted continuously, as a flash, as a pulse, or substantially any combination thereof.

At embodiment 1010, module 730 may include one or more light sources that emit visible light. In some embodiments, one or more light sources 108 may include one or more light sources 108 that emit visible light. In some embodiments, one or more light sources 108 may emit a broad spectrum of visible light. In some embodiments, one or more light sources 108 may emit a narrow spectrum of visible light. In some embodiments, one or more light sources 108 may emit one or more wavelengths of visible light that are specifically selected to release nitric oxide from one or more photolyzable nitric oxide donors 106. In some embodiments, one or more light sources 108 may emit visible light that does not include one or more wavelengths of light. In some embodiments, one or more light sources 108 may emit visible light that is selected to avoid and/or reduce damage to structures and/or tissues of a user 124. Accordingly, numerous combinations of wavelengths of light may be excluded from emission by one or more light sources 108. In some embodiments, light may be emitted continuously. In some embodiments, light may be emitted as a flash. In some embodiments, light may be emitted alternately as continuous light and a flash. In some embodiments, light may be emitted as a pulse. In some embodiments, light may be emitted continuously, as a flash, as a pulse, or substantially any combination thereof. In some embodiments, the visible light may be upconverted.

Figure 11:
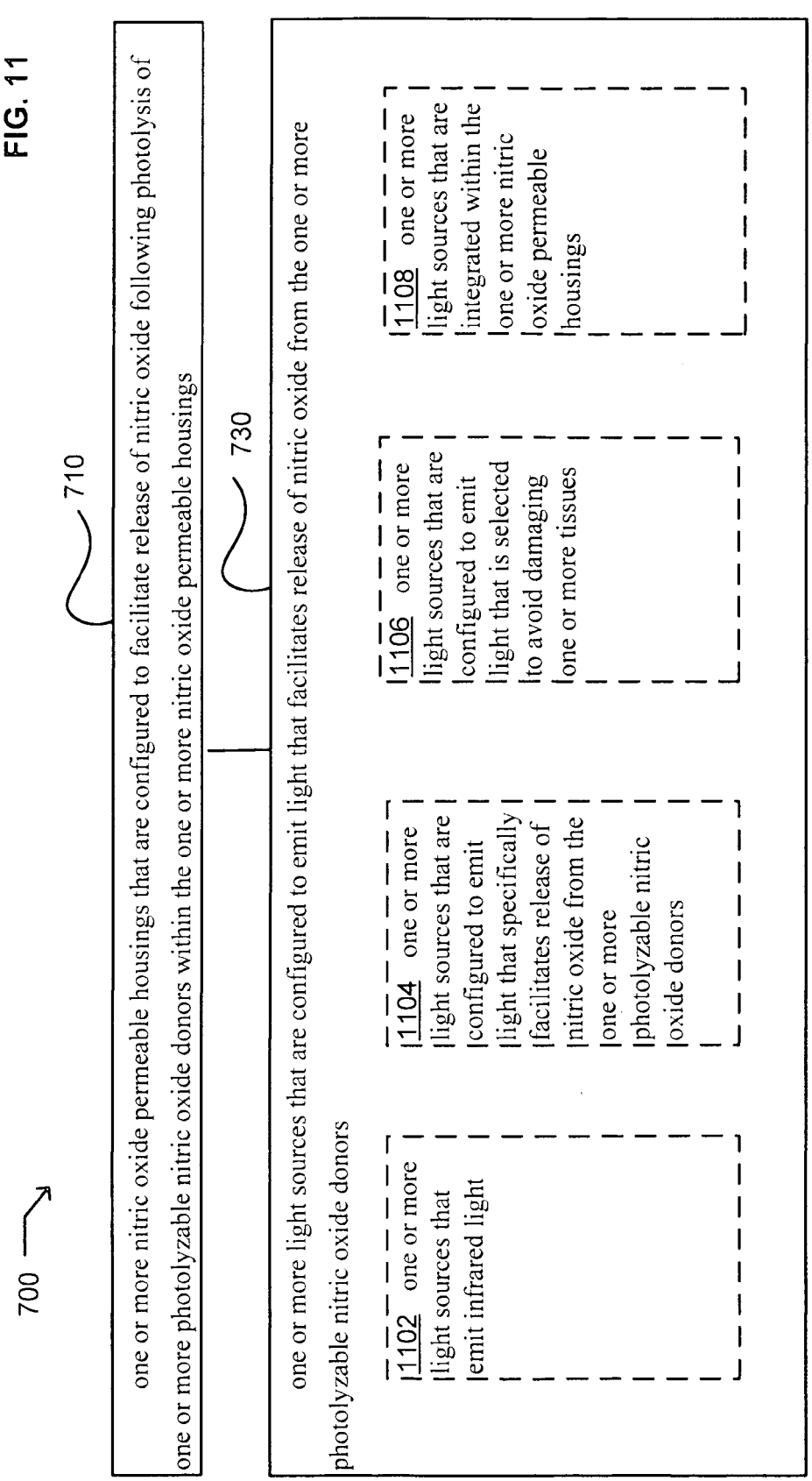
FIG. 11 illustrates alternate embodiments of module 730 of embodiment 700 of apparatus 102 within system 100.

FIG. 11 illustrates alternative embodiments of embodiment 700 of an apparatus 102 within system 100 of FIG. 7. FIG. 11 illustrates example embodiments of module 730 of an apparatus 102. Additional embodiments may include an embodiment 1102, an embodiment 1104, an embodiment 1106, and/or an embodiment 1108.

At embodiment 1102, module 730 may include one or more light sources that emit infrared light. In some embodiments, one or more light sources 108 may include one or more light sources 108 that emit infrared light. In some embodiments, one or more light sources 108 may emit a narrow spectrum of infrared light. In some embodiments, one or more light sources 108 may emit one or more wavelengths of infrared light that are specifically selected to release nitric oxide from one or more photolyzable nitric oxide donors 106. In some embodiments, one or more light sources 108 may emit infrared light that does not include one or more wavelengths of light. In some embodiments, one or more light sources 108 may emit infrared light that is selected to avoid and/or reduce damage to structures and/or tissues of a user 124. Accordingly, numerous combinations of wavelengths of light may be excluded from emission by one or more light sources 108. In some embodiments, light may be emitted continuously. In some embodiments, light may be emitted as a flash. In some embodiments, light may be emitted alternately as continuous light and a flash. In some embodiments, light may be emitted as a pulse. In some embodiments, light may be emitted continuously, as a flash, as a pulse, or substantially any combination thereof. In some embodiments, the infrared light may be upconverted.

At embodiment 1104, module 730 may include one or more light sources that are configured to emit light that specifically facilitates release of nitric oxide from the one or more photolyzable nitric oxide donors. In some embodiments, one or more light sources 108 may include one or more light sources 108 that emit light that specifically facilitates release of nitric oxide from the one or more photolyzable nitric oxide donors. For example, in some embodiments, one or more light sources 108 may be configured to emit light that includes one or more wavelengths of light that correspond to the absorption maximum for one or more nitric oxide donors. Examples of nitric oxide donors and their associated $\lambda_{max}$ (nm) are provided in Table I below. Accordingly, one or more light sources 108 may be configured to emit numerous wavelengths of light.

and/or tissues of a user 124. For example, in some embodiments, one or more light sources 108 may emit light that does not include wavelengths of light that are absorbed by nucleic acids. In some embodiments, one or more light sources 108 may emit light that does not include wavelengths of light that are absorbed by polypeptides. In some embodiments, one or more light sources 108 may emit light that does not include one or more wavelengths of light within the following range:

TABLE I

Example Nitric Oxide Donors

| Compound Name | $\lambda_{max}$ (nm) |
|---|---|
| $O^2$-(Acetoxymethyl) 1-(N,N-Diethylamino)diazen-1-ium-1,2-diolate | 230 |
| $O^2$-(Acetoxymethyl) 1-(Pyrrolidin-1-yl)diazen-1-ium-1,2-diolate | 256 |
| Sodium 1-(N-Benzyl-N-methylamino)diazen-1-ium-1,2-diolate | 252 |
| $O^2$-[(2,3,4,6-Tetra-O-acetyl)-β-D-glucosyl] 1-[4-(2,3-Dihydroxypropyl)piperazin-1 | 232 |
| Sodium 1-[4-(2,3-Dihydroxypropyl)piperazin-1-yl-]diazen-1-ium-1,2-diolate | 248.5 |
| $O^2$-Methyl 1-[(4-Carboxamido)piperidin-1-yl]diazen-1-ium-1,2-diolate | 241 |
| $O^2$-(2-Chloropyrimidin-4-yl) 1-(Pyrrolidin-1-yl)diazen-1-ium-1,2-diolate | 274 |
| $O^2$-(2,4-Dinitrophenyl) 1-[4-(N,N-Diethylcarboxamido)piperazin-1-yl]diazen-1-ium-1,2-diolate | 300 |
| $O^2$-(2,4-Dinitrophenyl) 1-(4-Nicotinylpiperazin-1-yl)diazen-1-ium-1,2-diolate | 300 |
| $O^2$-(2,4-Dinitrophenyl) 1-{4-[2-(4-{2-Methylpropyl}phenyl)propionyl]piperazin-1-yl}diazen-1-ium-1,2-diolate | 300 |
| Sodium 1-(4-Benzyloxycarbonylpiperazin-1-yl)diazen-1-ium-1,2-diolate | 252 |
| $O^2$-(2,4-Dinitrophenyl) 1-[4-(tert-Butoxycarbonyl)piperazin-1-yl]diazen-1-ium-1,2-diolate | 299 |
| $O^2$-(2,4-Dinitrophenyl) 1-(4-Acetylpiperazin-1-yl)diazen-1-ium-1,2-diolate | 394 |
| $O^2$-(2,4-Dinitrophenyl) 1-[4-(Succinimidoxycarbonyl)piperazin-1-yl]diazen-1-ium-1,2-diolate | 300 |
| $O^2$-(2,4-Dinitrophenyl) 1-(Piperazin-1-yl)diazen-1-ium-1,2-diolate, Hydrochloride Salt | 297 |
| $O^2$-(2,3,4,6-Tetra-O-acetyl-D-glucopyranosyl) 1-(N,N-Diethylamino)diazen-1-ium-1,2-diolate | 228 |
| $O^2$-(-D-Glucopyranosyl) 1-(N,N-Diethylamino)diazen-1-ium-1,2-diolate | 228 |
| Sodium (Z)-1-(N,N-Diethylamino)diazen-1-ium-1,2-diolate | 250 |
| 1-[N-(2-Aminoethyl)-N-(2-ammonioethyl)amino]diazen-1-ium-1,2-diolate | 252 |
| Sodium 1-(N,N-Dimethylamino)diazen-1-ium-1,2-diolate | 250 |
| $O^2$-(2,4-Dinitrophenyl) 1-(N,N-Diethylamino)diazen-1-ium-1,2-diolate | 302 |
| 1-[N-(3-Aminopropyl)-N-3-ammoniopropyl]diazen-1-ium-1,2-diolate | 252 |
| 1-[N-(3-Aminopropyl)-N-(3-ammoniopropyl]diazen-1-ium-1,2-diolate | 252 |
| Bis-diazeniumdiolated benzyl imidate dehydrate | 264 |
| p-Bisdiazeniumdiolated benzene | 316 |
| Methane Trisdiazeniumdiolate trihydrate | 316 |
| $O^2$-(β-D-Glucopyranosyl) 1-(Isopropylamino)diazen-1-ium-1,2-diolate | 278 |
| Sodium 1-[4-(5-Dimethylamino-1-naphthalenesulfonyl)piperazin-1-yl]diazen-1-ium-1,2-diolate | 344 |
| 1-(2-Methyl-1-propenyl)piperidine diazeniumdiolate | 246 |
| 1-(2-Methyl-1-propenyl)pyrrolidine diazeniumdiolate | 246 |
| $O^2$-Vinyl 1-(Pyrrolidin-1-yl)diazen-1-ium-1,2-diolate | 268 |
| 1-{N-[3-Aminopropyl]-N-[4-(3-aminopropylammoniobutyl)]}diazen-1-ium-1,2-diolate | 252 |
| Disodium 1-[(2-Carboxylato)pyrrolidin-1-yl]diazen-1-ium-1,2-diolate | 252 |
| 1-[N-(3-Ammoniopropyl)-N-(n-propyl)amino]diazen-1-ium-1,2-diolate | 250 |
| (Z)-1-{N-Methyl-N-[6-(N-methylammoniohexyl)amino]}diazen-1-ium-1,2-diolate | 250 |
| $O^2$-(2,4-Dinitrophenyl) 1-[(4-Ethoxycarbonyl)piperazin-1-yl]diazen-1-ium-1,2-diolate | 300 |

At embodiment 1106, module 730 may include one or more light sources that are configured to emit light that is selected to avoid damaging one or more tissues. In some embodiments, one or more light sources 108 may include one or more light sources 108 that are configured to emit light that is selected to avoid damaging one or more tissues. In some embodiments, one or more light sources 108 may emit light that is selected to avoid and/or reduce damage to structures 250-320 nm. For example, in some embodiments, one or more light sources 108 may not emit 260 nm light. In some embodiments, one or more light sources 108 may not emit 280 nm light. In some embodiments, one or more light sources 108 may not emit 260 nm light or 280 nm light. Accordingly, numerous combinations of wavelengths of light may be excluded from emission by one or more light sources 108. In some embodiments, light may be emitted continuously. In some embodiments, light may be emitted as a flash. In some embodiments, light may be emitted alternately as continuous light and a flash. In some embodiments, light may be emitted as a pulse.

At embodiment 1108, module 730 may include one or more light sources that are integrated within the one or more nitric oxide permeable housings. In some embodiments, one or more light sources 108 may include one or more light sources 108 that are integrated within the one or more nitric oxide permeable housings. In some embodiments, one or more light sources 108 may form an integral part of a nitric oxide permeable housing. For example, in some embodiments, one or more light sources 108 may include one or more fiber optic fibers that are embedded within one or more polymeric materials used to form a nitric oxide permeable housing. In some embodiments, one or more light sources 108 may be included within a composition that includes one or more photolyzable nitric oxide donors 106 which is included within a nitric oxide permeable housing. Accordingly, one or more light sources 108 may be integrated into a nitric oxide permeable housing in numerous ways.

Figure 12:
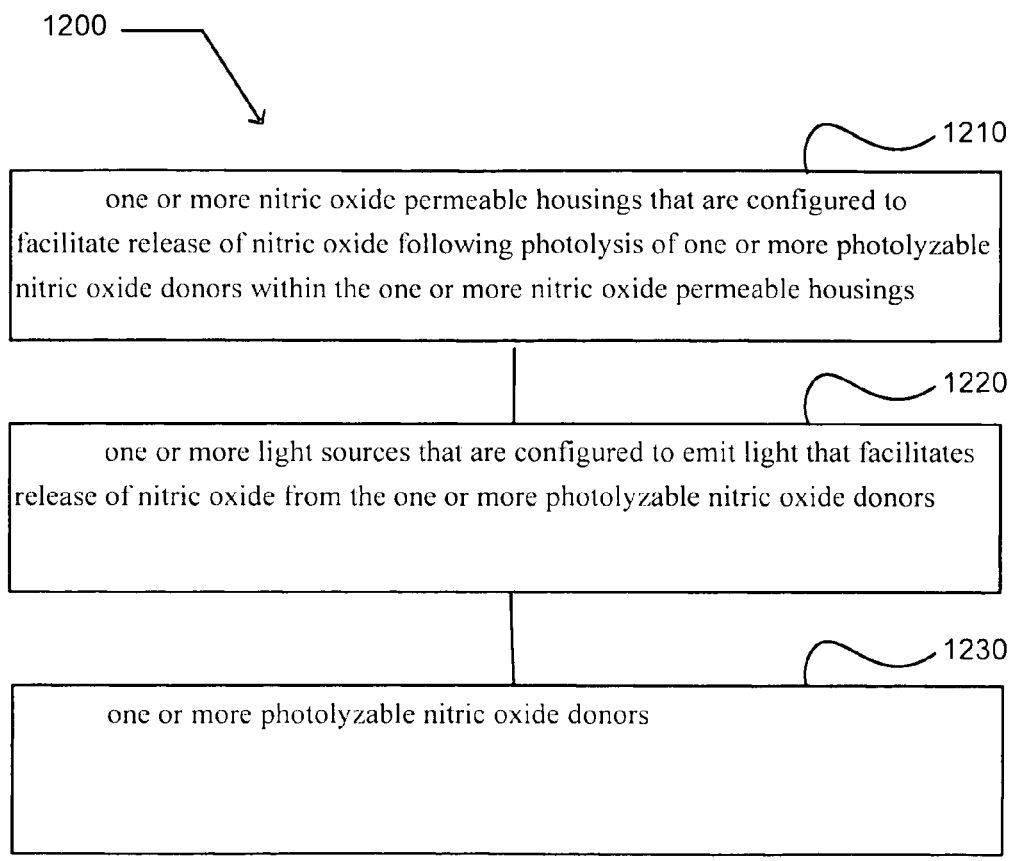
FIG. 12 illustrates embodiment 1200 of apparatus 102 within system 100.

FIG. 12 illustrates embodiment 1200 of an apparatus 102 within system 100. In FIG. 12, discussion and explanation may be provided with respect to the above-described example of FIG. 1, and/or with respect to other examples and contexts. In some embodiments, module 210 of FIG. 2 may correspond to module 1210 as described with respect to embodiment 1200 of an apparatus 102 within system 100. In some embodiments, module 520 of FIG. 5 may correspond to module 1230 as described with respect to embodiment 1200 of an apparatus 102 within system 100. In some embodiments, module 730 of FIG. 7 may correspond to module 1220 as described with respect to embodiment 1200 of an apparatus 102 within system 100. However, it should be understood that the modules may execute operations in a number of other environments and contexts, and/or modified versions of FIG. 1. Also, although the various modules are presented in the sequence(s) illustrated, it should be understood that the various modules may be configured in numerous orientations.

The embodiment 1200 may include module 1210 that includes one or more nitric oxide permeable housings that are configured to facilitate release of nitric oxide following photolysis of one or more photolyzable nitric oxide donors within the one or more nitric oxide permeable housings. In some embodiments, an apparatus 102 may include one or more nitric oxide permeable housings 104 that are configured to facilitate release of nitric oxide following photolysis of one or more photolyzable nitric oxide donors 106 within the one or more nitric oxide permeable housings. In some embodiments, a nitric oxide permeable housing 104 may include one or more light sources 108. In some embodiments, a nitric oxide permeable housing 104 may include one or more light sources 108 that are configured to emit light that facilitates release of nitric oxide from one or more photolyzable nitric oxide donors 106. In some embodiments, a nitric oxide permeable housing 104 may include one or more photolyzable nitric oxide donors 106. In some embodiments, a nitric oxide permeable housing 104 may be configured for implantation within a user 124. For example, in some embodiments, a nitric oxide permeable housing 104 may be configured to facilitate delivery of nitric oxide to the genital region of a user 124. In some embodiments, a nitric oxide permeable housing 104 may be configured to facilitate delivery of nitric oxide to the vasculature of a user 124. In some embodiments, a nitric oxide permeable housing 104 may be configured to facilitate delivery of nitric oxide to a surface. In some embodiments, a nitric oxide permeable housing 104 may be configured to be included within a bandage, a patch, tape, clothing, and the like. In some embodiments, a nitric oxide permeable housing 104 may include one or more nitric oxide permeable layers. In some embodiments, a nitric oxide permeable housing 104 may include one or more valves that are configured to provide for passage of nitric oxide from the nitric oxide permeable housing 104. In some embodiments, a nitric oxide permeable housing 104 may include one or more controllable valves that are configured to provide for passage of nitric oxide from the nitric oxide permeable housing 104. Accordingly, in some embodiments, a nitric oxide permeable housing 104 may include one or more control units 126. In some embodiments, one or more control units 126 may be configured to control one or more valves. In some embodiments, one or more control units 126 may be configured to control one or more light sources 108.

The embodiment 1200 may include module 1220 that includes one or more light sources that are configured to emit light that facilitates release of nitric oxide from the one or more photolyzable nitric oxide donors. In some embodiments, an apparatus 102 may include one or more light sources 108 that are configured to emit light that facilitates release of nitric oxide from the one or more photolyzable nitric oxide donors 106. A light source 108 may be configured in numerous ways. For example, in some embodiments, a light source 108 may include a chemiluminescent light source 108. In some embodiments, a light source 108 may include a phosphorescent light source 108. In some embodiments, a light source 108 may include a light emitter that is coupled to a power supply. For example, in some embodiments, a light source 108 may include one or more light emitting diodes that are coupled to one or more power supplies. Examples of power supplies include, but are not limited to, capacitors, batteries, electromagnetic receivers 110, and the like. In some embodiments, one or more light sources 108 may be configured to emit light that specifically facilitates release of nitric oxide from one or more photolyzable nitric oxide donors 106. For example, in some embodiments, one or more light sources 108 may be configured to emit one or more wavelengths of light that facilitate photodecomposition of one or more photolyzable nitric oxide donors 106. In some embodiments, one or more light sources 108 may be configured such they do not emit one or more wavelengths of light that do not facilitate photodecomposition of one or more photolyzable nitric oxide donors 106. Accordingly, in some embodiments, one or more light sources 108 may be configured to emit light that is matched to one or more photolyzable nitric oxide donors 106 and causes photodecomposition of the one or more photolyzable nitric oxide donors 106. In some embodiments, one or more light sources 108 may be configured such that they do not emit light that cross-links biological structures (e.g., proteins) or that causes the formation of DNA adducts. Accordingly, in some embodiments, one or more light sources 108 may be configured to emit light that photolyzes one or more photolyzable nitric oxide donors 106 with reduced damage to surrounding tissue. For example, in some embodiments, one or more light sources 108 may be configured to emit visible light ($\lambda=550$ nm) to facilitate homolytic decomposition of S-nitrosoglutathione to generate nitric oxide (e.g., Singh et al., FEBS Letters, 360:47-51 (1995)). In some embodiments, ultraviolet light may be used to facilitate release of nitric oxide from one or more photolyzable nitric oxide donors 106. For example, in some embodiments, one or more light sources 108 may be configured to emit ultraviolet light ($\lambda=355$ nm) to release nitric oxide from S-nitrosothiols (e.g., Rotta et al., Braz. J. Med. Biol. Res., 36:587-594 (2003)). In some embodiments, one or more light sources 108 may be configured to emit light over a broad range of wavelengths that will facilitate release of nitric oxide from one or more photolyzable nitric oxide donors 106. For example, in some embodiments, $O^2$-benzyl substituted diazeniumdiolates, $O^2$-napthylmethyl substituted diazeniumdiolates, and/or $O^2$-napththylallyl substituted diazeniumdiolates may be photolyzed by light over a broad range of wavelengths ($\lambda$=254 nm to $\lambda$=700 nm) (e.g., U.S. Pat. No. 7,122,529).

The embodiment 1200 may include module 1230 that includes one or more photolyzable nitric oxide donors. In some embodiments, an apparatus 102 may include one or more photolyzable nitric oxide donors 106. In some embodiments, an apparatus 102 may include one or more photolyzable nitric oxide donors 106 that release nitric oxide upon photolysis. Examples of such photolyzable nitric oxide donors 106 include, but are not limited to, diazeniumdiolates (e.g., U.S. Pat. Nos. 7,105,502; 7,122,529; 6,673,338; herein incorporated by reference), trans-[RuCl([5]aneN4)NO]+2 (Ferezin et al., Nitric Oxide, 13:170-175 (2005), Bonaventura et al., Nitric Oxide, 10:83-91 (2004)), nitrosyl ligands (e.g., U.S. Pat. No. 5,665,077; herein incorporated by reference, Chmura et al., Nitric Oxide, 15:370-379 (2005), Flitney et al., Br. J. Pharmacol., 107:842-848 (1992), Flitney et al., Br. J. Pharmacol., 117:1549-1557 (1996), Matthews et al., Br. J. Pharmacol., 113:87-94 (1994)), 6-Nitrobenzo[α]pyrene (e.g., Fukuhara et al., J. Am. Chem. Soc., 123:8662-8666 (2001)), S-nitroso-glutathione (e.g., Rotta et al., Braz. J. Med. Res., 36:587-594 (2003), Flitney and Megson, J. Physiol., 550:819-828 (2003)), S-nitrosothiols (e.g., Andrews et al., British Journal of Pharmacology, 138:932-940 (2003), Singh et al., FEBS Lett., 360:47-51 (1995)), 2-Methyl-2-nitrosopropane (e.g., Pou et al., Mol. Pharm., 46:709-715 (1994), Wang et al., Chem. Rev., 102:1091-1134 (2002)), imidazolyl derivatives (e.g., U.S. Pat. No. 5,374,710; herein incorporated by reference).

Figure 13:
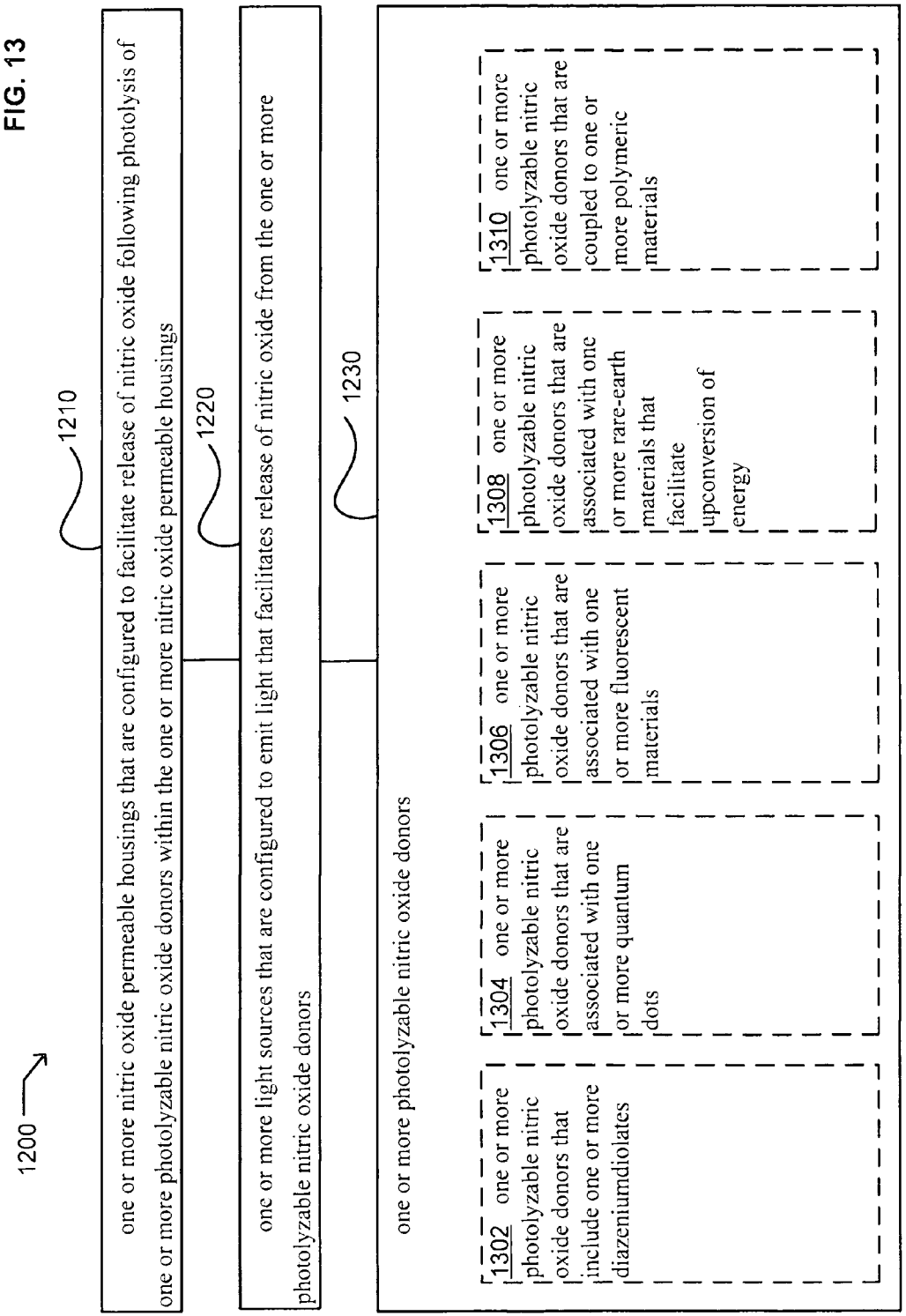
FIG. 13 illustrates alternate embodiments of module 1230 of embodiment 1200 of apparatus 102 within system 100.

FIG. 13 illustrates alternative embodiments of embodiment 1200 of an apparatus 102 within system 100 of FIG. 12. FIG. 13 illustrates example embodiments of module 1230 of an apparatus 102. Additional embodiments may include an embodiment 1302, an embodiment 1304, an embodiment 1306, an embodiment 1308, and/or an embodiment 1310.

At embodiment 1302, module 1230 may include one or more photolyzable nitric oxide donors that include one or more diazeniumdiolates. In some embodiments, one or more photolyzable nitric oxide donors 106 may include one or more photolyzable nitric oxide donors 106 that include one or more diazeniumdiolates. Many photolyzable nitric oxide donors 106 that are diazeniumdiolates are known and have been described (e.g., U.S. Pat. No. 7,122,529). Examples of such diazeniumdiolates include, but are not limited to, $O^2$-benzyl, $O^2$-naphthylmethyl substituted diazeniumdiolates and $O^2$-naphthylallyl substituted diazeniumdiolates.

At embodiment 1304, module 1230 may include one or more photolyzable nitric oxide donors that are associated with one or more quantum dots. In some embodiments, one or more photolyzable nitric oxide donors 106 may include one or more photolyzable nitric oxide donors 106 that are associated with one or more quantum dots. In some embodiments, one or more quantum dots may be tuned to emit light that facilitates photolysis of one or more nitric oxide donors. In some embodiments, a quantum dot may be tuned to emit light that specifically facilitates photolysis of one or more nitric oxide donors. For example, in some embodiments, one or more quantum dots may emit select wavelengths of light that correspond to wavelengths of light that cause photolysis of one or more nitric oxide donors. In some embodiments, one or more quantum dots may be selected that absorb light emitted by one or more light sources 108 and emit light that facilitates photolysis of one or more nitric oxide donors.

At embodiment 1306, module 1230 may include one or more photolyzable nitric oxide donors that are associated with one or more fluorescent materials. In some embodiments, one or more photolyzable nitric oxide donors 106 may include one or more photolyzable nitric oxide donors 106 that are associated with one or more fluorescent materials. Numerous fluorescent materials may be associated with one or more photolyzable nitric oxide donors 106. Examples of such materials include, but are not limited to, 1,4-diphenylbutadiene; 9,10-diphenylanthracene; benzene; biphenyl; ethyl-p-dimethylaminobenzoate; naphthalene; P-terphenyl; ethyl-p-dimethylaminobenzoate; stilbene; tryptophan; tyrosine; 1,2-diphenylacetylene; 7-methoxycoumarin-4-acetic acid; anthracene; indo-1; POPOP; P-quaterphenyl; pyrene; and the like.

At embodiment 1308, module 1230 may include one or more photolyzable nitric oxide donors that are associated with one or more rare-earth materials that facilitate upconversion of energy. In some embodiments, one or more photolyzable nitric oxide donors 106 may include one or more photolyzable nitric oxide donors 106 that are associated with one or more rare-earth materials that facilitate upconversion of energy. In some embodiments, infrared light may be upconverted to visible light (e.g., Mendioroz et al., Optical Materials, 26:351-357 (2004). In some embodiments, infrared light may be upconverted to ultraviolet light (e.g., Mendioroz et al., Optical Materials, 26:351-357 (2004). In some embodiments, one or more photolyzable nitric oxide donors 106 may be associated with one or more rare-earth materials (e.g., ytterbium-erbium, ytterbium-thulium or the like) that facilitate upconversion of energy (e.g., U.S. Pat. No. 7,088,040; herein incorporated by reference). For example, in some embodiments, one or more photolyzable nitric oxide donors 106 may be associated with $Nd^{3+}$ doped $KPb_2Cl_5$ crystals. In some embodiments, one or more photolyzable nitric oxide donors 106 may be associated with thiogallates doped with rare earths, such as $CaGa_2S_4:Ce^{3+}$ and $SrGa_2S_4:Ce^{3+}$. In some embodiments, one or more photolyzable nitric oxide donors 106 may be associated with aluminates that are doped with rare earths, such as $YAlO_3:Ce^{3+}$, $YGaO_3:Ce^{3+}$, $Y(Al,Ga)O_3:Ce^{3+}$, and orthosilicates $M_2SiO_5:Ce^{3+}$ (M:Sc, Y, Sc) doped with rare earths, such as, for example, $Y_2SiO_5:Ce^{3+}$. In some embodiments, yttrium may be replaced by scandium or lanthanum (e.g., U.S. Pat. Nos. 6,812,500 and 6,327,074; herein incorporated by reference). Numerous materials that may be used to upconvert energy have been described (e.g., U.S. Pat. Nos. 5,956,172; 5,943,160; 7,235,189; 7,215,687; herein incorporated by reference).

At embodiment 1310, module 1230 may include one or more photolyzable nitric oxide donors that are coupled to one or more polymeric materials. In some embodiments, one or more photolyzable nitric oxide donors 106 may include one or more photolyzable nitric oxide donors 106 that are coupled to one or more polymeric materials. For example, in some embodiments, one or more polymer matrices may be impregnated with one or more photolyzable nitric oxide donors 106 (e.g., U.S. Pat. No. 5,994,444). In some embodiments, one or more photolyzable nitric oxide donors 106 may be bound to a polymer. Methods that can be used to couple nitric oxide donors to a polymeric matrix have been reported (e.g., U.S. Pat. No. 5,405,919). In some embodiments, one or more polymers to which one or more photolyzable nitric oxide donors 106 are coupled may be used to construct one or more housings.

Figure 14:
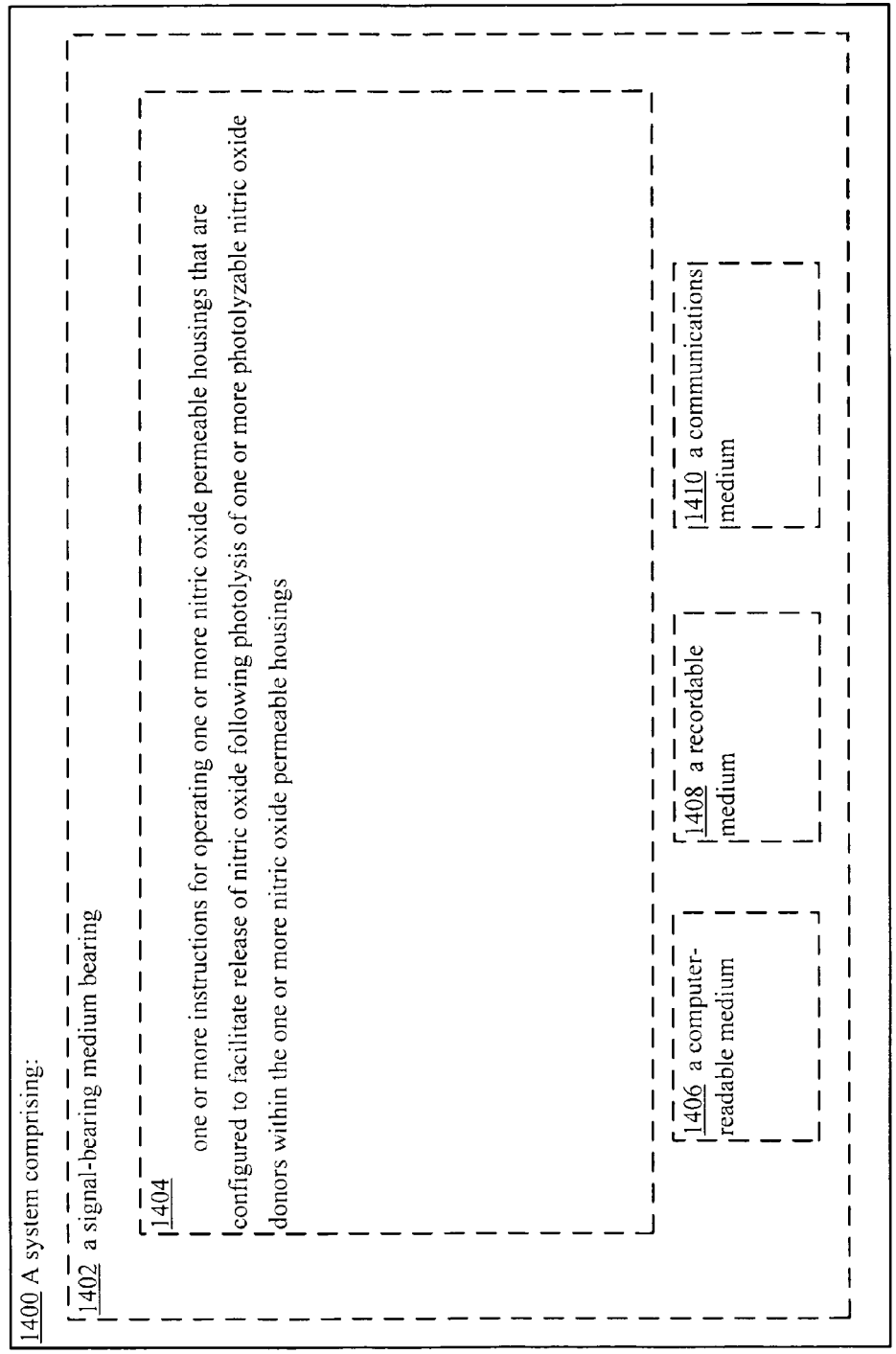
FIG. 14 illustrates a partial view of a system 1400 that includes a computer program for executing a computer process on a computing device.

FIG. 14 illustrates a partial view of a system 1400 that includes a computer program 1404 for executing a computer process on a computing device. An embodiment of system 1400 is provided using a signal-bearing medium 1402 bearing one or more instructions for operating one or more nitric oxide permeable housings that are configured to facilitate release of nitric oxide following photolysis of one or more photolyzable nitric oxide donors within the one or more nitric oxide permeable housings. The one or more instructions may be, for example, computer executable and/or logic-implemented instructions. In some embodiments, the signal-bearing medium 1402 may include a computer-readable medium 1406. In some embodiments, the signal-bearing medium 1402 may include a recordable medium 1408. In some embodiments, the signal-bearing medium 1402 may include a communications medium 1410.

Figure 15:
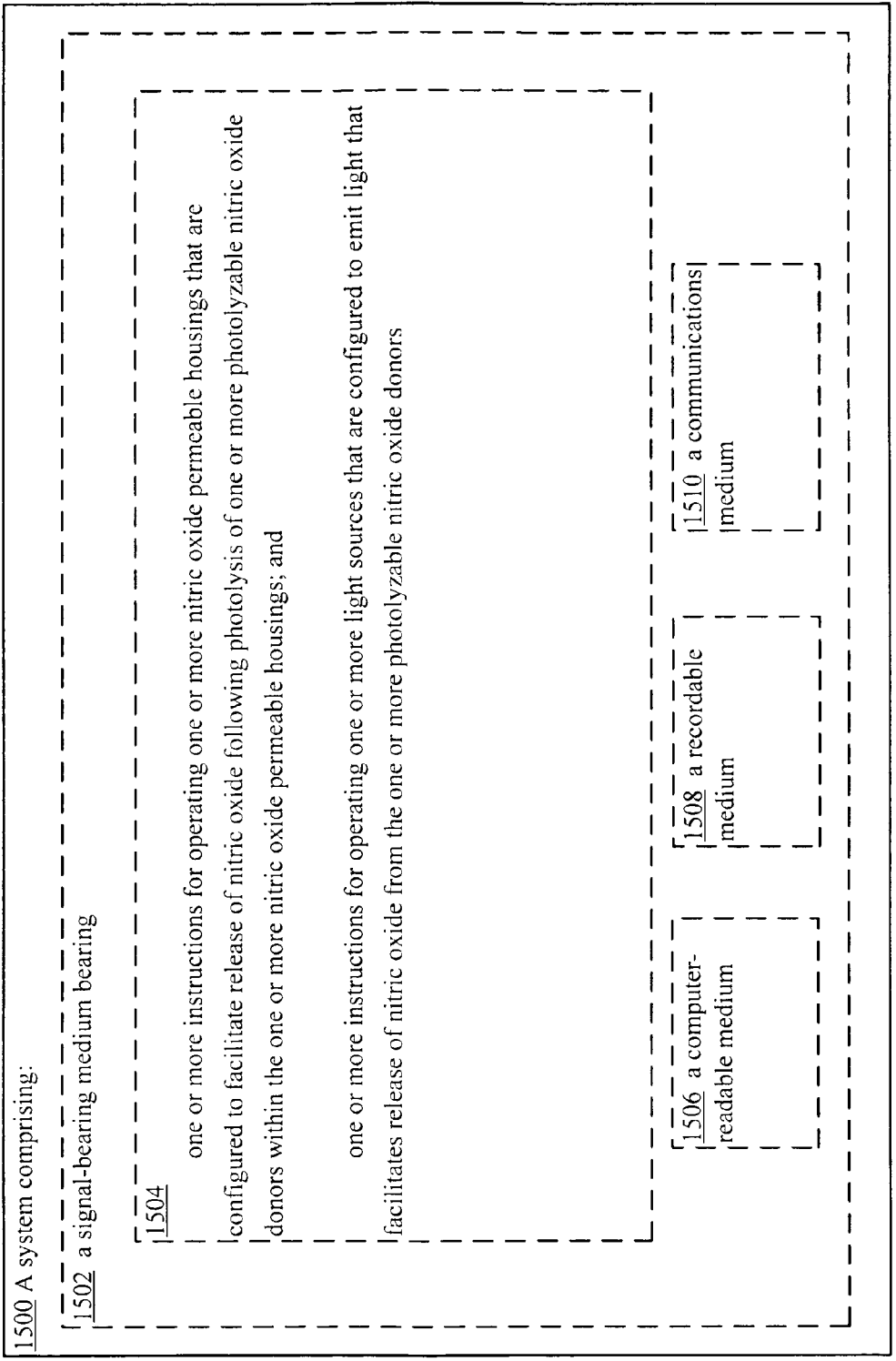
FIG. 15 illustrates a partial view of a system 1500 that includes a computer program for executing a computer process on a computing device.

FIG. 15 illustrates a partial view of a system 1500 that includes a computer program 1504 for executing a computer process on a computing device. An embodiment of system 1500 is provided using a signal-bearing medium 1502 bearing one or more instructions for operating one or more nitric oxide permeable housings that are configured to facilitate release of nitric oxide following photolysis of one or more photolyzable nitric oxide donors within the one or more nitric oxide permeable housings; and one or more instructions for operating one or more light sources that are configured to emit light that facilitates release of nitric oxide from the one or more photolyzable nitric oxide donors. The one or more instructions may be, for example, computer executable and/or logic-implemented instructions. In some embodiments, the signal-bearing medium 1502 may include a computer-readable medium 1506. In some embodiments, the signal-bearing medium 1502 may include a recordable medium 1508. In some embodiments, the signal-bearing medium 1502 may include a communications medium 1510.

FIG. 16A illustrates an embodiment of apparatus 102. Apparatus 102 is shown in association with photolyzable nitric oxide donor 106 and light source 108. The photolyzable nitric oxide donor 106 and light source 108 are enclosed within a nitric oxide permeable housing 104 that includes a nitric oxide permeable membrane 1600.

FIG. 16B illustrates an embodiment of apparatus 102. Apparatus 102 is shown in association with photolyzable nitric oxide donor 106 and light source 108. The photolyzable nitric oxide donor 106 and light source 108 are enclosed within a nitric oxide permeable housing 104 that includes a nitric oxide permeable membrane 1600.

FIG. 16C illustrates an embodiment of apparatus 102. Apparatus 102 is shown in association with photolyzable nitric oxide donor 106 and light source 108. Photolyzable nitric oxide donor 106 is shown enclosed within a nitric oxide permeable housing 104 that includes a nitric oxide permeable membrane 1600. Light source 108 is shown as being positioned within a cavity of the nitric oxide permeable housing 104 and associated with a control unit 126.

FIG. 17A illustrates an embodiment of apparatus 102. Apparatus 102 is shown in association with photolyzable nitric oxide donor 106 and a nitric oxide permeable membrane 1600. Light source 108 is shown as being positioned within the nitric oxide permeable housing 104 in association with a light permeable window 1700.

FIG. 17B illustrates an embodiment of apparatus 102. Apparatus 102 is shown in association with photolyzable nitric oxide donor 106 and a nitric oxide permeable membrane 1600. Light source 108 is shown as being positioned within the nitric oxide permeable housing 104 in association with a light permeable window 1700.

FIG. 17C illustrates an embodiment of apparatus 102. Apparatus 102 is shown in association with photolyzable nitric oxide donor 106 and a nitric oxide permeable membrane 1600. Light source 108 is shown as being positioned within a cavity of the nitric oxide permeable housing 104 and associated with a control unit 126.

FIG. 18A illustrates an embodiment of apparatus 102. Photolyzable nitric oxide donor 106 is shown enclosed within a nitric oxide permeable housing 104 that includes a controllable valve 1800. Light source 108 is shown as being positioned within the nitric oxide permeable housing 104. Receiver 1802 is associated with the nitric oxide permeable housing 104.

FIG. 18B illustrates an embodiment of apparatus 102. Photolyzable nitric oxide donor 106 is shown enclosed within a nitric oxide permeable housing 104 that includes a controllable valve 1800. Light source 108 is shown as being positioned within the nitric oxide permeable housing 104. Receiver 1802 is associated with the nitric oxide permeable housing 104.

FIG. 18C illustrates an embodiment of apparatus 102. Photolyzable nitric oxide donor 106 is shown enclosed within a nitric oxide permeable housing 104 that includes a controllable valve 1800. Light source 108 is shown as being positioned within a cavity of the nitric oxide permeable housing 104 and associated with a control unit 126.

FIG. 19A illustrates an embodiment of nitric oxide permeable housing 104. Nitric oxide permeable housing 104 is illustrated as including a nitric oxide impermeable portion 1920 of the nitric oxide permeable housing 104 and a nitric oxide permeable membrane 1600. The nitric oxide permeable housing 104 includes a cavity 1910 configured to accept one or more light sources 108 and a cavity 1900 configured to accept one or more photolyzable nitric oxide donors 106.

FIG. 19B illustrates an embodiment of nitric oxide permeable housing 104. Nitric oxide permeable housing 104 is illustrated as including a nitric oxide permeable membrane 1600 that includes a cavity 1900 configured to accept one or more photolyzable nitric oxide donors 106. The nitric oxide permeable housing 104 includes a cavity 1910 configured to accept one or more light sources 108. Nitric oxide permeable housing 104 includes a light permeable window 1700 that separates the cavity 1900 configured to accept one or more photolyzable nitric oxide donors 106 from the cavity 1910 configured to accept one or more light sources 108.

FIG. 19C illustrates an embodiment of nitric oxide permeable housing 104. Nitric oxide permeable housing 104 is illustrated as including a nitric oxide impermeable portion 1920 of the nitric oxide permeable housing 104 and a nitric oxide permeable membrane 1600. Nitric oxide permeable housing 104 is illustrated as including a cavity 1900 configured to accept one or more photolyzable nitric oxide donors 106. The nitric oxide permeable housing 104 includes a cavity 1910 configured to accept one or more light sources 108. Nitric oxide permeable housing 104 includes a light permeable window 1700 that separates the cavity 1900 configured to accept one or more photolyzable nitric oxide donors 106 from the cavity 1910 configured to accept one or more light sources 108.

FIG. 19D illustrates an embodiment of nitric oxide permeable housing 104. Nitric oxide permeable housing 104 is illustrated as including a nitric oxide permeable membrane 1600. Nitric oxide permeable housing 104 includes a cavity 1900 configured to accept one or more photolyzable nitric oxide donors 106. The nitric oxide permeable housing 104 includes a cavity 1910 configured to accept one or more light sources 108.

FIG. 20A illustrates an embodiment of nitric oxide permeable housing 104. Nitric oxide permeable housing 104 is illustrated as including a nitric oxide impermeable portion 2020 of the nitric oxide permeable housing 104 and a controllable valve 1800. The nitric oxide permeable housing 104 includes a cavity 2010 configured to accept one or more light sources 108 and a cavity 2000 configured to accept one or more photolyzable nitric oxide donors 106.

FIG. 20B illustrates an embodiment of nitric oxide permeable housing 104. Nitric oxide permeable housing 104 is illustrated as including a nitric oxide impermeable portion 2020 of the nitric oxide permeable housing 104 and a controllable valve 1800. The nitric oxide permeable housing 104 includes a cavity 2010 configured to accept one or more light sources 108 and a cavity 2000 configured to accept one or more photolyzable nitric oxide donors 106.

FIG. 20C illustrates an embodiment of nitric oxide permeable housing 104. Nitric oxide permeable housing 104 is illustrated as including a nitric oxide impermeable portion 2020 of the nitric oxide permeable housing 104 and a controllable valve 1800. The nitric oxide permeable housing 104 includes a cavity 2010 configured to accept one or more light sources 108 and a cavity 2000 configured to accept one or more photolyzable nitric oxide donors 106.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoff's. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal-bearing medium used to actually carry out the distribution. Examples of a signal-bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, those skilled in the art will recognize that the various embodiments described herein can be implemented, individually and/or collectively, by various types of electromechanical systems having a wide range of electrical components such as hardware, software, firmware, or virtually any combination thereof; and a wide range of components that may impart mechanical force or motion such as rigid bodies, spring or torsional bodies, hydraulics, and electro-magnetically actuated devices, or virtually any combination thereof. Consequently, as used herein "electro-mechanical system" includes, but is not limited to, electrical circuitry operably coupled with a transducer (e.g., an actuator, a motor, a piezoelectric crystal, etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), electrical circuitry forming a communications device (e.g., a modem, communications switch, or optical-electrical equipment), and any non-electrical analog thereto, such as optical or other analogs. Those skilled in the art will also appreciate that examples of electromechanical systems include but are not limited to a variety of consumer electronics systems, as well as other systems such as motorized transport systems, factory automation systems, security systems, and communication/computing systems. Those skilled in the art will recognize that electromechanical as used herein is not necessarily limited to a system that has both electrical and mechanical actuation except as context may dictate otherwise.

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

Those skilled in the art will recognize that it is common within the art to implement devices and/or processes and/or systems in the fashion(s) set forth herein, and thereafter use engineering and/or business practices to integrate such implemented devices and/or processes and/or systems into more comprehensive devices and/or processes and/or systems. That is, at least a portion of the devices and/or processes and/or systems described herein can be integrated into other devices and/or processes and/or systems via a reasonable amount of experimentation. Those having skill in the art will recognize that examples of such other devices and/or processes and/or systems might include—as appropriate to context and application—all or part of devices and/or processes and/or systems of (a) an air conveyance (e.g., an airplane, rocket, hovercraft, helicopter, etc.), (b) a ground conveyance (e.g., a car, truck, locomotive, tank, armored personnel carrier, etc.), (c) a building (e.g., a home, warehouse, office, etc.), (d) an appliance (e.g., a refrigerator, a washing machine, a dryer, etc.), (e) a communications system (e.g., a networked system, a telephone system, a voice-over IP system, etc.), (f) a business entity (e.g., an Internet Service Provider (ISP) entity such as Comcast Cable, Quest, Southwestern Bell, etc), or (g) a wired/wireless services entity (e.g., such as Sprint, Cingular, Nextel, etc.), etc.

Although the user interface 122 is shown/described herein as a single illustrated figure that is associated with an individual, those skilled in the art will appreciate that a user interface 122 may be utilized by a user 124 that is a representative of a human user 124, a robotic user 124 (e.g., computational entity), and/or substantially any combination thereof (e.g., a user 124 may be assisted by one or more robotic based systems). In addition, a user 124 as set forth herein, although shown as a single entity may in fact be composed of two or more entities. Those skilled in the art will appreciate that, in general, the same may be said of "sender" and/or other entity-oriented terms as such terms are used herein.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

All publications, patents and patent applications cited herein are incorporated herein by reference. The foregoing specification has been described in relation to certain embodiments thereof, and many details have been set forth for purposes of illustration, however, it will be apparent to those skilled in the art that the invention is susceptible to additional embodiments and that certain of the details described herein may be varied considerably without departing from the basic principles of the invention.

What is claimed is:

1. An apparatus comprising:
   one or more housings that include one or more ports that facilitate release of nitric oxide from the one or more housings;
   one or more photolyzable nitric oxide donors included within the one or more housings; and
   one or more control units operable to control opening and/or closing of one or more ports in response to one or more signals from at least one sensor.

2. The apparatus of claim 1, wherein the one or more housings that include one or more ports that facilitate release of nitric oxide from the one or more housings comprises:
   one or more housings that include (i) one or more nitric oxide permeable membranes and (ii) one or more ports that facilitate release of nitric oxide from the one or more housings.

3. The apparatus of claim 1, wherein the one or more housings that include one or more ports that facilitate release of nitric oxide from the one or more housings comprises:
   one or more housings that include (i) one or more window portions and (ii) one or more ports that facilitate release of nitric oxide from the one or more housings.

4. The apparatus of claim 1, wherein the one or more housings that include one or more ports that facilitate release of nitric oxide from the one or more housings comprises:
   one or more housings configured for detachable connection to one or more light sources and that include one or more ports that facilitate release of nitric oxide from the one or more housings.

5. The apparatus of claim 1, wherein the one or more photolyzable nitric oxide donors included within the one or more housings comprises:
   one or more photolyzable nitric oxide donors associated with one or more polymeric materials included within the one or more housings.

6. The apparatus of claim 1, wherein the one or more photolyzable nitric oxide donors included within the one or more housings comprises:
   one or more photolyzable nitric oxide donors that include one or more diazeniumdiolates and that are included within the one or more housings.

7. The apparatus of claim 1, further comprising:
   one or more quantum dots.
8. The apparatus of claim 1, further comprising:
   one or more rare-earth materials.
9. The apparatus of claim 1, wherein the apparatus is fully implantable in vivo.
10. The apparatus of claim 1, further comprising:
    at least one user interface.
11. The apparatus of claim 1, further comprising:
    at least one transmitter.
12. The apparatus of claim 1, further comprising:
    at least one receiver.
13. The apparatus of claim 1, further comprising:
    one or more fluorescent materials.
14. The apparatus of claim 1, further comprising:
    one or more light emitting diodes.
15. The apparatus of claim 1, further comprising:
    one or more light sources at least partially coated with the one or more photolyzable nitric oxide donors.
16. The apparatus of claim 1, further comprising:
    one or more light sources operable to emit infrared and/or ultraviolet light.
17. The apparatus of claim 1, further comprising:
    one or more light sources operable to emit visible light.
18. The apparatus of claim 1, further comprising:
    one or more light sources integrated within the one or more housings.
19. The apparatus of claim 1, further comprising:
    one or more light sources operable to emit light to facilitate release of nitric oxide from the one or more photolyzable nitric oxide donors.
20. The apparatus of claim 19, wherein the one or more control units operable to control opening and/or closing of the one or more ports in response to one or more signals from at least one sensor comprises:
    one or more control units operable to (i) control opening and/or closing of the one or more ports in response to one or more signals from at least one sensor and (ii) regulate the one or more light sources.
21. The apparatus of claim 19, wherein the one or more control units operable to control opening and/or closing of the one or more ports in response to one or more signals from at least one sensor comprises:
    one or more control units operable to (i) control opening and/or closing of the one or more ports in response to one or more signals from at least one sensor and (ii) regulate the one or more light sources in response to one or more programs.
22. The apparatus of claim 19, wherein the one or more control units operable to control opening and/or closing of the one or more ports in response to one or more signals from at least one sensor comprises:
    one or more control units operable to (i) control opening and/or closing of the one or more ports in response to one or more signals from at least one sensor and (ii) regulate the one or more light sources in response to one or more timers.
23. The apparatus of claim 19, further comprising:
    one or more quantum dots.
24. The apparatus of claim 19, further comprising:
    one or more rare-earth materials.

* * * * *